US007803614B2

(12) United States Patent
Kawakami et al.

(10) Patent No.: US 7,803,614 B2
(45) Date of Patent: *Sep. 28, 2010

(54) MELANOMA ANTIGENS AND THEIR USE IN DIAGNOSTIC AND THERAPEUTIC METHODS

(75) Inventors: Yutaka Kawakami, Kanagawa (JP); Steven A. Rosenberg, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/932,255

(22) Filed: Oct. 31, 2007

(65) Prior Publication Data

US 2008/0233637 A1 Sep. 25, 2008

Related U.S. Application Data

(60) Continuation of application No. 11/772,277, filed on Jul. 2, 2007, which is a continuation of application No. 11/751,233, filed on May 21, 2007, now Pat. No. 7,612,044, which is a continuation of application No. 10/685,977, filed on Oct. 15, 2003, now Pat. No. 7,232,887, which is a division of application No. 09/898,860, filed on Jul. 3, 2001, now Pat. No. 6,965,017, which is a division of application No. 09/267,439, filed on Mar. 12, 1999, now Pat. No. 6,270,778, which is a division of application No. 09/073,138, filed on May 5, 1998, now Pat. No. 6,537,560, which is a continuation of application No. 08/417,174, filed on Apr. 5, 1995, now Pat. No. 5,844,075, which is a continuation-in-part of application No. 08/231,565, filed on Apr. 22, 1994, now Pat. No. 5,874,560.

(51) Int. Cl.
*C12N 15/00* (2006.01)

(52) U.S. Cl. .................................. 435/320.1; 536/23.1

(58) Field of Classification Search ........................ None
See application file for complete search history.

(56) References Cited

U.S. PATENT DOCUMENTS

| 5,262,177 | A | 11/1993 | Brown et al. |
| 5,342,774 | A | 8/1994 | Boon et al. |
| 5,620,886 | A | 4/1997 | Brichard et al. |
| 5,679,511 | A | 10/1997 | Kwon |
| 5,837,476 | A | 11/1998 | Brichard et al. |
| 5,854,203 | A | 12/1998 | Brichard et al. |
| 5,856,091 | A | 1/1999 | Brichard et al. |
| 5,994,523 | A | 11/1999 | Kawakami et al. |
| 6,001,975 | A | 12/1999 | Brichard et al. |
| 6,201,111 | B1 | 3/2001 | Brichard et al. |
| 6,270,778 | B1 * | 8/2001 | Kawakami et al. ....... 424/277.1 |
| 6,500,919 | B1 | 12/2002 | Adema et al. |
| 6,660,276 | B1 | 12/2003 | Slingluff et al. |

FOREIGN PATENT DOCUMENTS

| DE | 3341367 | 5/1984 |
| EP | 0668350 | 8/1995 |
| GB | 2133543 | 8/1984 |
| WO | WO 92/21767 A1 | 12/1992 |
| WO | 9314189 | 7/1993 |
| WO | WO 94/21126 A1 | 9/1994 |
| WO | 9423067 | 10/1994 |
| WO | 9522561 | 8/1995 |
| WO | WO 96/01557 A1 | 1/1996 |

OTHER PUBLICATIONS

Ikeda et al BBRC vol. 192 p. 1-6 (1993)(abstract only).*
Coulie, P.G. et al. (1993) "Genes coding for tumor antigens recognized by human cytolytic T-lymphocytes" *J. Immunotherap.* 14:104-109.
Coulie P.G. et al. "A new gene coding for a differentiation antigen recognized by autologous cytolytic T lymphocytes on HLA-A2 melanomas", *J. Exp Med* (1994) 180:35-42.
Maresh, C.A. et al.: Cloning and expression of the gene for the melanoma associated ME2O antigen. *DNA and Cell Biology*, 1994; 13:87-95.
Cox, A.L., et al. "Identification of a peptide recognized by five melanoma-specific human cytotoxic T cell lines" *Science* 1994; 264:716-719.
Brichard, V., et al.: "The tyrosinase gene codes for an antigen recognized by autologous cytolytic T lymphocytes on HLA-A2 melanomas". *J. Exp. Med.* 1993; 178:489-495.

(Continued)

*Primary Examiner*—Sheela J Huff
(74) *Attorney, Agent, or Firm*—Leydig, Voit & Mayer

(57) ABSTRACT

The present invention provides a nucleic acid sequence encoding a melanoma antigen recognized by T lymphocytes, designated MART-1. This invention further relates to bioassays using the nucleic acid sequence, protein or antibodies of this invention to diagnose, assess or prognoses a mammal afflicted with melanoma or metastata melanoma. This invention also provides immunogenic peptides derived from the MRT-1 melanoma antigen and a second melanoma antigen designated gp100. This invention further provides immunogenic peptides derived from the MART-1 melanoma antigen or gp100 antigen which have been modified to enhance their immunogenicity. The proteins and peptides provided can serve as an immunogen or vaccine to prevent or treat melanoma.

11 Claims, 13 Drawing Sheets

OTHER PUBLICATIONS

Gaugler, B., et al. "Human gene MAGE-3 codes for an antigen recognized on a melanoma by autologous cytolytic T lymphocytes". *J. Exp. Med.* 1994; 179:921-930.

Traversari, C., et al.: "A nonapeptide encoded by human gene MAGE-1 is recognized on HLA-A1 by cytolytic T lymphocytes directed against tumor antigen MZ2-E". *J. Exp. Med.* 1992; 176:1453-1457.

Cellis, E., et al.: "Induction of anti-tumor cytotoxic T lymphocytes in normal humans using primary cultures and synthetic peptides epitopes". *Proc. Natl. Acad. Sci. U.S.A.* 1994; 91;2105-2109.

Boon, T.: "Toward a genetic analysis of tumor rejection antigens". *Adv. Cancer Res.* 1992; 58:177-210.

Kawakami, Y., et al.; T-cell recognition of human melanoma antigens. *J. Immunother.* 1993; 14:88-93.

Bakker, A.B.H., et al.: Melanocyte lineage-specific antigen gp100 is recognized by melanocyte-derived tumor infiltrating lymphocytes. *J. Exp. Med.* 1994; 179:1005-1009.

Wölfel, T., et al.: Two tyrosinase nonapeptides recognized on HLA-A2 melanomas by autologous cytolytic T. lymphocytes. *Eur. J. Immunol.* 1994; 24:759-764.

Adema, G.J., et al.: Melanocyte lineage-specific antigens recognized by monoclonal antibodies NK1-beteb, HMB-50, and HMB-45 are encoded by a single cDNA. *Am J. Pathol.* 1993; 143:1579-1585.

Kwon, B.S., et al.: A melanocyte-specific gene, Pmel 17, maps near the silver coat color locus on mouse chromosome 10 and is in a syntenic region on human chromosome 12. *Proc. Natl. Acad. Sci. USA* 1991; 88:9228-9232.

Rosenberg, S.A., et al.: Use of tumor infiltrating lymphocytes and interleukin-2 in the immunotherapy of patients with metastatic melanoma. Preliminary report. *N. Engl. J. Med.* 1988; 319:1676-1680.

Kawakami, Y., et al.,: Shared human melanoma antigens. Recognition by tumor infiltrating lymphocytes in HLA-A2.1 transfected melanomas. *J. Immunol* 1992; 148:638-643.

Van der Bruggen, et al.: A gene encoding an antigen recognized by cytolytic T. lymphocytes on a human melanoma. *Science* 1991; 254:1643-1647.

Falk, K., et al.: "Allele-specific motifs revealed by sequencing of self-peptides eluted from MHC molecules." *Nature* 1991, 351:290-296.

Kubo, R., et al.: "Definition of specific peptide motifs for four major HLA-A Alleles." *Journal of Immunology* 1994; 152:3913-3924.

Parker, K., et al.: "Sequence motifs important for peptide binding to the human MHC class 1 molecule. HLA-A2." 1992, J. Immunol:3580-3587.

Ruppert, J., et al.: "Prominent role of secondary anchor residues in peptide binding to HLA-A2.1 molecules." *Cell* 1993, 74:929-937.

Storkus, W., et al.: "Identification of human melanoma peptides recognized by class 1 restricted tumor infiltrating T lymphocytes." *Journal of Immunology* 1993, 151:3719-3727.

Kawakami, Y., et al.: "Cloning of the gene coding for a shared human melanoma antigen recognized by autologous T cells infiltrating into tumor." *Pro. Natl. Acad. Sci. USA* 1994; 91:3515-3519.

Adema, G.J. et al., "Molecular characterization of the melanocyte lineage-specific antigen gp100." *Journal of Biological Chemistry* 1994, 269:20126-20133.

EMBL Database Accession No. M32295:26-11-90 Vogel A.: Human KD melanocyte specific secreted glycoprotein MRNA 3'end'.

Kawakami, Y., et al., "Identification of a human melanoma antigen recognized by tumor-infiltrating lymphocytes associated with in vivo tumor rejection" *PNAS* 91:6458-6462 1994.

Kawakami, Y., et al., "Identification of the Immunodominant Peptides of the MART-1 Human Melanoma Antigen Recognized by the Majority of HLA-A2-restricted Tumor Infiltrating Lymphocytes" *J. Exp. Med.* 180:347-352, 1994.

Rivoltini, L., et al., "Induction of Tumor-Reactive CTL from Peripheral Blood and Tumor-Infiltrating Lymphocytes of Melanoma Patients by In Vitro StImulation with an Immunodominant Peptide of the Human Melanoma Antigen MART-1" *Journal of Immunology*, 1995, 154:2257-2265.

Slingluff, C.L.,Jr., et al., "Direct analysis of tumor-associated peptide antigens" *Current Opinion in Immunology* 1994, 6:733-740.

Cole, D.J., et al., "Characterization of the Functional Specificity of a Cloned T-Cell Receptor Heterodimer Recognizing the MART-1 Melanoma Antigen" *Cancer Res.* 55:748-752 Feb. 1995.

Cole, D.J., et al., "Identification of MART-1-specific T-Cell Receptors: T Cells Utilizing Distinct T-Cell Receptor Variable and Joining Regions Recognize the Same Tumor Epitope" *Cancer Res.* 54:5265-5268, 1994.

Castelli, C., et al., "Mass Spectrometric Identification of a Naturally Processed Melanoma Peptide Recognized by $CD8^+$ Cytotoxic T Lymphocytes" *J. Exp. Med.* 181:363-368 1995.

Sette, A., et al., "Peptide Binding To The Most Frequent HLA-A Class I Alleles Measured By Quantitative Molecular Binding Assays" *Molecular Immunology* 31:813-822, 1994.

Wölfel, T., et al., "Analysis Of Antigens Recognized On Human Melanoma Cells By A2-Restricted Cytolytic T Lymphocytes (CTL)" *Int. J. Cancer* 55:237-244, 1993.

Wölfel, T., et al., "Isolation Of Naturally Processed Peptides Recognized By Cytolytic Lymphocytes (CTL) On Human Melanoma Cells In Association With HLA-A2.1" *Int. J. Cancer* 57:413-418, 1994.

Topalian, S.L., et al., "Human $CD4^+$ T Cells Specifically Recognize a Shared Melanoma-Associated Antigen Encoded by the Tyrosinase Gene" *PNAS* 91:9461-9465, 1994.

Boël, P., et al., "BAGE: a New Gene Encoding an Antigen Recognized on Human Melanomas by Cytolytic T Lymphocytes" *Immunity* 2:167-175 1995.

Slingluff, C.L., Jr., et al., "Recognition of Human Melanoma Cells by HLA-A2.1-Restricted Cytotoxic T Lymphocytes Is Mediated by at Least Six Shared Peptide Epitopes" *Journal of Immunology* 150:2955-2963 1993.

GENBANK Database Accession No. M77348—Human PMEL 17 in RNA—Jan. 2, 1995.

GENBANK Database Accession No. U06654—Human Differentiation Antigen Melan-A Protein in RNA—Jul. 30, 1994.

GENBANK Database Accession No. U06452—Human Melanoma Antigen Recognized by T-Cells (MAR7-1) MRNA—Jun. 25, 1994.

GENBANK Database Accession No. S73003—GP100 Melanocyte Lineage Specific Antigen / PMELL 7 Jan. 25, 1995.

GENBANK Database Accession No. U01874—Human ME20 MRNA May 27, 1994.

Campbell, *Monoclonal Antibody Technology*, 13, Chapter 1, 1-32 (1986).

Cohen, *Science*, 262, 841-843 (1993).

Lewin, *Science*, 237, 1570 (1987).

Reeck et al., *Cell*, 50, 667 (1987).

Storkus et al, *J. Immunol.*, 161(7), 3719-3727 (1993).

Vennegoor et al., *Am. J. Pathol.*, 130, 179 (1988).

Webster's New Riverside Dictionary, p. 365 (1984).

Dermer, *Bio/Technology*, 12, 320 (1994).

Essell, *J. NIH. Res.*, 7, 46-49 (1995).

Freshney, Culture of Animal Cells, A Manual of Basic Technique, Alan R. Liss, Inc., p. 3-4, New York (1983).

Gura, *Science*, 278, 1041-1042 (1997).

Jain, *Sci. Am.*, 271(1), 58-65 (1994).

Spitler, *Cancer Biotherapy*, 10(1), 1-3 (1995).

Tockman et al., *Cancer Research, Supp.* 52, 2711s-2718s (May 1, 1992).

Haigh et al., *Oncology*, 13, 1561-1568 (1999).

* cited by examiner

```
1    AGCAGACAGAGGACTCTCATTAAGGAAGG  TGTCCTGTGCCCTGACCCTACAAGATGCCA         59
                                                            MetPro        2

60   AGAGAAGATGCTCACTTCATCTATGGTTAC CCCAAGAAGGGCACGGGCCACTCTTACACC         119
3    ArgGluAspAlaHisPheIleTyrGlyTyr ProLysLysGlyHisGlyHisSerTyrThr         22

120  ACGGCTGAAGAGGCCGCTGGGATCGGCATC CTGACAGTGATCCTGGGAGTCTTACTGCTC         180
23   ThrAlaGluGluAlaAlaGlyIleGlyIle LeuThrValIleLeuGlyValLeuLeuLeu         43

181  ATCGGCTGTGTTGGTATTGTAGAAGACGAAAT GGATACAGAGCCTTGATGGATAAAAGTCTT       239
44   IleGlyCysValGlyIleValGluAspGluMet GlyTyrArgAlaLeuMetAspLysSerLeu     62

240  CATGTTGGCACTCAATGTGCCCTTAACAAGA AGATGCCCACAAGAAGGGTTTGATCATCGG        300
63   HisValGlyThrGlnCysAlaLeuThrArg ArgCysProGlnGluGlyPheAspHisArg        83

301  GACAGCAAAGTGTCTCTTCAAGAGAAAAAAC TGTGAACCTGTGGTTCCCAATGCTCCACCT        359
84   AspSerLysValSerLeuGlnGluLysAsn CysGluProValValProAsnAlaProPro        102

360  GCTTATGAGAAACTCTCTGCAGAACAGTCA CCACCACCTTATTCACCTTAAGAGCCAGCG         420
103  AlaTyrGluGluLysLeuSerAlaGluGlnSer ProProProTyrSerPro                  118

421  AGACACCTGAGACATGCTGAAATTATTTCT CTCACACTTTTGCTTGAATTTAATACAGAC         479
```

FIG. 1A

| | | |
|---|---|---|
| 480 | ATCTAATGTTCTCCCTTGGAATGGTGTAGG | AAAAATGCAAGCCATCTCTAATAATAAGTC | 540 |
| 541 | AGTGTTAAAATTTAGTAGGTCCGCTAGCA | GTACTAATCATGTGAGGAAATGATGAGAAA | 599 |
| 600 | TATTAAATTGGGAAAACTCCATCAATAAAT | GTTGCAATGCATACAGAATATCTGTGCCAGA | 660 |
| 661 | GGTAATGTTAGTAAATCCATGGTGTTATTT | TCTGAGAGACAGAATTCAAGTGGGTATTCT | 719 |
| 720 | GGGGCCATCCAATTTCTCTTTACTTGAAAT | TTGGCTAATAACAAACTAGTCAGGTTTTCG | 780 |
| 781 | AACCTTGACCGACATGAACTGTACACAGAA | TTGTTCCAGTACTATGGAGTGCTCACAAAG | 839 |
| 840 | GATACTTTTACAGGTAAGACAAAGGGTTG | ACTGGCCTATTTATCTGATCAAGAACATGT | 900 |
| 901 | CAGCAAATGTCTCTTTGTGCTCTAAAATTCT | ATTATACTACAATAATATATTGTAAAGATC | 959 |
| 960 | CTATAGCTCTCTCTTTTTTTTTGAGATGGAGTTT | CGCTTTTGTTGCCCAGGCTGGAGTGCAATG | 1020 |
| 1021 | GCGCGATCTTGGCTCACCATAACCTCCGCC | TCCCAGGTTCAAGCAATTCTCCTGCCTTAG | 1079 |
| 1080 | CCTCCGAGTAGCTGGGATTACAGGCGTGC | GCCACTATGCCTGACTAATTTTGTAGTTTT | 1140 |
| 1141 | AGTAGAGACGGGGTTTCTCAGCCCATGTTGGTCA | GGCTGGTCTCAAACTCCTGACCTCAGGTGA | 1199 |
| 1200 | TCTGCCCGCCTATATCTTAGGTAAGACATGCTGG | AATTACAGGCGTGAGCCACCACGCCTGGCT | 1260 |
| 1261 | GGATCCTATATCTTAGGTAAGACAAGTATA | GCAGTCTAATTACAGAAATTGGTAGAAGGATTT | 1319 |
| 1320 | AATGCTATTCTAACTAATGACTATGTACTGCCTT | CTACTAAAACCAGAGCCTGTGTACTGCCTTAAATG | 1380 |
| 1381 | AAATAAGTAAAAGCTACTATGCTCTCTTGGGTTC | AGTGCTGATGCCTGTGTACTGCCTTAAATG | 1439 |
| 1440 | TACCTATGGCAATTTAGCTCTCTTGGGTTC | CCAAATCCCTCTCACAAGAATGTGCAGAAG | 1500 |
| 1501 | AAATCATAAAGGATCAGAGATTCTGAAAA | AAAAAAAAAAAAAAAAAAAAAAAAAAAAAA | 1559 |

FIG. 1B

| | |
|---|---|
| GTCGACGGCC ATTACCAATC GCGACCGGGA AGAACACAAT | 40 |
| GGATCTGGTG CTAAAAAGAT GCCTTCTTCA TTTGGCTGTG | 80 |
| ATAGGTGCTT TGCTGGCTGT GGGGGCTACA AAAGTACCCA | 120 |
| GAAACCAGGA CTGGCTTGGT GTCTCAAGGC AACTCAGAAC | 160 |
| CAAAGCCTGG AACAGGCAGC TGTATCCAGA GTGGACAGAA | 200 |
| GCCCAGAGAC TTGACTGCTG GAGAGGTGGT CAAGTGTCCC | 240 |
| TCAAGGTCAG TAATGATGGG CCTACACTGA TTGGTGCAAA | 280 |
| TGCCTCCTTC TCTATTGCCT TGAACTTCCC TGGAAGCCAA | 320 |
| AAGGTATTGC CAGATGGGCA GGTTATCTGG GTCAACAATA | 360 |
| CCATCATCAA TGGGAGCCAG GTGTGGGGAG GACAGCCAGT | 400 |
| GTATCCCCAG GAAACTGACG ATGCCTGCAT CTTCCCTGAT | 440 |
| GGTGGACCTT GCCCATCTGG CTCTTGGTCT CAGAAGAGAA | 480 |
| GCTTTGTTTA TGTCTGGAAG ACCTGGGGCC AATACTGGCA | 520 |
| ATTTCTAGGG GGCCCAGTGT CTGGGCTGAG CATTGGGACA | 560 |
| GGCAGGGCAA TGCTGGGCAC ACACACCATG GAAGTGACTG | 600 |
| TCTACCATCG CCGGGGATCC CGGAGCTATG TGCCTCTTGC | 640 |
| TCATTCCAGC TCAGCCTTCA CCATTACTGA CCAGGTGCCT | 680 |
| TTCTCCGTGA GCGTGTCCCA GTTGCGGGCC TTGGATGGAG | 720 |
| GGAACAAGCA CTTCCTGAGA AATCAGCCTC TGACCTTTGC | 760 |
| CCTCCAGCTC CATGACCCCA GTGGCTATCT GGCTGAAGCT | 800 |
| GACCTCTCCT ACACCTGGGA CTTTGGAGAC AGTAGTGGAA | 840 |
| CCCTGATCTC TCGGGCACTT GTGGTCACTC ATACTTACCT | 880 |
| GGAGCCTGGC CCAGTCACTG CCCAGGTGGT CCTGCAGGCT | 920 |
| GCCATTCCTC TCACCTCCTG TGGCTCCTCC CCAGTTCCAG | 960 |
| GCACCACAGA TGGGCACAGG CCAACTGCAG AGGCCCCTAA | 1000 |
| CACCACAGCT GGCCAAGTGC CTACTACAGA AGTTGTGGGT | 1040 |
| ACTACACCTG GTCAGGCGCC AACTGCAGAG CCCTCTGGAA | 1080 |
| CCACATCTGT GCAGGTGCCA ACCACTGAAG TCATAAGCAC | 1120 |

FIG. 4A

| | |
|---|---|
| TGCACCTGTG CAGATGCCAA CTGCAGAGAG CACAGGTATG | 1160 |
| ACACCTGAGA AGGTGCCAGT TTCAGAGGTC ATGGGTACCA | 1200 |
| CACTGGCAGA GATGTCAACT CCAGAGGCTA CAGGTATGAC | 1240 |
| ACCTGCAGAG GTATCAATTG TGGTGCTTTC TGGAACCACA | 1280 |
| GCTGCACAGG TAACAACTAC AGAGTGGGTG GAGACCACAG | 1320 |
| CTAGAGAGCT ACCTATCCCT GAGCCTGAAG GTCCAGATGC | 1360 |
| CAGCTCAATC ATGTCTACGG AAAGTATTAC AGGTTCCCTG | 1400 |
| GGCCCCTGC TGGATGGTAC AGCCACCTTA AGGCTGGTGA | 1440 |
| AGAGACAAGT CCCCCTGGAT TGTGTTCTGT ATCGATATGG | 1480 |
| TTCCTTTTCC GTCACCCTGG ACATTGTCCA GGGTATTGAA | 1520 |
| AGTGCCGAGA TCCTGCAGGC TGTGCCGTCC GGTGAGGGGG | 1560 |
| ATGCATTTGA GCTGACTGTG TCCTGCCAAG GCGGGCTGCC | 1600 |
| CAAGGAAGCC TGCATGGAGA TCTCATCGCC AGGGTGCCAG | 1640 |
| CCCCCTGCCC AGCGGCTGTG CCAGCCTGTG CTACCCAGCC | 1680 |
| CAGCCTGCCA GCTGGTTCTG CACCAGATAC TGAAGGGTGG | 1720 |
| CTCGGGGACA TACTGCCTCA ATGTGTCTCT GGCTGATACC | 1760 |
| AACAGCCTGG CAGTGGTCAG CACCCAGCTT ATCATGCCTG | 1800 |
| GTCAAGAAGC AGGCCTTGGG CAGGTTCCGC TGATCGTGGG | 1840 |
| CATCTTGCTG GTGTTGATGG CTGTGGTCCT TGCATCTCTG | 1880 |
| ATATATAGGC GCAGACTTAT GAAGCAAGAC TTCTCCGTAC | 1920 |
| CCCAGTTGCC ACATAGCAGC AGTCACTGGC TGCGTCTACC | 1960 |
| CCGCATCTTC TGCTCTTGTC CCATTGGTGA GAACAGCCCC | 2000 |
| CTCCTCAGTG GGCAGCAGGT CTGAGTACTC TCATATGATG | 2040 |
| CTGTGATTTT CCTGGAGTTG ACAGAAACAC CTATATTTCC | 2080 |
| CCCAGTCTTC CCTGGGAGAC TACTATTAAC TGAAATAAAT | 2120 |
| ACTCAGAGCC TGAAAAAAAA TAAAAAAAAA AAAAAAAAA | 2160 |
| AAAAAAAAAA AA | 2172 |

FIG. 4B

```
  1  MDLVLKRCLL HLAVIGALLA VGATKVPRNQ DWLGVSRQLR TKAWNRQLYP
 51  EWTEAQRLDC WRGGQVSLKV SNDGPTLIGA NASFSIALNF PGSQKVLPDG
101  QVIWVNNTII NGSQVWGGQP VYPQETDDAC IFPDGGPCPS GSWSQKRSFV
151  YVWKTWGQYW QFLGGPVSGL SIGTGRAMLG THTMEVTVYH RRGSRSYVPL
201  AHSSSAFTIT DQVPFSVSVS QLRALDGGNK HFLRNQPLTF ALQLHDPSGY
251  LAEADLSYTW DFGDSSGTLI SRALVVTHTY LEPGPVTAQV VLQAAIPLTS
301  CGSSPVPGTT DGHRPTAEAP NTTAGQVPTT EVVGTTPGQA PTAEPSGTTS
351  VQVPTTEVIS TAPVQMPTAE STGMTPEKVP VSEVMGTTLA EMSTPEATGM
401  TPAEVSIVVL SGTTAAQVTT TEWVETTARE LPIPEPEGPD ASSIMSTESI
451  TGSLGPLLDG TATLRLVKRQ VPLDCVLYRY GSFSVTLDIV QGIESAEILQ
501  AVPSGEGDAF ELTVSCQGGL PKEACMEISS PGCQPPAQRL CQPVLPSBAC
551  QLVLHQILKG GSGTYCLNVS LADTNSLAVV STQLIMPGQE AGLGQVPLIV
601  GILLVLMAVV LASLIYRRRL MKQDFSVPQL PHSSSHWLRL PRIFCSCPIG
651  ENSPLLSGQQ V
```

FIG. 5A

```
Pme117      M-----V-----Q-----P-----VPGILLT-----LLSGQQV
ME20        M-----V-----Q-----L-----      ............
gp100       M-----V-----Q-----L-----      ............
cDNA25FL    M-----F-----Q-----L-----      ............
cDNA25TR          Q-----L-----........-----PPQWAAGLSTLI
            1    162   236   274   588         649
```

```
  1       MDLVLKRCLL HLAVIGALLA VGATKVPRNQ DWLGVSRQLR TKAWNRQLYI
          D3---------- ---------- ---------- ---------- ----------
          D5---------- ---------- ---------- ---------- ----------
          D4---------- ---------- ---------- ---------- ----------
          C4---------- ---------- ---------- ---------- ----------
 51       EWTEAQRLDC WRGGQVSLKV SNDGPTLIGA NASFSIALNF PGSQKVLPDC
          D3---------- ---------- ---------- ---------- ----------
          D5---------- ---------- ---------- ---------- ----------
          D4---------- ---------- ---------- ---------- ----------
          C4---------- ---------- ---------- ---------- ----------
101       QVIWVNNTII NGSQVWGGQP VYPQETDDAC IFPDGGPCPS GSWSQKRSFV
          D3---------- ---------- ---------- ---------- ----------
          D5---------- ---------- ---------- ---------- ----------
          D4---------- ---------- ---------- ---------- ----------
          C4---------- ---------- ---------- ---------- ----------
151       YVWKTWGQYW QVLGGPVSGL SIGTGRAMLG THTMEVTVYH RRGSRSYVPL
          D3-----D3   ---------- ---------- ---------- ----------
          D5---------- ---D5     ---------- ---------- ----------
          D4---------- ---------- ---------- ---------- -----D4
          C4---------- ---------- ---------- ---------- ----------
201       AHSSSAFTIT DQVPFSVSVS QLRALDGGNK HFLRNQPLTF ALQLHDPSGY
          C4---------- ---------- ---------- ---------- ----------
                                            25TR------ ----------
251       LAEADLSYTW DFGDSSGTLI SRALVVTHTY LEPGPVTAQV VLQAAIPLTS
          C4---------- ----------C4
          25TR-------- ---------- ---------- ---------- ----------
301       CGSSPVPGTT DGHRPTAEAP NTTAGQVPTT EVVGTTPGQA PTAEPSGTTS
          25TR-------- ---------- ---------- ---------- ----------
351       VQVPTTEVIS TAPVQMPTAE STGMTPEKVP VSEVMGTTLA EMSTPEATGM
          25TR-------- ---------- ---------- ---------- ----------
401       TPAEVSIVVL SGTTAAQVTT TEWVETTARE LPIPEPEGPD ASSIMSTESI
          25TR-------- ---------- ---------- ---------- ----------
451       TGSLGPLLDG TATLRLVKRQ VPLDCVLYRY GSFSVTLDIV QGIESAEILQ
          25TR-------- ---------- ---------- ---------- ----------
501       AVPSGEGDAF ELTVSCQGGL PKEACMEISS PGCQPPAQRL CQPVLPSPAC
          25TR-------- ---------- ---------- ---------- ----------
551       QLVLHQILKG GSGTYCLNVS LADTNSLAVV STQLIMPGQE AGLGQVPLIV
          25TR-------- ---------- ---------- ---------- ----------
601       GILLVLMAVV LASLIYRRRL MKQDFSVPQL PHSSSHWLRL PRIFCSCPIG
          25TR-------- ---------- ---------- ---------- ----------
651       ENSPLLSGQQ V
          25TR-------- -25TR
```

FIG. 7B

| DNA fragment | 620-1 | 620-2 | TIL 660-1 | 1143 | 1200 |
|---|---|---|---|---|---|
| D3 | − | − | − | − | − |
| D5 | − | + | − | − | + |
| D4 | − | + | − | − | + |
| C4 | − | − | − | + | − |
| 25TR | − | − | − | + | − |

MELANOMA ANTIGENS AND THEIR USE IN DIAGNOSTIC AND THERAPEUTIC METHODS

CROSS REFERENCE TO RELATED APPLICATIONS

This application is a continuation of application Ser. No. 11/772,277, filed Jul. 2, 2007, which is a continuation of Ser. No. 11/751,233, filed May 21, 2007, now U.S. Pat. No. 7,612,044, which is a continuation of application Ser. No. 10/685,977, filed Oct. 15, 2003, now U.S. Pat. No. 7,232,887, which is a divisional of Ser. No. 09/898,860, filed Jul. 3, 2001, now U.S. Pat. No. 6,965,017 which is a divisional of application Ser. No. 09/267,439, filed Mar. 12, 1999, now U.S. Pat. No. 6,270,778, which is a divisional of application Ser. No. 09/073,138, filed May 5, 1998, now U.S. Pat. No. 6,537,560, which is a continuation of application Ser. No. 08/417,174, filed Apr. 5, 1995, now U.S. Pat. No. 5,844,075, which is a continuation-in-part of application Ser. No. 08/231,565, filed Apr. 22, 1994, now U.S. Pat. No. 5,874,560, all of which are hereby incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 52,111 Byte ASCII (Text) file named "702219ST25-2.TXT," created on Jun. 28, 2010.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 41,155 Byte ASCII (Text) file named "702219ST25.TXT," created on Oct. 31, 2007.

FIELD OF THE INVENTION

This invention is in the field of prevention and treatment of human cancers. More specifically, this invention relates to genes encoding melanoma antigens recognized by T-Cells and their corresponding proteins and to preventative, diagnostic and therapeutic applications which employ these genes or proteins.

BACKGROUND OF THE INVENTION

Melanomas are aggressive, frequently metastatic tumors derived from either melanocytes or melanocyte related nevus cells ("Cellular and Molecular Immunology" (1991) (eds) Abbas A. K., Lechtiman, A. H., Pober, J. S.; W. B. Saunders Company, Philadelphia: pages 340-341). Melanomas make up approximately three percent of all skin cancers and the worldwide increase in melanoma is unsurpassed by any other neoplasm with the exception of lung cancer in women ("Cellular and Molecular Immunology" (1991) (eds) Abbas, A. K., Lechtiman, A. H., Pober, J. S.; W.B. Saunders Company Philadelphia pages: 340-342; Kirkwood and Agarwala (1993) *Principles and Practice of Oncology* 7:1-16). Even when melanoma is apparently localized to the skin, up to 30% of the patients will develop systemic metastasis and the majority will die (Kirkwood and Agarwala (1993) *Principles and Practice of Oncology* 7:1-16). Classic modalities of treating melanoma include surgery, radiation and chemotherapy. In the past decade immunotherapy and gene therapy have emerged as new and promising methods for treating melanoma.

T cells play an important role in tumor regression in most murine tumor models. Tumor infiltrating lymphocytes (TIL) that recognize unique cancer antigens can be isolated from many murine tumors. The adoptive transfer of these TIL plus interleukin-2 can mediate the regression of established lung and liver metastases (Rosenberg, S. A., et al., (1986) *Science* 233:1318-1321). In addition, the secretion of IFN-γ by injected TIL significantly correlates with in vivo regression of murine tumors suggesting activation of T-cells by the tumor antigens. (Barth, R. J., et al., (1991) *J. Exp. Med.* 173:647-658). The known ability of tumor TIL to mediate the regression of metastatic cancer in 35 to 40% of melanoma patients when adoptively transferred into patients with metastatic melanoma attests to the clinical importance of the antigens recognized (Rosenberg, S. A., et al., (1988) *N Engl J Med* 319:1676-1680; Rosenberg S. A. (1992) *J. Clin. Oncol.* 10:180-199).

T cell receptors on $CD8^{30}$ T cells recognize a complex consisting of an antigenic peptide (9-10 amino acids for HLA-A2), β-2 microglobulin and class I major histocompatibility complex (MHC) heavy chain (HLA-A, B, C, in humans). Peptides generated by digestion of endogenously synthesized proteins are transported into the endoplastic reticulum, bound to class I MHC heavy chain and β2 microglobulin, and finally expressed in the cell surface in the groove of the class I MHC molecule. Therefore, T cells can detect molecules that originate from proteins inside cells, in contrast to antibodies that detect intact molecules expressed on the cell surface. Therefore, antigens recognized by T cells may be more useful than antigens recognized by antibodies.

Strong evidence that an immune response to cancer exists in human—is provided by the existence of lymphocytes within melanoma deposits. These lymphocytes, when isolated, are capable of recognizing specific tumor antigens on autologous and allogeneic melanomas in an MHC restricted fashion. (Itoh, K. et al. (1986), *Cancer Res.* 46: 3011-3017; Muul, L. M., et al. (1987), *J. Immunol.* 138:989-995); Topalian, S. L., et al., (1989) *J. Immunol.* 142: 3714-3725; Darrow, T. L., et al., (1989) *J. Immunol.* 142: 3329-3335; Hom, S. S., et al., (1991) *J. Immunother.* 10:153-164; Kawakami, Y., et al., (1992) *J. Immunol.* 148: 638-643; Hom, S. S., et al., (1993) *J. Immunother.* 13:18-30; O'Neil, B. H., et al., (1993) *J. Immunol.* 151: 1410-1418). TIL from patients with metastatic melanoma recognize shared antigens including melanocyte-melanoma lineage specific tissue antigens in vitro (Kawakami, Y., et al., (1993) *J. Immunother.* 14: 88-93; Anichini, A. et al., (1993) et al., *J. Exp. Med.* 177: 989-998). Anti-melanoma T cells appear to be enriched in TIL probably as a consequence of clonal expansion and accumulation at the tumor site in vivo (Sensi, M., et al., (1993) *J. Exp. Med.* 178:1231-1246). The fact that many melanoma patients mount cellular and humoral responses against these tumors and that melanomas express both MHC antigens and tumor associated antigens (TAA) suggests that identification and characterization of additional melanoma antigens will be important for immunotherapy of patients with melanoma.

Peripheral blood lymphocytes have been used to identify potential melanoma tumor antigens. Van Der Bruggen et al. (1991) *Science* 254: 1643-1647 has characterized a gene coding for a melanoma antigen, designated MAGE-1, using T cell clones established from the peripheral blood of patients who were repetitively immunized in vivo with mutagenized tumor cells. Cytotoxic T-cells derived from the peripheral blood lymphocytes of patients with melanoma were used to identify a potential antigenic peptide encoding MAGE-1 (Traversari, C., et al. (1992) *J. Exp. Med.* 176:1453-1457). Brichard et al. (1993) *J. Exp. Med.* 178:489-495 has also characterized a gene encoding a melanoma antigen designated tyrosinase using peripheral blood lymphocytes from patients who were sensitized by repetitive in vitro stimulation with tumor. Further support for the therapeutic potential of melanoma antigens is provided by Brown et al. (U.S. Pat. No. 5,262,177). Brown et al. (U.S. Pat. No. 5,262,177) relates to a recombinant vaccinia virus-based melanoma vaccine where the melanoma antigen p97 is reported to show a protective effect from tumor cell challenge in a murine model. Characterization of additional melanoma antigens is important for the development of new strategies for cancer immunotherapy, in particular for melanoma.

SUMMARY OF THE INVENTION

This invention relates, in general, to nucleic acid sequences encoding melanoma antigens recognized by T-lymphocytes (MART-1) and protein and peptides encoded by these sequences. This invention further provides bioassays for these nucleic acid sequences, proteins and peptides. This invention also provides peptides which have been derived from the MART-1 amino acid sequence and modified to enhance their immunogenocity. This invention also provides therapeutic uses for the nucleic acid sequences, proteins, peptides or modified peptides described herein.

It is a general object of the present invention to provide a substantially purified and isolated nucleic acid sequence which encodes for the MART-1 melanoma antigen.

It is another object of this invention to provide a recombinant molecule comprising a vector and all or part of the nucleic acid sequence encoding MART-1.

It is another object of this invention to produce recombinant proteins encoded by all or part of the nucleic acid sequence encoding MART-1.

It is a further object of this invention to provide monoclonal or polyclonal antibodies reactive with the MART-1 protein, peptides or portions thereof.

It is an object of this invention to provide methods of detecting the MART-1 gene or MART-1 mRNA in a biological sample.

It is another object of this invention to provide methods of detecting the MART-1 protein or peptides in a biological sample.

It is an object of this invention to provide diagnostic methods for human disease, in particular for melanomas and metastatic melanomas.

It is a further object of this invention to provide methods for prophylactic or therapeutic uses involving all or part of the nucleic acid sequence encoding MART-1 and its corresponding protein or peptides derived from the MART-1 amino acid sequence.

It is also an object of this invention to provide melanoma vaccines comprising all or part of the nucleic acid sequence encoding MART-1 or its corresponding protein for preventing or treating melanoma.

It is a further object of this invention to provide immunogenic peptides derived from the MART-1 protein sequence for use in vaccines.

It is yet another object of this invention to provide peptides derived from the MART-1 protein sequence which have been modified to increase their immunogenicity or enhance induction of antimelanoma immune response by enhancing their binding to MHC molecules, for use in the prophylactic or therapuetic mothods described herein.

In addition, it is another object of this invention to provide multivalent vaccines comprising all or part of the MART-1 nucleic acid sequence or its corresponding protein or peptides and at least one other immunogenic molecule capable of eliciting the production of antibodies in a mammal to melanoma antigens.

It is another object of this invention to provide a method for preventing or treating melanoma utilizing all or part of the MART-1 nucleic acid sequence or its corresponding protein in gene therapy protocols.

It is a further object of this invention to provide immunogenic peptides derived from a gp100 melanoma antigen protein sequence for use in vaccines.

It is yet another object of this invention to provide peptides derived from a gp100 melanoma antigen sequence which have been modified to increase their immunogenicity or enhance induction of antimelanoma immune response by enhancing binding to MHC molecules for use in the prophylactic and therapeutic methods described herein It is yet another object of this invention to provide a method of prophylactic or therapeutic immunization for melanoma using the vaccines described herein.

It is a further object of this invention to provide a method of identifying melanoma antigens that would constitute potential targets for immunotherapy.

It is yet another object of this invention to provide a method of identifying candidate immunogenic peptides derived from either the MART-1 or gp100 sequences for use in immunotherapy.

DESCRIPTION OF THE FIGURES

FIG. 1 shows the nucleotide and predicted amino acid sequence of the cDNA encoding the MART-1 antigen. The hydrophobic region is underlined.

FIG. 4 show the nucleic acid sequence of the full length cDNA25. The start and stop codons are underlined.

FIG. 5A shows amino acid sequence of the full length cDNA25. The antigenic peptide is underlined.

FIG. 5B shows comparison of the amino acid sequence of the full length cDNA25 (cDNA25FL), the truncated form of cDNA25 (cDNA25TR), Pmel17, ME20 and gp100. (•indicates deletion; - indicates identity).

FIGS. 7A-7B show the location of gp100 epitopes and the DNA fragments tested for epitope analysis and recognition by CTL. FIG. 7A. Five DNA fragments (D3 (SEQ ID NO: 129), D5 (SEQ ID NO: 130), D4 (SEQ ID NO: 131), C4 (SEQ ID NO: 132), 25TR (SEQ ID NO: 133)) tested for epitope analysis are shown (- - -, identical amino acid). Locations of the identified epitopes are underlined. FIG. 7B. Recognition by CTL (620-1, 620-2, 660-1, 1143, 1200) of COS 7 cells transfected with each DNA fragment in pcDNA3 plasmid along with HLA-A2.1 cDNA by IFN-γ secretion assays are shown (+, recognized; –, not recognized).

FIG. 8A, Lysis by TIL1200 of T2 cells incubated with $G9_{154}$ (■) (SEQ ID NO: 46) or $G10_{154}$ (●) (SEQ ID NO: 47). FIG. 8B. Lysis by TIL620 of T2 cells incubated with $G9_{209}$ (■) (SEQ ID NO: 48) or $G10_{208}$ (●) (SEQ ID NO: 49). FIG. 8C. Lysis by TIL660-1 of T2 cells incubated with $G9_{280}$ (■) (SEQ ID NO: 40). FIG. 8D. Lysis by TIL660-2 of T2 cells incubated with G10-5(■) (SEQ ID NO: 34).

DETAILED DESCRIPTION OF THE INVENTION

Figure 2A:
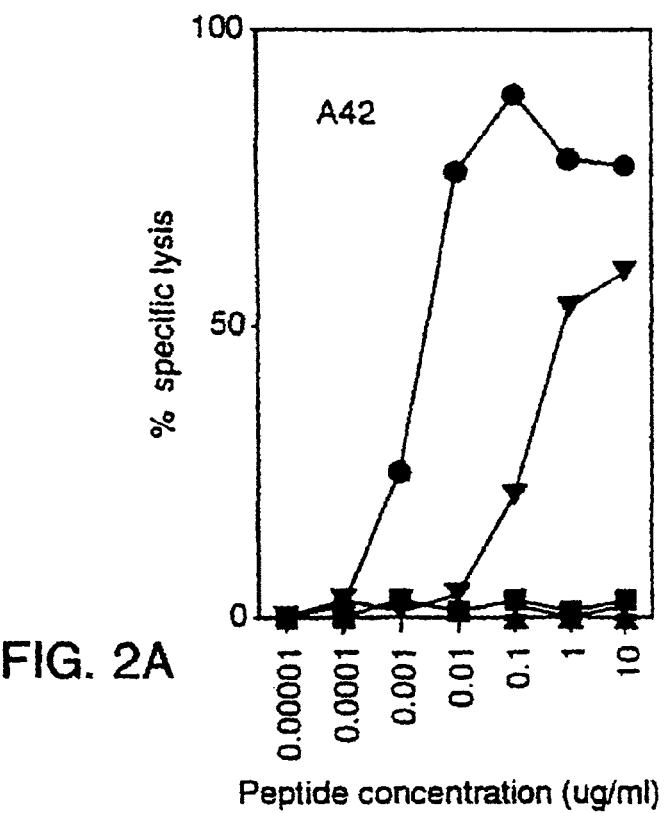
FIG. 2 shows titration of MART-1 peptides for recognition by TIL. T2 cells were incubated with varied concentrations of the purified MART-1 peptides, M9-1, M9-2, M9-3, M10-2, M10-3, M10-4 and M10-5, and lysis by TIL clone A42 or TIL line TIL1235 was measured by 4 h-$^{51}$Cr release cytotoxicity assay at an E (EFFECTOR):T (TARGET) ratio of 20:1 for A42 and 40:1 for TIL1235. Peptide M9-2 sensitized T2 cells at a concentration of 1 ng/ml. The purified peptide M10-4 was recognized by TIL1235, but not by A42. (M9-1 |-|, M9-2 ●-●, M9-3, ■-■, M10-2 ▲-▲, M10-3 ▼-▼, M10-4 ▮ -▮ , M10-5 +-+).

For the purpose of a more complete understanding of the invention, the following definitions are described herein. Nucleic acid sequences includes, but is not limited to, DNA, RNA or cDNA. Nucleic acid sequence as used herein refers to an isolated and purified nucleic acid sequence. MART-1 messenger RNA (mRNA) refers to one or more RNA transcripts which are a product of the MART-1 gene. Substantially homologous as used herein refers to substantial correspondence between the nucleic acid sequence of MART-1 shown in FIG. 1 (SEQ ID NO:1) and that of any other nucleic acid sequence. Substantially homologous means about 50-100% homologous homology, preferably by about 70-100% homology, and most preferably about 90-100% homology between the MART-1 sequence and that of any other nucleic acid sequence. In addition, substantially homologous as used herein also refers to substantial correspondences between the amino acid sequence of the MART-1 antigen shown in FIG. 1 (SEQ ID NO:2) and that of any other amino acid sequence.

Major Histocompatibility Complex (MHC) is a generic designation meant to encompass the histo-compatibility antigen systems described in different species including the human leucocyte antigens (HLA).

The term melanoma includes, but is not limited to, melanomas, metastatic melanomas, melanomas derived from either melanocytes or melanocytes related nevus cells, melanocarcinomas, melanoepitheliomas, melanosarcomas, melanoma in situ, superficial spreading melanoma, nodular melanoma, lentigo maligna melanoma, acral lentiginous melanoma, invasive melanoma or familial atypical mole and melanoma (FAM-M) syndrome. Such melanomas in mammals may be caused by, chromosomal abnormalities, degenerative growth and developmental disorders, mitogenic agents, ultraviolet radiation (UV), viral infections, inappropriate tissue expression of a gene, alterations in expression of a gene, or carcinogenic agents. The aforementioned melanomas can be diagnosed, assessed or treated by methods described in the present application.

By atypical mole we mean a mole with features that are abnormal and may be precancerous.

By melanoma antigen or immunogen we mean all or parts thereof of the MART-1 protein or peptides based on the MART-1 protein sequence capable of causing a cellular or humoral immune response in a mammal. Such antigens may also be reactive with antibodies from animals immunized with all, part or parts of the MART-1 protein (SEQ ID NO:2). Such a protein or peptide may be encoded by all or part of the MART-1 nucleic acid sequence of this invention.

By immunogenic peptide we mean a peptide derived from the MART-1 protein sequence (FIG. 1; SEQ ID NO. 2) or a gp100 protein sequence (FIG. 5A; SEQ ID NO: 27) capable of causing a cellular or humoral immune response in a mammal. Such peptides may be reactive with antibodies from an animal immunized with the peptides. Such peptides are about 5-20 amino acid in length preferably about 8 to 15 amino acids in length, and most preferably about 9-10 amino acids in length.

One skilled in the art will understand that the bioassays of the present invention may be used in the analysis of biological samples or tissues from any vertebrate species. In a preferred embodiment, mammalian biological samples or tissues are analyzed.

Tissue includes, but is not limited to, single cells, whole organs and portions thereof. Biological samples include, but are not limited to, tissues, primary cultures of mammalian tissues, biopsy specimens, pathology specimens, and necropsy specimens. Mammal includes but is not limited to, humans, monkeys, dogs, cats, mice, rats, pigs, cows, pigs, horses, sheep and goats.

The present invention provides a nucleic acid sequence which encodes a novel melanoma antigen recognized by T cells. This novel melanoma antigen designated MART-1 (melanoma antigen-recognized by T-Cells-1). MART-1 shows no significant homology to any known melanoma antigen and thus represents a new melanoma antigen. The MART-1 antigen contains a highly hydrophobic region from amino acids 27 to 47 (SEQ ID. NO:2) followed by three arginine residues, suggestive of a transmembrane protein. Although no significant homology exists to the entire protein there is a 27 amino acid segment (amino acids 57-83; SEQ ID. NO:2) that is 37% identical to a Type II membrane protein previously recognized as mouse natural killer cell surface protein NKR-P1 (Yokoyama, W. M., et al. (1991), *J. Immunol.* 147:3229-3236). MART-1 does not contain a leader sequence characteristic of many Type I membrane proteins (Singer, S. J. (1990) *Annu. Rev. Cell Biol.* 6: 247-296).

MART-1 RNA expression appears to be restricted to fresh and cultured melanoma and melanocyte cell lines and human retina; expression has not been found in any other fresh or cultured tissues or other tumor histologies tested. The cDNA sequence for MART-1 is shown in FIG. 1 (SEQ ID NO:1), the deduced amino acid sequence for the MART-1 protein is also shown in FIG. 1 (SEQ ID NO.:1).

The nucleic acid sequence for MART-1 shown in FIG. 1 (SEQ ID NO.:1), represents a preferred embodiment of the invention. It is, however, understood by one skilled in the art that due to the degeneracy of the genetic code variations in the cDNA sequence shown in FIG. 1 (SEQ ID NO.:1) will still result in a DNA sequence capable of encoding the MART-1 protein antigen. Such DNA sequences are therefore functionally equivalent to the sequence set forth in FIG. 1 (SEQ ID NO.:1) and are intended to be encompassed within the present invention. Further, a person of skill in the art will understand that there are naturally occurring allelic variations in a given species of the MART-1 nucleic acid sequence shown in FIG.

1 (SEQ ID NO.:1), these variations are also intended to be encompassed by the present invention.

The predicted MART-1 antigen is a 118 amino acid protein of about 13 (kd). This invention further includes MART-1 protein or peptides or analogs thereof having substantially the same function as the MART-1 antigen or protein of this invention. Such proteins or polypeptides include, but are not limited to, a fragment of the protein, or a substitution, addition or deletion mutant of the MART-1 protein. This invention also encompasses proteins or peptides that are substantially homologous to the MART-1 antigen. Substantially homologous means about 50-100% homology, preferably about 70-100% homology, and most preferably about 90-100% homology between the MART-1 and any another amino acid sequence or protein or peptide.

The term "analog" includes any polypeptide having an amino acid residue sequence substantially identical to the MART-1 sequence specifically shown herein (FIG. 1; SEQ ID NO: 1) in which one or more residues have been conservatively substituted with a functionally similar residue and which displays the functional aspects of the MART-1 antigen as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more residues chemically derivatized by reaction of a functional side group. Examples of such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those proteins or peptides which contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Proteins or polypeptides of the present invention also include any polypeptide having one or more additions and/or deletions or residues relative to the sequence of a polypeptide whose sequence is encoded is the DNA of MART-1, so long as the requisite activity is maintained.

This invention also provides a recombinant DNA molecule comprising all or part of the MART-1 nucleic acid sequence (SEQ. ID NO.:1) and a vector. Expression vectors suitable for use in the present invention may comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast promoters and promoters derived from polyoma, adenovirus, retrovirus or SV40. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology", John Wiley and Sons, New York, N.Y.) or commercially available.

Another aspect of this invention relates to a host organism into which recombinant expression vector containing all or part of the MART-1 nucleic acid sequence has been inserted. The host cells transformed with the MART-1 nucleic acid sequence of this invention include eukaryotes, such as animal, plant, insect and yeast cells and prokaryotes, such as E. coli. The means by which the vector carrying the gene may be introduced into the cell include, but are not limited to, microinjection, electroporation, transduction, or transfection using DEAE-dextran, lipofection, calcium phosphate or other procedures known to one skilled in the art (Sambrook et al. (1989) in "Molecular Cloning. A Laboratory Manual", Cold Spring Harbor Press, Plainview, N.Y.).

In a preferred embodiment, eukaryotic expression vectors that function in eukaryotic cells are used. Examples of such vectors include, but are not limited to, retroviral vectors, vaccinia virus vectors, adenovirus vectors, herpes virus vector, fowl pox virus vector, bacterial expression vectors, plasmids, such as pcDNA3 (Invitrogen, San Diego, Calif.) or the baculovirus transfer vectors. Preferred eukaryotic cell lines include, but are not limited to, COS cells, CHO cells, HeLa cells, NIH/3T3 cells, 293 cells (ATCC#CRL1573), T2 cells, dendritic cells, or monocytes. In a particularly preferred embodiment the recombinant MART-1 protein expression vector is introduced into mammalian cells, such as NIH/3T3, COS, CHO, 293 cells (ATCC #CRL 1573), T2 cells, dendritic cells, or monocytes to ensure proper processing and modification of the MART-1 protein. In an alternative embodiment the MART-1 cDNA is introduced into COS7 (Gluzman, Y. et al. (1981) Cell 23: 175-182). The choice of an appropriate cell is within the skill of a person in the art.

In one embodiment the expressed recombinant MART-1 protein may be detected by methods known in the art which include Coomassie blue staining and Western blotting using antibodies specific for the MART-1 protein.

In a further embodiment, the recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the MART-1 protein (Ausubel et. al., (1987) in "Current Protocols in Molecular Biology" John Wiley and Sons, New York, N.Y.).

The nucleic acid sequence or portions thereof, of this invention are useful as probes for the detection of expression of the MART-1 gene in normal and diseased tissue. Therefore, another aspect of the present invention relates to a bioassay for detecting messenger RNA encoding the MART-1 protein in a biological sample comprising the steps of (a) contacting all or part of the nucleic acid sequence of this invention with said biological sample under conditions allowing a complex to form between said nucleic acid sequence and said messenger RNA, (b) detecting said complexes and, (c) determining the level of said messenger RNA.

RNA can be isolated as whole cell RNA or as poly(A)$^+$ RNA. Whole cell RNA can be isolated by a variety of methods known to those skilled in the art. (Ausubel et al., (1987) on "Current Protocols in Molecular Biology", John Wiley and Sons, New York). Such methods include extraction of RNA by differential precipitation (Birnboim, H. C. (1988) *Nucleic Acids Res.*, 16:1487-1497), extraction of RNA by organic solvents (Chomczynski, P. et al. (1987) *Anal. Biochem.*, 162: 156-159) and the extraction of RNA with strong denaturants (Chirgwin, J. M. et al. (1979) *Biochemistry*, 18:5294-5299). Poly(A)$^+$ RNA can be selected from whole cell RNA by affinity chromatography on oligo-d(T) columns (Aviv, H. et al. (1972) *Proc. Natl. Acad. Sci.*, 69:1408-1412). Examples of methods for determining cellular messenger mRNA levels for step (c) include, but are not limited to Northern blotting (Alwine, J. C. et al. (1977) *Proc. Natl. Acad. Sci.*, 74:5350-5354), dot and slot hybridization (Kafatos, F. C. et al. (1979) *Nucleic Acids Res.*, 7:1541-1522), filter hybridization (Hollander, M. C. et al. (1990) *Biotechniques;* 9:174-179), RNase protection (Sambrook et. al., (1989) in "Molecular Cloning, A Laboratory Manual", Cold Spring Harbor Press, Plainview, N.Y.), polymerase chain reaction (Watson, J. D. et al. (1992) in "Recombinant DNA" Second Edition, W. H. Freeman and Company, New York) and nuclear run-off assays (Ausubel et. al., (1987) in "Current Protocols in Molecular Biology" Supplement 9 (1990); John Wiley and Sons, New York, N.Y.).

Detection of complexes in Step (b) of the bioassay can also be carried out by a variety of techniques. Detection of the complexes by signal amplification can be achieved by several conventional labelling techniques including radiolabels and enzymes (Sambrook et. al., (1983) in "Molecular Cloning, A Laboratory Manual", Cold Spring Harbor Press, Plainview, N.Y.; Ausubel et al., (1987) in "Current Protocols in Molecular Biology, John Wiley and Sons, New York N.Y.). Radiolabelling kits are also commercially available. The MART-1 nucleic acid sequence used as a probe in step(c) of the bioassay may be RNA or DNA. Preferred methods of labelling the DNA sequences are with $^{32}$P using Klenow enzyme or polynucleotide kinase. Preferred methods of labeling RNA or riboprobe sequences are with $^{32}$P or $^{35}$S using RNA polymerases. In addition, there are known non-radioactive techniques for signal amplification including methods for attaching chemical moieties to pyrimidine and purine rings (Dale, R. N. K. et al. (1973) *Proc. Natl. Acad. Sci.*, 70:2238-2242; Heck, R. F. (1968) *S. Am. Chem. Soc.*, 90:5518-5523), methods which allow detection by chemiluminescence (Barton, S. K. et al. (1992) *J. Am. Chem. Soc.*, 114:8736-8740) and methods utilizing biotinylated nucleic acid probes (Johnson, T. K. et al. (1983) *Anal. Biochem.*, 133:125-131; Erickson, P. F. et al. (1982) *J. of Immunology Methods*, 51:241-249; Matthaei, F. S. et al (1986) *Anal. Biochem.*, 157:123-128) and methods which allow detection by fluorescence using commercially available products. Non-radioactive labelling kits are also commercially available.

Examples of biological samples that can be used in this bioassay include, but are not limited to, primary mammalian cultures, continuous mammalian cell lines, such as melanocyte cell lines, mammalian organs such as skin or retina, tissues, biopsy specimens, neoplasms, pathology specimens, and necropsy specimens.

In a preferred embodiment, a $^{32}$P radiolabelled MART-1 probe, as exemplified in Example 1, is used. Preferably the MART-1 probe is the full length cDNA in FIG. 1 (SEQ ID NO:1). The approximately 1.6 Kilobase (kb) cDNA (FIG. 1; SEQ ID NO:1) was cloned into the vector and the resulting plasmid deposited with the American Type Culture Collection (ATCC) 12301 Parklawn Drive, Rockville, Md. 20852 USA on Apr. 14, 1994, and given ATCC Deposit Number 75738. The full length MART-1 nucleic acid sequence can be isolated from the pCRII plasmid by digestion with HINDIII and XhoI restriction enzymes. This 1.6 kb nucleic acid sequence can then be used as a probe. This probe is used to detect MART-1 mRNA in total RNA or poly A$^+$ RNA isolated from a variety of tissues or biological samples.

In another embodiment, combinations of oligonucleotide pairs based on the MART-1 sequence in FIG. 1 (SEQ ID NO.:1) are used as Polymerase Chain Reaction (PCR) primers to detect MART-1 mRNA in a biological sample. These primers can be used in a method following the reverse transcriptase-Polymerase Chain Reaction (RT-PCR) process for amplifying selected RNA nucleic acid sequences as detailed in Ausubel et al., (eds) (1987) In "Current Protocols in Molecular Biology" Chapter 15, John Wiley and Sons, New York, N.Y. The oligonucleotides can be synthesized by automated instruments sold by a variety of manufacturers or can be commercially prepared based upon the nucleic acid sequence of this invention. One skilled in the art will know how to select PCR primers based on the MART-1 nucleic acid sequence for amplifying MART-1 RNA in a sample.

The MART-1 nucleic acid sequence or portions thereof (FIG. 1: SEQ ID NO:1) of this invention are useful to detect alterations of the MART-1 gene in normal or diseased mammalian tissue. By alteration, we mean additions, deletions, substitutions or duplications in the MART-1 gene sequence or gene amplification of the MART-1 gene sequence. Therefore, another aspect of the present invention relates to an assay for detecting alterations of the MART-1 gene in a biological sample comprising the steps of (a) contacting all or part of the nucleic acid sequence of this invention with genomic DNA isolated from a biological sample under conditions allowing a complex to form between said nucleic acid sequence and said genomic DNA, (b) detecting said complexes, and (c) determining alterations in said MART-1 gene by comparison to a control sample.

Standard methods for isolating DNA from a biological sample, detecting alterations in a gene and detecting complex between the MART-1 nucleic acid probe and genomic DNA sequences are provided in manuals such as Sambrook et al., (eds) (1989) "Molecular Cloning, A Laboratory Mineral", Cold Spring Harbor Press, Plainview, N.Y. and in Ausubel et al., (eds) (1987) in "Current Protocols in Molecular Biology" John Wiley and Sons, New York, N.Y.

The MART-1 nucleic acid sequences of this invention (FIG. 1; SEQ ID No:1) can also be used as probes to isolate the MART-1 homologs in other species. In a preferred embodiment the MART-1 cDNA (FIG. 1; SEQ ID No:1) is used to screen a mammalian cDNA library, positive clones are selected and sequenced. Examples of tissue sources from which the cDNA library can be synthesized include, but are not limited to skin, retina, melanocytes, neonatal skin and embryos. Preferably a melanoma library is screened using the MART-1 cDNA as a probe (FIG. 1; SEQ ID No. 1). One skilled in the art will understand the appropriate hybridization conditions to be used to detect the homologs. Conventional methods for nucleic acid hybridization, construction of libraries and cloning techniques are described in Sambrook et al., (eds) (1989) In "Molecular Cloning A Laboratory Manual" Cold Spring Harbor Press, Plainview, N.Y. and Ausubel et al., (eds) in "Current Protocols in Molecular Biology" (1987), John Wiley and Sons, New York, N.Y.

It is known that all or parts thereof of the MART-1 protein is an antigen present on melanoma cells. It is therefore another aspect of this invention to provide MART-1 nucleic acid probes to be utilized in detecting MART-1 RNA or alterations in the level of MART-1 mRNA in biological sample isolated from a mammal afflicted with a disease. Examples of such diseases, include but are not limited to, melanomas. By alterations in the level of MART-1 mRNA we mean an increase or decrease in the level of an RNA relative to a control sample or the appearance or disappearance of the MART-1 mRNA relative to a control sample. Detection in the alterations of MART-1 mRNA will allow for diagnosis or the assessment of the diseased state. Therefore, alterations in the level of MART-1 mRNA may be predictive of the prognosis for the afflicted mammal.

In another embodiment the nucleic acid of this invention can be used in in situ hybridization on mammalian tissues to determine the precise site or subcellular site of expression of the MART-1 gene within a tissue. A preferred method of labeling the MART-1 nucleic acid sequence is synthesizing a $^{35}$S-labeled RNA probe by in vitro transcription utilizing SP6 polymerase. In the MART-1 plasmid (ATCC Deposit #75738) the sense strand is under the control of the T7 promoter, the antisense strand is under the SP6 promoter. It is preferable that the probe be hydrolyzed to a probe length of approximately 400-200 base pairs. Conventional methods for preparation of tissues for in situ, synthesis of probes and detection of signal can be found in Ausubel et. al., (eds) (1987) in "Current Protocols in Molecular Biology," John Wiley and Sons, New York, N.Y. Chapter 14 and Vander Ploeg, M., Raap A. K. (1988) In "New Frontiers in Cytology" Goerttler, K., Feichter, G E, Witte. S. (eds) pp 13-21 Springer-Verlag, New York. The probe is then contacted with mammalian tissue sections and in situ analyses performed by conventional methods. Examples of tissues that can be used include, but are not limited to, mammalian embryos, adult mammalian tissues, such as skin, lymph nodes and retina, biopsy specimens, pathology specimens and necropsy specimens. In a preferred embodiment, MART-1 in situ probes may be used to evaluate MART-1 RNA expression in diseased tissue for invasive early melanoma to characterize radial and vertical growth phases of the melanoma lesion and assess the margins of the disease within the tissue.

In yet another embodiment of this invention all or parts thereof of the MART-1 (SEQ ID NO:1) nucleic acid sequence can be used to generate transgenic animals. Preferably the MART-1 gene is introduced into an animal or an ancestor of the animal at an embryonic stage, preferably at the one cell stage and generally not later than about the eight cell stage. There are several means by which transgenic animals carrying a MART-1 gene can be made. One method involves the use of retroviruses carrying all or part of the MART-1 sequence. The retroviruses containing the transgene are introduced into the embryonic animal by transfection. Another methods involves directly injecting the transgene into the embryo. Yet another methods employs the embryonic stem cell method or homologous recombination method known to workers in the field. Examples of animals into which the MART-1 transgene can be introduced include but are not limited to, primates, mice, rats or other rodents. Such transgenic animals may be useful as biological models for the study of melanoma and to evaluate diagnostic or therapeutic methods for melanoma.

This invention further comprises an antibody or antibodies reactive with the MART-1 protein or peptides or modified peptides or analogs thereof having the amino acid sequence defined in FIG. 1 (SEQ ID NO: 2) or a unique portion thereof. In this embodiment of the invention the antibodies are monoclonal or polyclonal in origin. MART-1 protein or peptides used to generate the antibodies may be from natural or recombinant sources or generated by chemical synthesis. Natural MART-1 proteins can be isolated from mammalian biological samples. Biological samples include, but are not limited to mammalian tissues such as fresh melanoma, skin, retina, primary or continuous cultures of mammalian cells such as melanoma cultures or cultured melanocytes. The natural MART-1 proteins may be isolated by the same methods described above for recombinant proteins. Recombinant MART-1 proteins or peptides may be produced and purified by conventional methods. Synthetic MART-1 peptides may be custom ordered or commercially made based on the predicted amino acid sequence of the present invention (FIG. 1; SEQ ID:2) or synthesized by methods known to one skilled in the art (Merrifield, R. B. (1963) *J. Amer. Soc.* 85:2149). Examples of MART-1 peptides include, but are not limited to, are AAGIGILTV (M9-2; SEQ. ID NO. 4), EAAGIGILTV (M10-3; SEQ. ID NO. 17) and AAGIGILTVI (M10-4; SEQ. ID NO. 18) (peptides are presented in single letter amino acid code). The most preferred peptide is AAGIGILTV (SEQ ID NO:4).

Alternatively, peptides derived form the MART-1 protein sequence may modified to increase their immunogenicity by enhancing binding of the peptide to the MHC molecules in which the peptide is presented. Examples of such modified MART-1 peptides that may used are shown, but not limited to, the peptides in Table 14. In a preferred embodiment the MART-1 peptide that is modified to enhance its binding to MHC Class I molecules is AAGIGILTV (SEQ ID NO:4). By way of example, the modified peptides ALGIGILTV (M9-2-2L), WAGIGILTV (M9-2-1W), FAGIGILTV (M9-2-1F) and AAYIGILTV (M9-2-3Y). The peptide or modified peptide may be conjugated to a carrier molecule to enhance the antigenicity of the peptide. Examples of carrier molecules, include, but are not limited to, human albumin, bovine albumin, lipoprotein and keyhole limpet hemo-cyanin ("Basic and Clinical Immunology" (1991) Stites, D. P. and Terr A. I. (eds) Appleton and Lange, Norwalk Connecticut, San Mateo, Calif.).

Exemplary antibody molecules for use in the detection methods of the present invention are intact immunoglobulin molecules, substantially intact immunoglobulin molecules or those portions of an immunoglobulin molecule that contain the antigen binding site, including those portions of immunoglobulin molecules known in the art as F(ab), F(ab'); F(ab)$_2$ and F(v). Polyclonal or monoclonal antibodies may be produced by methods known in the art. (Kohler and Milstein (1975) *Nature* 256, 495-497; Campbell "Monoclonal Antibody Technology, the Production and Characterization of Rodent and Human Hybridomas" in Burdon et al. (eds.) (1985) "Laboratory Techniques in Biochemistry and Molecular Biology," Volume 13, Elsevier Science Publishers, Amsterdam). The antibodies or antigen binding fragments may also be produced by genetic engineering. The technology for expression of both heavy and light chain genes in *E. coli* is the subject of the PCT patent applications: publication number WO 901443, WO 901443 and WO 9014424 and in Huse et al. (1989) *Science* 246:1275-1281.

The antibodies of this invention may react with native or denatured MART-1 protein, peptides or analogs thereof, or modified peptides an analogs thereof. The specific immunoassay in which the antibodies are to be used will dictate which antibodies are desirable. Antibodies may be raised against the MART-1 protein or portions thereof or against synthetic peptides homologous to the MART-1 amino acid sequence.

In one embodiment the antibodies of this invention are used in immunoassays to detect the novel MART-1 protein in biological samples. In this method the antibodies of the present invention are contacted with a biological sample and the formation of a complex between the MART-1 antigen and antibody is detected. Immunoassays of the present invention may be radioimmunoassay, Western blot assay, immunofluorescent assay, enzyme immunoassay, chemiluminescent assay, immunohistochemical assay and the like. (In "Principles and Practice of Immunoassay" (1991) Christopher P. Price and David J. Neoman (eds), Stockton Press, New York, N.Y.; Ausubel et al. (eds) (1987) in "Current Protocols in Molecular Biology" John Wiley and Sons, New York, N.Y.). Standard techniques known in the art for ELISA are described in *Methods in Immunodiagnosis,* 2nd Edition, Rose and Bigazzi, eds., John Wiley and Sons, New York 1980 and Campbell et al., *Methods of Immunology,* W. A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Pres, NY, N.Y.; Oellirich, M. 1984. *J. Clin. Chem. Clin. Biochem.* 22: 895-904) Biological samples appropriate for such detection assays include mammalian tissues, melanoma and melanocyte cell lines, skin, retina, lymph nodes, pathology specimens, necropsy specimens, and biopsy specimens. Proteins may be isolated from biological samples by conventional methods described in (Ausubel et al., (eds) (1987) in "Current Protocols in Molecular Biology" John Wiley and Sons, New York, N.Y.).

The antibodies of this invention can therefore be used in immunoassays to detect MART-1 antigen or alteration in the level of expression of the MART-1 antigen in biological samples isolated from mammals afflicted with a disease or disorder. Examples of biological samples include, but are not limited to, mammalian tissues, biopsy tissue samples, melanoma and lymph node biopsy samples, pathology and tissue samples. Examples of diseases that can be assessed by these immunoassays, include, but are not limited to, melanomas and tissues which are secondary sites for melanoma metastasis. By alteration in level of expression, we mean an increase or decrease of the MART protein or portions thereof relative to a control sample. Alteration is also meant to encompass substitution, deletion or addition mutants of the MART-1 protein. Such mutations can be determined by using the antibodies of this invention known to react with specific epitopes of the MART-1 protein and determining which epitopes are present relative to a control. The antibodies of this invention can therefore be used in an immunoassay to diagnose, assess or prognoses a mammal afflicted with the disease.

In a preferred embodiment, the MART-1 antibodies of this invention are used to assess the presence of the MART-1 antigen from a tissue biopsy of a mammal afflicted with melanoma using immunocytochemistry. Such assessment of the delineation of the MART-1 antigen in a diseased tissue can be used to prognose the progression of the disease in a mammal afflicted with the disease. Specifically the MART-1 antibodies can be used to characterize the radial and vertical growth phases of the melanoma lesion. Conventional methods for immunohistochemistry are described in (Harlow and Lane (eds) (1988) In "Antibodies A Laboratory Manual", Cold Spinning Harbor Press, Cold Spring Harbor, N.Y.; Ausbel et al. (eds) (1987). In Current Protocols In Molecular Biology John Wiley and Sons (New York, N.Y.).

In another embodiment, antibodies of this invention may be used to purify the MART-1 protein or portions thereof. Immunoaffinity chromatography can be performed by conventional methods known to one skilled in the art (Ausubel et al. (eds) (1987) in "Current Protocols in Molecular Biology" John Wiley and Sons, New York, N.Y.).

In another preferred embodiment rabbit antisera containing antibodies which specifically recognize the MART-1 protein is used to detect said protein in Western Blot Analysis. Such antisera is directed to all, or a part or parts of the MART-1 protein or synthetic peptides derived from the MART-1 protein sequence. Preferably a MART-1 synthetic peptide derived from the MART-1 predicted amino acid sequence is used (FIG. 1; SEQ ID NO:2). Alternatively, modified MART-1 peptides may be used. The peptide is synthesized by standard methods on an automated peptide synthesizer and purified by high pressure liquid chromatography (HPLC) as described in Example 2. The purified peptide may be conjugated to a carrier as described in (M. Bodanszky (1984) "Principles of Peptide Synthesis," Springer Verlag, New York, N.Y.). Using conventional methods, rabbits may be immunized with the MART-1 protein or peptide conjugated to carriers. Preferably about 0.1 to about 10 (mg) of antigen in adjuvant may be used, most preferably about 1 mg of antigen in adjuvant may be used. The animal receives similar booster doses and antisera titer is assessed by ELISA assay. Satisfactory levels of antisera are obtained when the anti-peptide antibody titer reaches a plateau. This antibody can be used in the standard immunoassays described above.

T-lymphocytes recognize antigen in association with Class I or Class II MHC molecules in the form of a peptide fragment bound to an MHC molecule. The degree of peptide binding to a given MHC allele is based on amino acids at particular positions within the peptide (Parker et al. (1992) *Journal of Immunology* 149:3580; Kubo, et al. (1994) *Journal of Immunology* 52:3913-3924; Ruppert J. et al. (1993) *Cell* 74:929-937; Falk et al. (1991) *Nature* 351:290-296, each of which is herein incorporated by reference). Therefore, another embodiment of this invention relates to peptides derived from the MART-1 protein sequence (FIG. 1; SEQ ID NO:2) which have been modified to increase immunogenicity by enhancing binding of the peptide to the MHC molecule with which the peptide is associated. By way of example, modification may include substitution, deletion or addition of an amino acid in the given-immunogenic peptide sequence or mutation of existing amino acids within the given immunogenic peptide sequence, or derivatization of existing amino acids within the given immunogenic peptide sequence. Any amino acid comprising the immunogenic peptide sequence may be modified in accordance with this invention. In a preferred embodiment at least one amino acid is substituted or replaced within the given immunogenic peptide sequence. Any amino acid may be used to substitute or replace a given amino acid within the immunogenic peptide sequence. Modified peptides are intended to include any immunogenic MART-1 peptide which has been modified and exhibits enhanced binding to the MHC molecule with which it associates when presented to the T-cell.

By way of example, the HLA-A2 allele binds peptides of nine or ten amino acids. Examples of positions within the peptide that may be altered to enhance binding include, but are not limited to, the first position, the second position, the third position and the last position of the peptide. Any amino acid may be used to substitute or replace these positions within the immunogenic peptide sequence. For enhanced binding to HLA-A2 the amino acid at the second position of the peptide is preferably a hydrophobia aliphatic amino acid. Examples or amino acids that may be used at the second position include, but are not limited to, leucine, methionine, alanine, isoleucine, valine, threonine or glycine. Preferably leucine or methionine is found at the second position of the peptide. The last amino acid of the peptide (either the 9th or 10th amino acid depending on the length of the peptide) is preferably a hydrophobic aliphatic amino acid. Examples of amino acids that may be used in the last position of the peptide include, but are not limited to, valine, methionine, leucine, alanine, isoleucine, threonine or glycine. Preferably valine is found at the last position in the peptide. The amino acids at the first and third positions in the peptide may also be modified to enhance binding of the peptide to the MHC Class I molecule. The amino acids at the first and third positions in the peptide may be any amino acid. Preferably, the amino acids at the first and third positions are hydrophobic aliphatic amino acids or aromatic amino acids. Examples of amino acids that maybe used at these positions include, but are not limited to, leucine, methionine, valine, alanine, isoleucine, threonine, glycine, tryptophan, phenylalanine, tyrosine, serine, aspartic acid, or lysine. Examples of MART-1 peptides that may be modified include, but are not limited to, AAGIGILTV (SEQ ID NO: 4), EAAGIGILTV (SEQ ID NO: 17) and AAGIGILTVI (SEQ ID NO: 18) (peptides are presented in single letter amino acid code). By way of example the immunogenic MART-1 peptide AAGIGILTV (SEQ ID NO:4) may be modified according to the following formula $X_1X_2X_3IGILTX_4$ wherein $X_1$ may be any amino acid, preferably any hydrophobic aliphatic amino acid, or aromatic amino acid. Examples of amino acids that may be used, but are not limited to, alanine, tryptophan, phenylalanine, tyrosine, lysine, isoleucine, leucine, methionine, threonine, glycine or serine.

$X_2$ may be any hydrophobic amino acid, preferably an aliphatic hydrophobic amino acids. Examples of amino acids that may be used include, but are not limited to, leucine, methionine, isoleucine, valine, threonine, alanine or glycine.

$X_3$ may be any amino acid, preferably any hydrophobic aliphatic amino acid, or aromatic amino acid. Examples of amino acids that may be used include, but are not limited to, tryptophan, phenylalanine, tyrosine, lysine, aspartic acid, serine, alanine, glycine, isoleucine, valine, or threonine.

$X_4$ may be any hydropbic amino acid, preferably a hydrophobic aliphatic amino acid. Examples of amino acids that may be used include, but are not limited to, valine, leucine, isoleucine, alanine, threonine, or glycine.

Examples of modified AAGIGILTV (SEQ ID NO:4) peptide sequences that may be produced are shown but not limited to the peptides in Table 14 (Example 5).

This invention further includes analogs of these immunogenic modified peptides derived from the MART-1 amino acid sequence (FIG. 1; SEQ ID NO:2) which have been modified. The term analog is intended to include any peptide which displays the functional aspects of these modified peptides. The term analog also includes conservative substitutions or chemical derivatives of these modified peptides as described above. These modified peptides may be synthetically or recombinantly produced by conventional methods.

The recombinant or natural MART-1 protein, peptides, or analogs thereof, or modified MART-1 peptides, or analogs thereof may be used as a vaccine either prophylactically or therapeutically. When provided prophylactically the vaccine is provided in advance of any evidence of melanoma. The prophylactic administration of the MART-1 vaccine should serve to prevent or attenuate melanoma in a mammal. In a preferred embodiment mammals, preferably human, at high risk for melanoma are prophylactically treated with the vaccines of this invention. Examples of such mammals include, but are not limited to, humans with a family history of melanoma, humans with a history of atypical moles, humans with a history of FAM-M syndrome or humans afflicted with melanoma previously resected and therefore at risk for reoccurrence. When provided therapeutically, the vaccine is provided to enhance the patient's own immune response to the tumor antigen present on the melanoma or metastatic melanoma. The vaccine, which acts as an immunogen, may be a cell, cell lysate from cells transfected with a recombinant expression vector, cell lysates from cells transfected with a MART-1 recombinant expression vector, or a culture supernatant containing the expressed protein. Alternatively, the immunogen is a partially or substantially purified recombinant MART-1 protein, peptide or analog thereof or modified peptides or analogs thereof. The proteins or peptides may be conjugated with lipoprotein or administered in liposomal form or with adjuvant.

While it is possible for the immunogen to be administered in a pure or substantially pure form, it is preferable to present it as a pharmaceutical composition, formulation or preparation.

The formulations of the present invention, both for veterinary and for human use, comprise an immunogen as described above, together with one or more pharmaceutically acceptable carriers and, optionally, other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well-known in the pharmaceutical art.

All methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous intramuscular, subcutaneous, or intraperitoneal administration conveniently comprise sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1-2.0M), glycine, and the like, and having a buffered pH compatible with physiological conditions to produce an aqueous solution, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharides, amino acids, inorganic acids, and organic acids which may be used either on their own or as admixtures. These stabilizers are preferably incorporated in an amount of 0.11-10,000 parts by weight per part by weight of immunogen. If two or more stabilizers are to be used, their total amount is preferably within the range specified above. These stabilizers are used in aqueous solutions at the appropriate concentration and pH. The specific osmotic pressure of such aqueous solutions is generally in the range of 0.1-3.0 osmoles, preferably in the range of 0.8-1.2. The pH of the aqueous solution is adjusted to be within the range of 5.0-9.0, preferably within the range of 6-8. In formulating the immunogen of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the MART-1 protein, peptides and analogs thereof into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly(methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined With typical carriers, such as lactose, sucrose, starch, talc magnesium stearate, crystalline cellulose, methyl cellulose, carboxymethyl cellulose, glycerin, sodium alginate or gum arabic among others.

The proteins of the present invention may be supplied in the form of a kit, alone, or in the form of a pharmaceutical composition as described above.

Vaccination can be conducted by conventional methods. For example, the immunogen can be used in a suitable diluent such as saline or water, or complete or incomplete adjuvants. Further, the immunogen may or may not be bound to a carrier to make the protein immunogenic. Examples of such carrier molecules include but are not limited to bovine serum albumin (BSA), keyhole limpet hemocyanin (KLH), tetanus toxoid, and the like. The immunogen also may be coupled with lipoproteins or administered in liposomal form or with adjuvants. The immunogen can be administered by any route-appropriate for antibody production such as intravenous, intraperitoneal, intramuscular, subcutaneous, and the like. The immunogen may be administered once or at periodic intervals until a significant titer of anti-MART-1 immune cells or anti-MART-1 antibody is produced. The presence of anti-MART-1 immune cells may be assessed by measuring the frequency of precursor CTL (cytoxic T-lymphocytes) against MART-1 antigen prior to and after immunization by a CTL precursor analysis assay (Coulie, P. et al., (1992) *International Journal Of Cancer* 50:289-297). The antibody may be detected in the serum using the immunoassay described above.

The administration of the vaccine or immunogen of the present invention may be for either a prophylactic or therapeutic purpose. When provided prophylactically, the immunogen is provided in advance of any evidence or in advance of any symptom due to melanoma. The prophylactic administration of the immunogen serves to prevent or attenuate melanoma in a mammal. When provided therapeutically, the immunogen is provided at (or shortly after) the onset of the disease or at the onset of any symptom of the disease. The therapeutic administration of the immunogen serves to attenuate the disease.

A preferred embodiment is a vaccine prepared using recombinant MART-1 protein or peptide expression vectors. To provide a vaccine to an individual a genetic sequence which encodes for all or part of the MART-1 nucleic acid sequence is inserted into a expression vector, as described above, and introduced into the mammal to be immunized. Examples of vectors that may be used in the aforementioned vaccines include, but are not limited to, defective retroviral vectors, adenoviral vectors vaccinia viral vectors, fowl pox viral vectors, or other viral vectors (Mulligan, R. C., (1993) *Science* 260:926-932). The viral vectors carrying all or part of the MART-1 nucleic sequence can be introduced into a mammal either prior to any evidence of melanoma or to mediate regression of the disease in a mammal afflicted with melanoma. Examples of methods for administering the viral vector into the mammals include, but are not limited to, exposure of cells to the virus ex vivo, or injection of the retrovirus or a producer cell line of the virus into the affected tissue or intravenous administration of the virus. Alternatively the viral vector carrying all or part of the MART-1 nucleic acid sequence may be administered locally by direct injection into the melanoma lesion or topical application in a pharmaceutically acceptable carrier. The quantity of viral vector, carrying all or part of the MART-1 nucleic acid sequence, to be administered is based on the titer of virus particles. A preferred range of the immunogen to be administered may be about $10^6$ to about $10^{11}$ virus particles per mammal, preferably a human. After immunization the efficacy of the vaccine can be assessed by production of antibodies or immune cells that recognize the antigen, as assessed by specific lytic activity or specific cytokine production or by tumor regression. One skilled in the art would know the conventional methods to assess the aforementioned parameters. If the mammal to be immunized is already afflicted with melanoma or metastatic melanoma the vaccine can be administered in conjunction with other therapeutic treatments. Examples of other therapeutic treatments includes, but are not limited to, adoptive T cell immunotherapy, coadministration of cytokines or other therapeutic drugs for melanoma.

Alternatively all or parts thereof of a substantially or partially purified the MART-1 protein may be administered as a vaccine in a pharmaceutically acceptable carrier. Ranges of MART-1 protein that may be administered are about 0.001 to about 100 mg per patient, preferred doses are about 0.01 to about 100 mg per patient. In a preferred embodiment, the MART-1 peptide AAGIGILTV (SEQ. ID NO. 4) (presented in single letter code) or analogs thereof is administered therapeutically or prophylactically to a mammal in need of such treatment. Alternatively, modified MART-1 peptides, examples of which are presented in Table 14 may be used. Preferred doses may be about 0.001 mg to about 100 mg, most preferred are about 0.01 mg to about 100 mg. The peptide may be synthetically or recombinantly produced. Immunization is repeated as necessary, until a sufficient titer of anti-immunogen antibody or immune cells has been obtained.

In yet another alternative embodiment a viral vector, such as a retroviral vector, can be introduced into mammalian cells. Examples of mammalian cells into which the retroviral vector can be introduced include, but are not limited to, primary mammalian cultures or continuous mammalian cultures, COS cells, NIH3T3, or 293 cells (ATTC #CRL 1573). The means by which the vector carrying the gene may be introduced into a cell includes, but is not limited to, microinjection, electroporation, transfection or transfection using DEAE dextran, lipofection, calcium phosphate or other procedures known to one skilled in the art (Sambrook et al. (EDS) (1989) in "Molecular Cloning. A laboratory manual", Cold Spring Harbor Press Plainview, N.Y.). The mammalian cells expressing the MART-1 antigen can be administered to mammals and serve as a vaccine or immunogen. Examples of how the cells expressing MART-1 antigens can be administered include, but is not limited to, intravenous, intraperitoneal or intralesional. In a preferred embodiment, the part of the MART-1 nucleic acid sequence corresponding to the peptide AAGIGILTV (SEQ ID NO: 4) is inserted into the MART-1 expression vector and introduced into the mammalian cells. Alternatively, a nucleic acid sequence corresponding to MART-1 peptides which have been modified to enhance their binding to MHC molecules may be used. By way of example, the nucleic acid sequences encoding the modified peptides shown in Table 14 may be inserted into an expressions vector and introduced with mammalian cells.

The vaccine formulation of the present invention comprise an immunogen that induces an immune response directed against the melanoma associated antigens such as the melanoma associated MART-1 antigen. The vaccine formulations may be evaluated first in animal models, initially rodents, and in nonhuman primates and finally in humans. The safety of the immunization procedures is determined by looking for the effect of immunization on the general health of the immunized animal (weight change, fever, appetite behavior etc.) and looking for pathological changes on autopsies. After initial testing in animals, melanoma cancer patients can be tested. Conventional methods would be used to evaluate the immune response of the patient to determine the efficiency of the vaccine.

In yet another embodiment of this invention all, part, or parts of the MART-1 protein or MART-1 peptides or analogs thereof, or modified MART-1 peptides or analogs thereof, may be exposed to dendritic cells cultured in vitro. The cultured dendritic cells provide a means of producing T-cell dependent antigens comprised of dendritic cell modified antigen or dendritic cells pulsed with antigen, in which the antigen is processed and expressed on the antigen activated dendritic cell. The MART-1 antigen activated dendritic cells or processed dendritic cell antigens may be used as immunogens for vaccines or for the treatment of melanoma. The dendritic cells should be exposed to antigen for sufficient time to allow the antigens to be internalized and presented on the dendritic cells surface. The resulting dendritic cells or the dendritic cell process antigens can than be administered to an individual in need of therapy. Such methods are described in Steinman et al. (WO93/208185) and in Banchereau et al. (EPO Application 0563485A1) which are incorporated herein by reference.

In yet another embodiment of this invention T-cells isolated from individuals can be exposed to the MART-1 protein or portions thereof, or MART-1 peptides or analogs thereof or MART-1 modified peptides or analogs thereof in vitro and then administered to a patient in need of such treatment in a therapeutically effective amount. Examples of where T-lymphocytes can be isolated, include but are not limited to, peripheral blood cells lymphocytes (PBL), lymph nodes, or tumor infiltrating lymphocytes (TIL). Such lymphocytes can be isolated from the individual to be treated or from a donor by methods known in the art and cultured in vitro (Kawakami, Y. et al. (1989) *J. Immunol.* 142: 2453-3461). Lymphocytes are cultured in media such as RPMI or RPMI 1640 or AIM V for 1-10 weeks. Viability is assessed by trypan blue dye exclusion assay. The lymphocytes are exposed to all or part of the MART-1 protein for part or all of the culture duration. In a preferred embodiment the lymphocytes are exposed to the AAGIGILTV (SEQ ID NO: 4) peptide (presented in single letter code) at a concentration of about 1 to about 10 micrograms(ug)/ml per $10^7$ cells for all or part of the duration of lymphocyte culture. After being sensitized to the peptide the T-lymphocytes are administered to the mammal in need of such treatment. Alternatively, the modified MART-1 peptides shown in Table 14 may be exposed to lymphocytes. Examples of how these sensitized T-cells can be administered to the mammal include but are not limited to, intravenously, intraperitoneally or intralesionally. Parameters that may be assessed to determine the efficacy of these sensitized T-lymphocytes include, but are not limited to, production of immune cells in the mammal being treated or tumor regression. Conventional methods are used to assess these parameters. Such treatment can be given in conjunction with cytokines or gene modified cells (Rosenberg, S. A. et al. (1992) *Human Gene Therapy,* 3: 75-90; Rosenberg, S. A. et al. (1992) *Human Gene Therapy,* 3: 57-73).

In addition to use as a vaccine, the compositions can be used to prepare antibodies to MART-1 antigen, peptides or analogs thereof, or modified MART-1 peptides and analogs thereof. The antibodies can be used directly as anti-melanoma agents. To prepare antibodies, a host animal is immunized using the MART-1 protein, peptides or analogs thereof, or modified peptides or analogs thereof as the immunogen and bound to a carrier as described above for vaccines. The host serum or plasma is collected following an appropriate time interval to provide a composition comprising antibodies reactive with the immunogen. The gamma globulin fraction or the IgG antibodies can be obtained, for example, by use of saturated ammonium sulfate or DEAE Sephadex, or other techniques known to those skilled in the art. The antibodies are substantially free of many of the adverse side effects which may be associated with other anti-cancer agents such as chemotherapy.

The antibody compositions can be made even more compatible with the host system by minimizing potential adverse immune system responses. This is accomplished by removing all or a portion of the Fc portion of a foreign species antibody or using an antibody of the same species as the host animal, for example, the use of antibodies from human/human hybridomas. Humanized antibodies (i.e., nonimmunogenic in a human) may be produced, for example, by replacing an immunogenic portion of an antibody with a corresponding, but nonimmunogenic portion (i.e., chimeric antibodies). Such chimeric antibodies may contain the reactive or antigen binding portion of an antibody from one species and the Fc portion of an antibody (nonimmunogenic) from a different species. Examples of chimeric antibodies, include but are not limited to, non-human mammal-human chimeras, rodent-human chimeras, murine-human and rat-human chimeras (Robinson et al., International Patent Application 184,187; Taniguchi M., European Patent Application 171,496; Morrison et al., European Patent Application 173,494; Neuberger et al., PCT Application WO 86/01533; Cabilly et al., 1987 Proc. Natl. Acad. Sci. USA 84:3439; Nishimura et al., 1987 Canc. Res. 47:999; Wood et al., 1985 Nature 314:446; Shaw et al., 1988 J. Natl. Cancer Inst. 80: 15553, all incorporated herein by reference).

General reviews of "humanized" chimeric antibodies are provided by Morrison S., 1985 Science 229:1202 and by Oi et al., 1986 BioTechniques 4:214.

Suitable "humanized" antibodies can be alternatively produced by CDR or CEA substitution (Jones et al., 1986 Nature 321:552; Verhoeyan et al., 1988 Science 239:1534; Siedleret al. 1988 J. Immunol. 141:4053, all incorporated herein by reference).

The antibodies or antigen binding fragments may also be produced by genetic engineering. The technology for expression of both heavy and light cain genes in *E. coli* is the subject the following PCT patent applications; publication number WO 901443, WO901443, and WO 9014424 and in Huse et al., 1989 Science 246:1275-1281.

The antibodies can also be used as a means of enhancing the immune response. The antibodies can be administered in amounts similar to those used for other therapeutic administrations of antibody. For example, pooled gamma globulin is administered at a range of about 1 mg to about 100 mg per patient. Thus, antibodies reactive with the MART-1 antigen can be passively administered alone or in conjunction with other anti-cancer therapies to a mammal afflicted-with melanoma. Examples of anti-cancer therapies include, but are not limited to, chemotherapy, radiation therapy, adoptive immunotherapy therapy with TIL.

Alternatively, anti MART-1 antigen antibodies can be induced by administering anti-idiotype antibodies as immunogens. Conveniently, a purified anti-MART-1 antibody preparation prepared as described above is used to induce anti-idiotype antibody in a host animal. The composition is administered to the host animal in a suitable diluent. Following administration, usually repeated administration, the host produces anti-idiotype antibody. To eliminate an immunogenic response to the Fc region, antibodies produced by the same species as the host animal can be used or the Fc region of the administered antibodies can be removed. Following induction of anti-idiotype antibody in the host animal, serum or plasma is removed to provide an antibody composition. The composition can be purified as described above for anti-MART-1 antibodies, or by affinity chromatography using anti-MART-1 antibodies bound to the affinity matrix. The anti-idiotype antibodies produced are similar in conformation to the authentic MART-1-antigen and may be used to prepare an MART-1 melanoma antigen vaccine rather than using the MART-1 protein, peptides analogs or portions thereof.

When used as a means of inducing anti-MART-1 antibodies in an animal, the manner of injecting the antibody is the same as for vaccination purposes, namely intramuscularly, intraperitoneally, subcutaneously, interlesionally, or the like in an effective concentration in a physiologically suitable diluent with or without adjuvant. One-or more booster injections may be desirable.

The MART-1 derived proteins or peptides or modified peptides of this invention are also intended for use in producing antiserum designed for pre- or post-disease prophylaxis. Here the MART-1 antigen, peptides or analogs thereof, or modified MART-1 peptides or analogs thereof is formulated with a suitable adjuvant and administered by injection to human volunteers, according to known methods for producing human antisera. Antibody response to the injected proteins is monitored, during a several-week period following immunization, by periodic serum sampling to detect the presence of anti-MART-1 serum antibodies, using an immunoassay as described herein.

The antiserum from immunized individuals may be administered as a prophylactic measure for individuals who are at risk of developing melanoma. The antiserum is also useful in treating an individual afflicted with melanoma for post-disease prophylaxis.

For both in vivo use of antibodies to MART-1 antigen and anti-idiotype antibodies and diagnostic use, it may be preferable to use monoclonal antibodies. Monoclonal anti-MART-1 antibodies or anti-idiotype antibodies can be produced as follows. The spleen or lymphocytes from an immunized animal are removed and immortalized or used to prepare hybridomas by methods known to those skilled in the art. (Goding, J. W. 1983. Monoclonal Antibodies: Principles and Practice, Pladermic Press, Inc., NY, N.Y., pp. 56-97). To produce a human-human hybridoma, a human lymphocyte donor is selected. A donor known to have a melanoma carrying the MART-1 antigen may serve as a suitable lymphocyte donor. Lymphocytes can be isolated from a peripheral blood sample or spleen cells may be used if the donor is subject to splenectomy. Epstein-Barr virus (EBV) can be used to immortalize human lymphocytes or a human fusion partner can be used to produce human-human hybridomas. Primary in vitro immunization with peptides can also be used in the generation of human monoclonal antibodies. Examples of preferred MART-1 peptides, but not limited to are, AAGIGILTV (SEQ ID NO: 4), EAAGIGILTV (SEQ ID NO: 17) and AAGIGILTVI (SEQ ID NO: 18) (peptides are presented in single letter amino acid code). Most preferably AAGIGILTV (SEQ ID NO: 4) is used as the immunogen. Alternatively, peptides derived from the MART-1 amino acid sequence and modified to enhance binding of the peptide to a MHC Class I molecule may also be used. By way of example the modified peptides shown in Table 14 may be used as the immunogen.

Antibodies secreted by the immortalized cells are screened to determine the clones that secrete antibodies of the desired specificity. For monoclonal MART-1 antigen or peptide antibodies, the antibodies must bind to MART-1 antigen or peptide. For monoclonal anti-idiotype antibodies, the antibodies must bind to anti-MART-1 antibodies. Cells producing antibodies of the desired specificity are selected.

The antibodies or chimeric antibodies described herein may also be coupled to toxin molecules radio-isotopes and drugs by conventional methods (Vitetta et al. (1991) in "Biologic Therapy of Cancer" De Vita V T, Hellman S., Rosenberg, S. A. (eds) J.B. Lippincott Co. Philadelphia; Larson, S. M. et al. (1991) in "Biological Therapy of Cancer" De Vita V. T., Hellman S., Rosenberg, S. A. (eds) J.B. Lippincott Co., Philadelphia). Examples of toxins to which the antibodies may be coupled to include, but are not limited to, ricin or diphtheria toxin. Examples of drugs or chemotherapeutic agents include, but are not limited to, cyclophosphamide or doxorubcin. Examples of radioisotopes, include, but are not limited to, $^{131}$I, Antibodies covalently conjugated to the aforementioned agents can be used in cancer immunotherapy for treating melanoma.

Local administration to the afflicted site may be accomplished through means known in the art, including, but not limited to, topical application, injection, and implantation of a porous device containing cells recombinantly expressing the infusion, implantation of a porous device in which the MART-1 antibodies or chimeric antibodies, antibodies coupled to toxins, drugs or radiolabels or portions thereof are contained.

The above described antibodies and antigen binding fragments thereof may be supplied in kit form alone, or as a pharmaceutical composition for in vivo use. The antibodies may be used for therapeutic uses, diagnostic use in immunoassays or as an immunoaffinity agent to purify the MART-1 protein or peptides as described herein.

The present invention also provides a substantially purified and isolated nucleic acid sequence, designated c(complementary)DNA25 (FIG. 4; SEQ. ID. NO. 26) which encodes a second melanoma recognized by tumor infiltrating lymphocytes. The TIL which recognize the melanoma antigen encoded by cDNA25 are associated with in vivo tumor rejection. The TIL recognized the melanoma antigen encoded by cDNA25 in the context of HLA-A2. Comparison of the cDNA25 nucleic acid sequence (FIG. 4; SEQ. ID NO 26)

with the nucleic acid sequences for genes encoding a melanocyte-melanoma specific protein gp100 shows this sequence to be similar, but distinct, from the previously identified sequences for gp100. Previously identified sequences for gp100 include gp100 (GenBank Accession No. M32295; also designated gp95), Pmel 17 (GenBank Accession No. M77348; Kwon et al., (1991) *Proc. Natl. Acad. Sciences* (USA) 88:9228-9232) and ME20 (Maresh et al. (1994) *DNA and Cell Biology* 13:87-95).

The cDNA25 sequence provided herein (FIG. 4; SEQ. ID. NO. 26) differs from the previously reported gp100 sequence in Genbank (Genbank Accession No. M32295) by two nucleotides, from the Pmel 17 sequence (Kwon et al. (1991) *Proc. Natl. Acad. Sciences* (USA) 88: 9228-9232) by three nucleotides and a twenty one base pair deletion, and from the ME20 sequence (Maresh et al. (1994) *DNA and Cell Biology* 13:87-95) by a single nucleotide difference. At the amino acid level, the protein encoded by cDNA25 differs from the gp100 in GenBank (GenBank Accession #M32295) by one amino acid at position 162, by a two amino acid difference at positions 162 and 274, compared to Pmel 17 and did not contain 7 amino acids that existed in Pmel 17 at positions 588-594. Therefore, cDNA25 appears to encode for a different form of the gene for gp100. The differences between the cDNA25 nucleic acid sequence (FIG. 4; SEQ. ID. NO. 26) and amino acid sequence (FIG. 5A; SEQ. ID. NO. 27) and previously reported gp100 sequences may be due to polymorphisms, allelic variations, or to mutations within the tumor. Experiments with mouse tumors have shown that new antigens recognized by T-cells can result from point mutation in the coding region of the inactive gene (Boon, T (1992) *Advances in Cancer Research* 58:177-210).

This invention also provides immunogenic peptides derived from the gp100 protein sequence provided herein. (FIG. 5A; SEQ. ID. NO. 27). These immunogenic peptides represent the antigenic portions of the gp100 protein (FIG. 5A; SEQ. ID. NO. 27) recognized by TIL. Examples of immunogenic peptides include, but are not limited to, LLDGTATLRL (peptide G10-4; SEQ ID NO: 33; FIG. 4, nucleotides 1407-1436), VLYRYGSFSV (peptide G10-5; SEQ ID NO: 34; FIG. 4 nucleotides 1464-1493), ALDGGNKHFL (peptide G10-22; SEQ ID NO: 35; FIG. 4, nucleotides 708-737), VLKRCLLHL (peptide G9-19 SEQ ID NO: 36; FIG. 4, nucleotides 48-74), VLPSPACQLV (peptide G10-8; SEQ ID NO: 37; FIG. 4 nucleotides 1668 to 1797) SLADTNSLAV (peptide G10-9; SEQ ID NO: 38; FIG. 4 nucleic acids 1746 to 1775) SVSVSQLRA (peptide G9-216; SEQ ID NO:39; FIG. 4, nucleotides 684 to 710) YLEPGPVTA (peptide G9-280; SEQ ID NO:40; FIG. 4; nucleotides 876-902) or LNVSLADTN (peptide G10-400; SEQ ID NO:41; FIG. 4; nucleotides 1736-1764) KTWGQYWQV (peptide $G9_{154}$; SEQ ID NO:46; FIG. 5A; amino acids 154 to 162), KTWGQYWQVL (peptide $G10_{154}$ SEQ ID NO:47; FIG. 5A; amino acids 154 to 163), ITDQVPFSV (peptide $G9_{209}$, SEQ ID NO:48; FIG. 5A; amino acids 209 to 217) and TITDQVPFSV (peptide $G10_{208}$; SEQ ID NO: 49; FIG. 5A; amino acids 208 to 217). This invention further includes analogs of these immunogenic peptides derived from the gp100 amino acid sequence (FIG. 5A; SEQ ID NO: 27). The term analog includes any peptide which displays the functional aspects of these immunogenic peptides. The term analog also includes conservative substitution or chemical derivative of the peptides as described above. These immunogenic peptides may be synthetically or recombinantly produced in the same manner or fashion as described above for MART-1.

In yet another embodiment of this invention, immunogenic peptides derived from the gp100 sequence (FIG. 5A; SEQ ID NO: 27, are modified to increase immunogenicity by enhancing the binding of the peptide to MHC molecule with which the peptide is associated when presented to T-cells. By way of example, modifications may include the substitution, deletion or addition, of one or more amino acids within the immunogenic peptide sequence, or insertion of amino acids within the given immunogenic peptide sequence or derivitization of existing amino acids within the given immunogenic peptide sequence or mutation of the amino acids within the given immunogenic peptide sequence. In a preferred modification at least one amino acid is substituted or replaced in the given immunogenic peptide sequence. Any amino acid composing the given immunogenic peptide sequence may be modified in accordance with this invention. Any amino acid may be used to substitute or replace a given amino acid within the immunogenic peptide sequence. Modification may occur at any amino acid position within the immunogenic gp100 peptide. Modified gp100 peptides is intended to include any modified immunogenic gp100 peptide exhibiting enhanced binding with the MHC molecule with which it is associated when presented to the T-cell.

By way of example peptides recognized by T cells in the context of HLA-A2 are 9 to 10 amino acids in length. Preferably for enhanced binding of the peptide to HLA-A2 the second position and last position in the peptide are hydrophobic amino acids preferably aliphatic hydrophobic amino acids. The second position may be any aliphatic hydrophobic amino acid such as, but not limited to, leucine, methionine, isoleucine, valine, threonine, glycine or alanine. The last position of the peptide (position 9 or 10 depending on the peptide's length) may be any aliphatic hydrophobic amino acid, such as but not limited to valine, leucine, alanine, leucine, isoleucine, glycine, methionine, valine, or threonine.

The first and third positions of the immunogenic peptide may be substituted or replaced with any amino acid, preferably, hydrophobic aliphatic amino acids, or aromatic amino acids. Examples of amino acids that may be used at the first or third position of the peptide include, but are not limited to, alanine, leucine, lysine, isoleucine, glycine, methionine, valine, threonine, tryptophan, phenylalanine, serine, lysine or tyrosine.

Examples of gp100 peptides that may be modified in accordance with the present embodiment include, but is not limited to LLDGTATLRL (peptide G10-4; SEQ ID NO: 33; FIG. 4, nucleotides 1407-1436), VLYRYGSFSV (peptide G10-5; SEQ ID NO: 34; FIG. 4 nucleotides 1464-1493), ALDGGNKHFL (peptide G10-22; SEQ ID NO: 35; FIG. 4, nucleotides 708-737), VLKRCLLHL (peptide G9-19 SEQ ID NO: 36; FIG. 4, nucleotides 48-74), VLPSPACQLV (peptide G10-8; SEQ ID NO: 37; FIG. 4 nucleotides 1668 to 1797) SLADTNSLAV (peptide G10-9; SEQ ID NO: 38; FIG. 4 nucleic acids 1746 to 1775) SVSVSQLRA (peptide G10-216; SEQ ID NO:39; FIG. 4, nucleotides 684 to 710) YLEPGPVTA (peptide G9-280; SEQ ID NO:40; FIG. 4; nucleotides 876-902) or LNVSLADTN (peptide G10-400; SEQ ID NO:41; FIG. 4; nucleotides 1736-1764) KTWGQYWQV (peptide $G9_{154}$; SEQ ID NO:46; FIG. 5A; amino acids 154 to 162), KTWGQYWQVL (peptide $G10_{154}$ SEQ ID NO:47; FIG. 5A; amino acids 154 to 163), ITDQVPFSV (peptide $G9_{209}$, SEQ ID NO:48; FIG. 5A; amino acids 209 to 217) and TITDQVPFSV (peptide $G10_{208}$; SEQ ID NO: 49; FIG. 5A; amino acids 208 to 217).

By way of example modified gp100 peptides derived from the immunogenic gp100 peptide KTWGQYWQV (SEQ ID NO:46) may have the formula $X_1X_2X_3GQYWQX_4$ wherein:

$X_1$ may be any amino acid, preferably any hydrophobic aliphatic amino acid, or aromatic amino acid. Examples of amino acids that may be used include, but are not limited to, alanine, leucine, lysine, isoleucine, glycine, methionine, valine, threonine, tryptophan, phenylalanine, lysine or serine, aspartic acid or tyrosine;

$X_2$ may be any hydrophobic amino acid, preferably any aliphatic hydrophobic amino acid. Examples of amino acids that may be used include, but are not limited to, leucine, methionine, isoleucine, alanine, threonine, glycine, or valine. Most preferably leucine, methionine or isoleucine.

$X_3$ may be any amino acid, preferably any hydrophobic aliphatic amino acid or aromatic amino acid. Examples of amino acids that may be used include, but are not limited to, alanine, leucine, lysine, isoleucine, glycine, methianine, valine, threonine, tryptophan, phenylalanine, serine, lysine, or tyrosine;

$X_4$ is any hydrophobic amino acid, preferably an aliphatic hydrophobic amino acid. Examples of amino acids that may be used include, but are not limited to, valine, leucine, isoleucine, methionine, alanine, threonine, or glycine.

Examples of modified peptides are shown in Table 15. A preferred modified peptide is KIWGQYWQV (G9-154-2I).

Alternatively, the immunogenic gp100 ITDQVPFSV (G9-209; SEQ ID NO:48) may be modified, such modified peptides may have the general formula $X_1X_2X_3QVPFSX_4$ wherein:

$X_1$ may be any amino acid, preferably any hydrophobic aliphatic amino acid, or aromatic amino acid. Examples of amino acids that may be used include, but are not limited to, leucine, methionine, alanine, isoleucine, valine, threanine, glycine, lysine, phenylalanine, tryptophan, or tyrosine, aspartic acid or serine;

$X_2$ is any hydrophobic amino acid, preferably a hydrophobic aliphatic amino acid. Examples of amino acids that may be used include, but are not limited to, leucine, methionine, alanine, isoleucine, valine, threanine, or glycine;

$X_3$ may be any amino acid, preferably any hydrophobic, aliphatic amino acid or aromatic amino acid. Examples of amino acids that may be used include, but are not limited to, leucine, methionine, alanine, isoleucine, valine, threonine, glycine, lysine, phenylalanine, tryptophan, tyrosine, aspartic acid or serine;

$X_4$ may be any hydrophobic amino acid, preferably any hydrophobic aliphatic amino acid. Examples of amino acids that may be used include, but are not limited to, leucine, methionine, alanine, isoleucine, valine, or threonine;

Examples of modified peptides derived from ITDQVPFSV are shown in Table 16. Preferably the peptide FLDQVPFSV (peptide G9-209-1F2L) is used.

By way of example modified gp100 peptides derived from the immunogenic gp100 peptide YLEPGPVTA (G9-280; SEQ ID NO:40) may also be modified to enhance binding to MHC Class I molecules, preferably HLA-A2 or subtypes thereof.

The modified peptides may have the general formula $X_1X_2X_3PGPVTX_4$ wherein:

$X_1$ may be any amino acid, preferably a hydrophobic aliphatic amino acid or aromatic amino acid. Examples of amino acids that may be used include, but are not limited to, leucine, methionine, alanine, isoleucine, valine, threanine, glycine, lysine, phenylalanine, tryptophan, or tyrosine, aspartic acid or serine;

$X_2$ may be any hydrophobic amino acid, preferably an aliphatic hydrophobic amino acid. Examples of amino acids that may be used include, but are not limited to, leucine, methionine, alanine, isoleucine, valine, threonine, or glycine;

$X_3$ may be any amino acid, preferably any hydrophobic aliphatic amino acid, or aromatic amino acid. Examples of amino acids that may be used include, but are not limited to, leucine, methionine, alanine, isoleucine, valine, threanine, glycine, lysine, phenylalanine, tryptophan, tyrosine, aspartic acid or serine;

$X_4$ may be any hydrophobic amino acid preferably an aliphatic hydrophobic amino acid. Examples of amino acids that may be used include but are not limited to, leucine, methionine, alanine, isoleucine, valine, threonine, or glycine.

Examples of modified peptides derived from YLEPGPVTA (G9-280; SEQ ID NO:40) are shown in Table 17. A preferred modified peptide is YLEPGPVT (G9-280-9V).

This invention further includes analogs of these modified peptides derived from the gp-100 sequence (FIG. 5A; SEQ ID NO:27). The term analog is intended to include any peptide which displays the functional aspects of these modified peptides as described above. These modified peptides may be synthetically or recombinantly provided by conventional methods.

In another embodiment the immunogenic peptides (SEQ ID NO: 33 to 38 and 46 to 49) derived from the gp100 amino acid sequence (SEQ ID NO: 27) or modified gp100 peptides as shown in Tables 15-17 or analogs thereof, may be used as a vaccine either therapeutically or prophylactically. When provided, prophylactically the vaccine is provided in advance of any evidence of melanoma. The prophylactic administration of these peptides should serve to prevent or attenuate melanoma in a mammal.

In a preferred embodiment, mammals, preferably humans, at high risk for melanoma are prophylactically treated with these vaccines. Alternatively, the vaccine may be provided therapeutically to enhance the patients own immune response to the tumor antigen prescribed on the melanoma or metastatic melanoma. The vaccine, which acts as an immunogen, may be a cell, cell lysate from cells transfected with a recombinant expression vector carrying a nucleic acid sequences encoding gp100 immunogenic peptide or a culture supernatant containing the expressed protein. Expression vectors into which nucleic acid sequences encoding these immunogenic peptides may be introduced are the same as those described above for MART-1. Alternatively, the immunogen is a partially or substantially purified recombinant gp100 peptide or analog thereof.

While it is possible for the immunogen to be administered in a pure or substantially pure form, it is preferable to present it as pharmaceutical compositions, formulations or preparations as described above for MART-1. Vaccination can be conducted by conventional methods previously described above for MART-1.

The gp100 immunogenic peptides and nucleic acids sequences encoding them may be used in bioassays, or to generate antibodies in the same manner or fashion as described above for MART-1.

In yet another embodiment of this invention, multivalent vaccines against one or more melanoma antigens are provided. Such multivalent vaccines may comprise all or part of the MART-1 protein peptides or modified peptides or gp100 peptides or modified peptides or combinations thereof.

Previous identification of genes encoding melanoma antigens have utilized PBL isolated from melanoma patients immunized or pretreated with antigens (Van Der Bruggen et al. (1991) *Science* 254: 1643-1647; Brichard et al. (1993) *J. Exp. Med.* 178: 489-495; Traversari, C., et al. (1992) *J. Exp. Med.* 176: 1453-1457). A preferred strategy is to identify genes coding for tumor antigens that are recognized by TIL from tumor-bearing patients, in the absence of immunization of said patients. Such a strategy enhances the possibility that the genes identified code for antigens involved in the natural immune response against the growing cancer. Thus, this invention also provides a method of identifying genes encoding melanoma antigens utilizing cDNA expression cloning using tumors infiltrating lymphocytes isolated (TIL) from the tumor of patients afflicted with melanoma. The method comprises the following steps: (a) isolating tumor infiltrating lymphocytes from the tumor of a mammal afflicted with melanoma; (b) introducing a melanoma cDNA library into a mammalian cell line; (c) exposing said mammalian cells to said TIL; (d) screening for expression of an antigen encoded by said cDNA in said mammalian cells recognized by said TIL; and (e) isolating said cDNA corresponding to said antigen. The tumor infiltrating lymphocytes in step (a) may be isolated from patients afflicted with melanoma including, but not limited to, the melanoma lesion, subcutaneous tissue or visceral organs. Examples of cells that may be used to prepare the cDNA library used in step (b), include, but are not limited to, fresh or cultured melanoma cells. Preferably, the cDNA library is introduced into mammalian cells not expressing melanoma antigens. If non human mammalian cells or human cells not expressing the desired HLA haplotype for recognition by the TIL are used in step (b), such cells can be cotransfected with an HLA gene as described below. Examples of cells which can be used in step (b), include but are not limited to, tumor cell lines, such as breast cancer cell line MDA 231 (ATCC #HTB26), or COS 7 cells (ATCC #CRL 1651). Examples of MHC genes which can be used include, but are not limited to, HLA-A, HLA-B, and HLA-C genes, preferably HLA-A2 and subtypes thereof (Zemmour, J. et al. (1992) *Tissue Antigens* 40:221-228). The appropriate MHC gene to be used is determined by the haplotype of the tumor cells which were the source for the cDNA library. Standard methods can be used to determine the haplotype recognized by the TIL isolated (*ASHI Laboratory Manual* (2nd Edition 1990). Examples of how to evaluate recognition of the cells containing the cDNA clone expressing an antigen recognized by the TIL includes, but is not limited to, γ-interferon assays, TNF secretion (Van de Bruggen et al., (1991) *Science* 254:1643-1647) or lysis of cells transfected with cDNA encoding for the recognized antigen. Such assays are performed by conventional methods known to one skilled in the art. Melanoma antigens can be isolated by or rescued by PCR using primer specific to flanking site of vector containing the cDNA. Examples of how to isolate the cDNA corresponding to the antigen recognized by the TIL include, but are not limited to, PCR.

Once the genes or nucleic acid sequences encoding melanoma antigens are identified, the next step is to determine the antigenic portion or epitope of the protein encoded by these genes. Therefore, in yet another embodiment of this invention, a method is provided for assessing the immunogenicity of peptides derived from the predicted amino acid sequences of the MART-1 protein (FIG. 1; SEQ ID NO: 2) or a gp100 protein (FIG. 5A; SEQ ID NO: 27). The method comprises the steps of: (a) preparing a plurality of peptides based on the MART-1 (FIG. 1; SEQ ID NO: 2) or gp100 (FIG. 5A; SEQ ID NO: 27) amino acid sequence; (b) incubating at least one of said peptides with a mammalian cell line; (c) exposing said mammalian cells incubated with said peptide to tumor infiltrating lymphocytes (TIL); and (d) screening for recognition of TIL with said cells incubated with said peptide. It is preferred that peptides of about 25 to 5 amino acids be used, more preferably 20 to 10 amino acids and most preferably 9-10 amino acids. Examples of cells that may be used in step (b) include, but are not limited to, T2-cells, (Cerundolo, V. et al. (1990) *Nature,* 345: 449-452) or EBV transformed B cell lines (Topalian et al. (1989) *J. Immunol.* 142: 3714-3725).

Examples of how to assess recognition of the cells incubated with peptide include but is not limited to, $^{51}$CR release cytotoxicity assay (Cerundolo, V. et al. (1990) *Nature* 345:449-452.) or lymphokine assays such as γ-IFN or TNF secretion. (Schwartzentruber, D. et al., (1991) *J. of Immunology* 146: 3674-3681).

T cells recognize antigen complexed with MHC Class 1 molecules. The MHC locus in all mammalian species contains numerous genes and is highly polymorphic. Different MHC molecules or haplotypes types bind different antigens. In humans the HLA complex contains the HLA-A, HLA-B and HLA-C gene loci which encode class I molecules. Lymphocytes will recognize tumor antigens on the context of HLA Class 1 molecule. If the cells containing the recombinant MART-1 expression vector are to be screened by the TIL but are not human cells, such as COS cells, or do not express a desired haplotype an expression vector containing an MHC Class 1 gene may also be introduced into the cells. (See Example 1) This, represents yet another alternative embodiment of the invention. Cells expressing MART-1 antigens and HLA antigens can by screened with TIL to detect the presence of tumor antigens in the context of a specific MHC Class 1 restriction type. The appropriate haplotype is determined by the haplotype of the tumor from which the library is derived. Examples of MHC Class I genes that may be used include, but are not limited to, HLA-A, HLA-B and HLA-C genes. Examples of preferred MHC specificities or restriction types include, but is not limited to HLA-A1, HLA-A2, such as the HLA-A2.1 subtype, or HLA-A24 (Zemmour, J. et al. (1992) *Tissue Antigens* 40:221-228). Most preferred is the HLA-A2.1 gene.

Veterinary uses are also intended to be encompassed by the compositions and therapeutic applications described herein.

All books, articles, and patents referenced herein are incorporated by reference in their entirety. The following examples illustrate various aspects of the invention and in no way intended to limit the scope thereof.

Cloning of a Gene Coding for a Shared Human Melanoma Antigen Recognized by Autologous T Cells Infiltrating into Tumors

EXAMPLE 1

Generation of Cytotoxic T Lymphocytes (CTL) and Culture of Cell Lines

–54 CTL were generated from excised tumor specimens by culturing a suspension of cells with 6000 IU/ml of IL-2 (Cetus-Oncology Division, Chiron Corp. Emeryville, Calif.) for 30-70 days as described in Kawakami, Y., et al. (1988) *J. Exp. Med.* 168:2183-2191. TIL501 and TIL1235 were predominantly CD8$^+$ and were derived from the tumor specimens of patients with advanced metastatic melanoma. The CD8$^+$ T cell clone, TIL501.A42, was established by limiting dilution methods and cultured with 120 IU/ml of IL-2 plus irradiated (once a week for 4 to 6 times) autologous tumor cells.

Melanoma-cell lines, 397mel, 501mel, 526mel, 537mel, 624mel, 888mel, 952mel, and Epstein-Barr virus (EBV) transformed B cell lines, 501EBVB, 836EBVB were established in our laboratory and cultured in RPMI1640 (GIBCO/Lifetechnologies, Grand Island N.Y.) medium containing 10% fetal calf serum (FCS) (Biofluids, Rockville Md.). (Topalian et al., (1989) *J. Immunol.* 142: 3714-3725) Normal cultured melanocytes, NHEM483, NHEM493, NHEM527, NHEM529, NHEM530, NHEM533, NHEM616 and NHEM680 were purchased from Clonetics, San Diego, Calif., FM725, FM801, FM902 were provided by M. Herlyn, Wistar Institute, Philadelphia Pa., HA002 was provided by R. Halaban, Yale university, New Haven, Conn. and cultured in melanocyte growth medium (MGM, Clonetics). Melanoma cell lines, C32, RPMI7951, WM115, A375, HS695T, Malme3M, colon cancer cell lines, Collo, SW480, WiDr, breast cancer cell lines, MDA231, MCF7, HS578, ZR75, neuroblastoma cell line, SK—N—SH, glioma cell lines, U138MG, HS683, H4, sarcoma cell line 143B, embryonal kidney cell line 293 transformed with adenovirus type 5 were purchased from ATCC, Rockville, Md. Renal cancer cell lines, UBK108 and UOK117 were provided M. Linehan NIH, Bethesda, Md. The small cell lung cancer cell line, H1092 was provided by J. D. Minna, University Texas Southwestern, Dallas, Tex. Ewing's sarcoma cell lines, TC71, RD-ES, 6647 were provided by M. Tsokos, NIH, Bethesda, Md. The neuroblastoma cell line, SK—N-AS was provided by O. M. El Badry, NIH, Bethesda, Md. The plasmacytoma cell line, HMY-C1R and the M1 fibroblast cell line were provided by W. Biddison, NIH, Bethesda, Md. Kidney epithelial cells, KAM, WLC were provided by D. J. Hazen-Martin and D. A. Sens, Medical University of South Carolina, Charleston, S.C. The monkey kidney cell line, COS7, was provided by W. Leonard, NIH, Bethesda, Md.

Cytotoxicity Assay $^{51}$Cr release assays were performed as described in Kawakami, Y., et al., (1988) J. Exp. Med. 168:2183-2191. Briefly, 5000 target cells labeled with $^{51}$Cr were mixed with varying numbers of effector cells and incubated for 5 hours (h). Then supernatants were collected, radioactivity was measured and the percent specific lysis was calculated.

IFN-γ Release Assay

Fifty to one hundred thousand responder cells and $4 \times 10^4$-$10^5$ stimulator cells were mixed in 300 ul of AIM-V medium containing 120 IU/ml IL-2 per well in a 96 flat-well microplate. After incubation for 20 h, 100 ul of supernatants were collected and added to an enzyme-linked immunosorbent assay (ELISA) plate (Immunoplate MaxiSorp, Nunc, Denmark) coated with anti-human IFN-γ monoclonal antibody (mAb) (Biosource, Camerillo, Calif.). After overnight incubation at 4° C., the plates were washed 3 times and 100 ul of a 1:2000 dilution of rabbit anti-human IFN-γ polyclonal antibody (Ab)(Biosource, Camerillo, Calif.) was added and incubated at 37° C. for 2 h. Plates were washed 3 times, and 100 ul of a 1:2000 dilution of alkaline phosphatase labelled goat anti-rabbit IgG polyclonal antibody (Ab) (Boehringer Mannheim, Indianapolis, Ind.) was added. After a 1 h incubation at 37° C., 100 ul of 4 mg/ml p-Nitrophenyl phosphate (Sigma, St Louis, Mo.) was added, incubated for 10-20 min at room temperature in the dark, and 25 ul of 1N NaOH was added to stop the reaction. Optical density was measured at 405 nm wave length and the concentration of IFN-γ was calculated in comparison to recombinant IFN-γ standards (Biogen, Cambridge, Mass.) measured in the same assay.

cDNA Expression Cloning

A cDNA library was constructed from poly A RNA from the HLA-A2$^+$ melanoma cell line, 501mel as described in (Miki, T., et al., (1989) Gene; 83:137-146 Miki et al. (1991) Proc. Nat. Acad. Sci. USA 88:5167-5171). Briefly, first strand cDNA was synthesized with a linker primer GGACAGGC-CGAGGCGGCC (T)$_{40}$ (SEQ ID NO: 42) followed by second strand cDNA synthesis. After treatment with T4 DNA ligase, an SfiI adaptor consisting of two oligonucleotides, CCAATCGCGACC (SEQ ID NO: 43) and GGTCGCGAT-TGGTAA (SEQ ID NO: 44) was ligated to the end of the cDNA. The cDNA was digested with SfiI and the digested fragment was isolated by passing through a spun column. The cDNA was then mixed with bacteriophage λpCEV27 (Miki, T. et al., (1991) Proc. Natl. Acad. Sci. (USA) 88: 5167-5771) vector arms prepared by SfiI digestion and in vitro packing was performed.

To screen for melanoma antigens, 10 ug of the amplified cDNA library containing approximately 10$^7$ clones was transfected into the HLA-A2$^+$ antigen non-expressing cell lines, MDA231 clone 7 and A375 clone 1-4 using a modified calcium-phosphate method (Mammalian Transfection Kit, Stratagene). After G418 (BRL, Gaithersburg, Md.) selection, individual colonies were isolated and cultured in 96 well microplates and replica plates were made. A mixture of $5 \times 10^4$ TIL1200 and $5 \times 10^4$ TTL1235 was added to the wells of the microplates containing the growing transfectants that were near confluence and incubated for 20 h. Supernatants were collected and IFN-γ was measured by ELISA.

Polymerase chain reaction(PCR) was performed to rescue the transfected genes from the genomic DNA of positive transfectants using SP6 and T7 primers which flank the inserted genes. The amplified products were cloned in the pCRII vector (Invitrogen, San Diego, Calif.). For cDNA clones 22 and 23, a Hind III and XhoI fragment containing the full length cDNA was subcloned into the expression vector pcDNA3 (Invitrogen, San Diego, Calif.).

To test whether the cloned cDNAs encode tumor antigens, the pcDNA3 containing the cloned genes were transiently transfected into the COS7 cell line by the DEAE dextran method (Seed, B. and Aruffo, A. (1987) Proc. Natl. Acad. Sci. (USA) 84:3365-3369). Briefly, $3 \times 10^5$ cells per well in 6 well plates were incubated at 37° C. for 4 hours (h) in 0.75 ml DMEM containing 10 ug of DEAE dextran (Sigma), 0.1 mM chloroquine and lug of the pcDNA3 containing the cloned genes and/or the pcDNA-HLA-A2.1 (Zemmour, J. et al. (1992) Tissue Antigens 40: 221-228). After medium was removed, 10% DMSO solution in HBSS buffer was added and incubated for 2 min. The cells were washed once with PBS and incubated in 7.5% FCS DMEM for 2 days. The 293 cell line was transiently transfected using lipofectamine (BRL, Gaithersburg, Md.) according to the manufacturer's recommendation. After incubation, the ability of the transfected COS7 or 293 cells to mediate IFN-γ release from TIL was assessed. The expression of the HLA-A2 gene was tested by flow cytometry. Stable transfectants were made by the calcium-phosphate method and individual colonies and pooled transfectants were tested for reactivity to TIL by cytotoxicity and IFN-γ release assays.

DNA sequencing of the cloned genes was performed by dideoxy chain termination method with dGTP and 7-deaza-dGTP. DNA and protein sequences were analyzed by the GCG program with GeneBank, and EMBL Data Library nucleotide databases and SWISS-PROT, PIR, GenPept, Brookhaven Protein Data Bank protein databases.

Northern Blot Analysis

Total RNA was isolated by the guanidine-isothiocyanate-cesium chloride centrifugation method. (Chirgwin, J. M. et al. (1979) Biochemistry 18: 5294). Total RNA from normal tissue was purchased from Clontech, (Palo Alto, Calif.). Ten to twenty micrograms of total RNA was subjected to electrophoresis in a 1% agarose formaldehyde gel and transferred to a nylon membrane (Duralon-UV membranes, Stratagene, La Jolla, Calif.) The Sal I digested fragment containing the full length cDNA from clone 22 and the β-actin cDNA (Clontech) were labeled by random priming and used as a probe. Hybridization with the probe was performed according to the QuikHyb protocol (Stratagene) at 68 C for 2-16 h. Membranes were washed two times with 2×SSC/0.1% SDS at 60 C for 15 minutes (min) and once with 0.1×SSC at 60 C at for 30 min and then autoradiography was performed.

Characterization of Cultured TIL from Melanoma Patients

Multiple TIL lines were established from HLA-A2$^+$ melanoma patients and tested for lysis of melanoma cell lines from HLA-A2$^+$ and HLA-A2$^-$ patients. HLA typing of patients is performed by conventional HLA typing techniques. HLA-A2 was selected because it is the most frequently expressed class I MHC antigen (about 50% of individuals) and has been shown to be a dominant restriction element for the recognition of melanoma antigens (Crowley, N. J., et al. (1991), *J. Immunol.* 146:1692-1694). TIL501, TIL1235 and TIL1200 exhibited specific recognition of shared melanoma antigens in an HLA-A2 restricted fashion. TIL501.A42 was a T cell clone established from TIL501 by limiting dilution. These TIL caused lysis or released cytokines including IFN-γ, TNFα and GM-CSF when cocultured with a variety of HLA-A2$^+$ melanoma or melanocyte cell lines but not HLA-A2$^-$ melanoma lines or HLA-A2$^+$ non-melanoma cell lines including the breast cancer cell line, MDA 231. Two representative experiments are shown in Table 1. Thus, these CTL seemed to recognize a non-mutated peptide derived from a melanocyte lineage specific antigen.

Cloning of cDNA Coding for Melanoma Antigens Recognized by T Cells

A cDNA library from the HLA-A2$^+$ 501mel melanoma cell line was transfected into two highly transfectable HLA-A2.1$^+$ cancer cell lines, MDA231 and A375. These cell lines were not lysed by melanoma specific TIL but were lysed by HLA-A2 restricted influenza M1 specific CTL after incubation with the M1$_{58-66}$ peptide (GILGFVFTL (SEQ ID NO:45); single letter code) derived the influenzae matrix protein or infection with a recombinant vaccinia virus containing the M1 gene (data not shown). Thus, these cell lines exhibited normal antigen processing and presenting ability but were not lysed by these melanoma-specific TIL because of the lack of expression of the relevant melanoma antigens. After selection with G418, approximately 6700 transfected clones from each cell line were isolated and grown in microplates. Using the IFN-γ release assay, 21 MDA231 and 27 A375 positive clones were isolated and rescreened. Of these clones, eight MDA231 and seven A375 clones were positive in a second screening assay.

In order to rescue the integrated genes, PCR using genomic DNA from these positive transfectants was performed with SP6 and T7 primers flanking the insert genes. Eight genes that were amplified from the seven transfectants which showed 1 to 2 sharp bands, including a 1.6 Kb band from MDA-22 and MDA-23 transfectants, were subcloned into the pCRII cloning vector, and then further cloned into the pcDNA3 eukaryotic expression vector. The 1.6 Kb band detected by Northern blot analysis with the cDNA 22 probe suggested that this fragment was a full length cDNA.

Transient transfection of the expression vector pcDNA3 containing the cDNA from clones 22 or 23 into either COS7 or 293 cells along with the HLA-A2.1 gene conferred reactivity to TIL1235 and TIL501.A42 as demonstrated by the specific release of IFN-γ (Table 2, Experiments 1 and 2). Stable transfection of these cDNA fragments into MDA 231 or A375mel cell lines also conferred reactivity to TIL1235 and TIL501.42 (Table 2, Experiment 3). TIL501.A42 could lyse MDA231 stably transfected with cDNA 22 (data not shown). These results indicated that these cDNAs encode a melanoma antigen recognized by HLA-A2 restricted TIL from melanoma patients. Transfection of another clone, MDA-25 stimulated the release of interferon-γ only from TIL 1200.

Characterization of this cDNA revealed it to be similar, but distinct, from a previously described melanoma antigen

TABLE 1

Specificity of TIL 501.A42 and TIL 1235 for Melanomas and Melanocytes

| | A. Lytic Specificity* | | | | B. Cytokine Release Specificity** | | | |
|---|---|---|---|---|---|---|---|---|
| Target* | HLA-A2 | TIL501.A42 | TIL1235 % Lysis | LAK$^+$ | Stimulator** Cells | HLA-A2 | TIL501.A42 | TIL1235 pg IFN- | TIL586$^{++}$ γ/ml |
| 501mel | + | 54 | 51 | 78 | 501mel | + | 647 | 219 | <50 |
| 526mel | + | 25 | 33 | 74 | 586mel | − | <50 | <50 | 1034 |
| 624mel | + | 23 | 27 | 75 | NHEM493 | + | 1835 | 850 | <50 |
| 952mel | + | 10 | 11 | 75 | NHEM527 | + | 1638 | 749 | <50 |
| Malme3M | + | 36 | 41 | 70 | NHEM530 | + | 1224 | 2532 | <50 |
| C32 | + | 17 | 23 | 82 | NHEM533 | + | 300 | 251 | <50 |
| RPMI7951 | + | 1 | 6 | 67 | NHEM616 | + | 635 | 423 | <50 |
| WM115 | + | −2 | 3 | 68 | FM725 | + | 5975 | 1471 | <50 |
| HS695T | + | 1 | 2 | 87 | FM801 | + | 1375 | 893 | 62 |
| 397mel | − | −1 | 0 | 70 | NHEM483 | − | <50 | <50 | <50 |
| MDA231 | + | 0 | 3 | 94 | NHEM680 | − | <50 | <50 | 548 |
| | | | | | HA002 | − | <50 | <50 | <50 |

TIL 501.A42 and TIL1235 lysed most HLA-A2 melanoma cell lines and secreted IFN-γ when cultured with HLA-A2 melanomas and melanocytes.
*51Cr release assay was performed at E:T = 20:1 for TIL501.A42, at 40:1 for TIL1235. All targets were melanoma cell lines except for MDA231 which was a breast cancer cell line.
**IFN-γ in the supernatant was measured after TIL and stimulator cells were coincubated for 20 hr. 501mel and 586mel are melanoma cell lines. All others were normal melanocyte cell lines.
$^+$LAK: Lymphokine activated killer cells.
$^{++}$TIL586 is class I MHC restricted melanoma specific TIL, not restricted by HLA-A2.

gp100 recognized by monoclonal antibody HMB45. This clone is described in more detail in Example 3.

The cDNA sequence of clones 22 and 23 were identical except at a single base that was believed to be a change introduced by PCR. Two other independently amplified fragments were also sequenced to clarify this region and the consensus sequence is shown in FIG. 1. The longest open reading frame in this gene consists of 354 bases corresponding to a 118 amino acid protein of 13 kd. This sequence did not show significant similarity to any complete nucleotide or protein sequences in established databases. Amino acids 27-47 consist of a hydrophobic region that may contain the HLA-A2 binding peptides (Falk, K., et al. (1991), *Nature* 351:290-296; Hunt, D. F., et al. (1992), *Science* 255:1261-1263; Ruppert, J., et al. (1993), *Cell* 74:929-937; Nijman, H. W., et al. (1993), *Eur. J. Immunol.* 23:1215-1219). The antigen encoded by the cDNA 22 and 23, was designated the MART-1 antigen (Melanoma Antigen Recognized by T cells-1). Of the ten HLA-A2 restricted TIL lines generated nine recognized MART-1, and four recognized a form of gp100 isolated and described herein (see Example 3) and none appeared to recognize MAGE-1 (Zakut, R., et al. (1993), *Cancer Res* 53:5-8.; data not shown).

TABLE 2

Interferon Gamma Secretion by TIL501.A42 and TIL 1235 When Cultured with HLA-A2+ Cell Lines Transfected with the Gene 22 or 23

| Stimulator Cell | Transfected Gene | HLA-A2 | TIL501.A42 pg/ml | TIL1235 pg/ml |
|---|---|---|---|---|
| Exp. 1 | | | | |
| 501mel | none | + | 1009* | 1076 |
| 397mel | none | − | <50 | <50 |
| COS7 | none | − | <50 | <50 |
| COS7 | HLA-A2.1 | + | <50 | <50 |
| COS7 | 22 | − | <50 | <50 |
| COS7 | HLA-A2.1+22 | + | 771 | 1049 |
| Exp. 2 | | | | |
| 501mel | none | + | ND+ | 1051 |
| 397mel | none | − | ND | <50 |
| 293 | HLA-A2.1 | + | ND | <50 |
| 293 | 22 | − | ND | <50 |
| 293 | HLA-A2.1+22 | + | ND | 255 |
| Exp. 3 | | | | |
| 501mel | none | + | 1073 | 1056 |
| 397mel | none | − | <50 | <50 |
| MDA231 | none | + | <50 | <50 |
| MDA231 | 23 | + | 674 | 725 |
| A375 | none | + | <50 | <50 |
| A375 | 23 | + | 264 | 131 |

IFN-γ in the supernatant was measured after TIL were coincubated for 20 hr with COS7 or 293 cell lines transiently transfected with the pcDNA3 containing the HLA-A2.1 and/or cDNA 22 by the DEAE-dextran method (Exp. 1 & 2), or with the A375 or MDA231 cell lines stably transfected with cDNA 23 (Exp. 3).
IFN-γ was secreted only when TIL were incubated with HLA-A2+ cell lines transfected with the cDNA 22 or 23.
*IFN-γ secreted by TIL alone without stimulator (<50 pg/ml) was subtracted.
+Not done

TABLE 3

Expression of the MART-1 Gene in a Variety of Tissue and Cell Lines

| | |
|---|---|
| Melanoma HLA-A2+ | |
| 501mel | + |
| 526mel | + |
| 624mel | + |
| Malme3M | + |
| 952mel | + |
| 697mel | + |
| C32 | + |
| RPMI7951 | − |
| WM115 | − |
| A375 | − |
| HLA-A2− | |
| 397mel | + |
| 888mel | + |
| 537mel | + |
| 586mel | + |
| Melanocyte | |
| NHEM483 | + |
| NHEM493 | + |
| NHEM529 | + |
| NHEM530 | + |
| FM902 | + |
| FM906 | + |
| HA002 | + |
| Normal fresh tissue | |
| Brain | − |
| Retina | + |
| Adrenal gland | − |
| Lung | − |
| Liver | − |
| Kidney | − |
| Spleen | − |
| Thymus | − |
| Testis | − |
| Fetal liver | − |
| Non-melanoma cell lines T-cell | |
| TILA | − |
| TILB | − |
| B-cell | |
| Daudi | − |
| HMY-CIR | − |
| 501EBVB | − |
| 836EBVB | − |
| Fibroblast | |
| M1 fibroblast | − |
| Kidney epithelial cell | |
| KAM | − |
| WLC | − |
| Colon cancer | |
| Collo | − |
| SW480 | − |
| WiDr | − |
| Breast cancer | |
| MDA231 | − |
| MCF7 | − |
| HS578 | − |
| ZR75 | − |
| Neuroblastoma | |
| SK-N-AS | − |
| SK-N-SH | − |
| Ewing sarcoma | |
| TC75 | − |
| RD-ES | − |
| 6647 | |
| Sarcoma | |
| 143B | − |

TABLE 3-continued

Expression of the MART-1 Gene in a Variety of Tissue and Cell Lines

| Glioma | |
| --- | --- |
| U138MG | − |
| HS683 | − |
| Renal cell cancer | |
| UOK108 | − |
| UOK117 | − |
| Small cell lung cancer | |
| H1092 | − |

Northern blot analysis with 10-20 ug of total RNA was probed with the full length cDNA of the gene 22. The RNA from most melanomas, all melanocyte cell lines tested and retina were positive.

Expression of MART-1

Northern blot analysis of a variety of cell lines including melanoma, melanocyte and nonmelanoma cancer cell lines and normal tissues was performed to evaluate the expression of the gene coding for MART-1 (Table 3). Seven of ten HLA-A2$^+$ melanoma cell lines, all four HLA-A2$^-$ melanoma cell lines, and all seven melanocyte cell lines tested were positive for MART-1 RNA expression. In this Northern analysis, all HLA-A2$^+$ melanoma cell lines recently established in our laboratory expressed MART-1 RNA. There was a perfect correlation between MART-1 expression and lysis by TIL501.A42 in the 10 HLA-A2$^+$ melanoma lines shown in Table 3. TIL 501.A42 which recognized the MART-1 Ag lysed 13 of 17 (76%) HLA-A2$^+$ melanoma cell lines tested (data not shown). Of ten normal human tissues examined for mRNA expression by Northern blot analysis only retina was positive. No positivity was seen in any cell lines from T cells, B cells, kidney epithelial cells or fibroblasts or in 19 nonmelanoma tumors. It thus appears that MART-1 is a previously undescribed antigen expressed on melanocyte lineage cells from skin and retina that is also expressed on melanoma cells.

Studies using a panel of T cell clones and immunoselected melanoma clones (Knuth, A., et al. (1989), *Proc. Natl. Acad. Sci.* (USA) 86:2804-2808; Wolfel, T., et al. (1987), *J. Exp. Med.* 170:797-810), as well as studies analyzing HPLC fractionated peptides from melanoma cells (Slingluff, C. L., et al. (1993), *J. Immunol.* 150:2955-2963; Storkus, W. J., et al. (1993), *J. Immunol.* 151:3719-3727) suggest that multiple antigenic peptides that can provoke an immune response exist on melanomas. By cDNA cloning, two genes encoding melanoma antigens have been identified; MART-1 (FIG. 1; SEQ ID NO. 1) and a gp100 gene (see Example 3; FIG. 4; SEQ ID NO. 26). MART-1 and the form of gp100 identified herein (FIGS. 4 & 5A; SEQ. ID NOS. 26 and 27), both are recognized by HLA-A2.1 restricted TIL. The MART-1 antigen is a 118 amino acid protein of approximately 13 kd. Neither the gene nor the amino acid sequence for MART-1 have been previously described.

MART-1 RNA was expressed in 11 of 14 HLA-A2.1 positive or negative melanoma lines, and 7 of 7 melanocyte lines. With the exception of retinal tissue no MART-1 expression was found on any normal tissue tested, T-cell lines, B-cell lines, kidney epithelial lines, a fibroblast line or 19 tumor cell lines from cancers of the colon, breast, brain, kidney, lung or bone.

Another melanoma antigen, MAGE-1, has been described that is recognized by T cells derived from peripheral blood lymphocytes following repetitive in vivo or in vitro immunization (Van Der Bruggen, et al. (1991), *Science* 254:1643-1647).

The identification of genes associated with melanoma tumor antigens opens new possibilities for active specific immunization approaches to the immunotherapy of patients with cancer based on the introduction of these genes into viral or bacterial vector systems. The possibility exists that immune reactions induced against melanocyte-melanoma lineage antigens such as MART-1 may be generated against normal cells. Vitiligo, probably resulting from anti-melanocyte immune reactions, has been reported to be associated with a favorable prognosis in patients with melanoma (Nordlund, J. J., et al. (1983), *J. Am. Acad. Dermatol.* 9:689-695); Bystryn, J-C, et al. (1987), *Arch. Dermatol.* 123:1053-1055), and has also been reported in patients responding to chemoimmunotherapy (Richards, J. M., et al. (1992), *J. Clin. Oncol.* 10:1338-1343). TIL with anti melanocyte-melanoma reactivities have been administered to patients with advanced melanoma (Rousenberg, S. A., et al. (1988), *N Engl J Med* 319:1076-1680; Rosenberg S. A., *J. Clin. Oncol.* 10:180-199) and although sporadic vitiligo has been seen in these patients, no adverse ophthalmologic effects related to the possible expression of these melanocyte antigens on retinal cells has been observed.

Because HLA-A2 is present in about 50% of individuals and the HLA-A2 restricted MART-1 antigen also appears to be widely expressed on melanomas, immunization with the MART-1 antigen may be particularly useful for the development of active immunotherapies.

EXAMPLE 2

Characterization of Immunogenic Epitopes of MART-1

Generation of Melanoma Specific CTL Lines and a Clone from TIL

Melanoma specific CTL lines were generated by culturing a single cell suspension made from metastatic melanoma with 6000 U/ml of IL2 (Cetus-Oncology Division, Chiron Corp. Emeryville, Calif.) as previously reported (Kawakami, Y. et al., (1988) *J. Exp. Med.* 168:2183) A T-cell clone, A42 was established by limiting dilution methods from patient, 501.

Assessment of Antigen Recognition by CTL $^{51}$Cr release cytotoxicity assays and cytokine release assays using ELISA to measure IFN-γ, GM-CSF and TNF-α were performed to analyze the reactivity of TIL as described in Kawakami, Y. et al. (1988), *J. Exp. Med.* 168:218 (see Example 1). Melanoma cell lines were established in the laboratory. For analysis of the recognition of known antigens by TIL, the COS7 cell line transfected with cDNAs encoding either, MART-1, gp100, or tyrosinase related protein (gp75) (Cohen, T. et al., (1990) *Nucleic Acids Research* 18:2807) along with HLA-A2.1 cDNA were incubated with TIL for 20 h and the amount of IFN-γ secreted into the supernatant was measured by ELISA as described in Example 1. The cDNA encoding MART-1 (see Example 1) or gp100 (see Example 3) in plasmid pcDNA3 (Invitrogen, San Diego, Calif.) was cloned from a 501mel melanoma cDNA library by screening with TIL1235 or TIL1200, respectively (see Example 1). The cDNA encoding tyrosinase related protein(gp75) in pCEV27 plasmid was isolated from 501mel melanoma cDNA library using a probe generated by PCR based on the reported sequence of gp75 (Cohen et al. (1980) *Nucleic Acids Research* 18:2807).

Peptide Synthesis and Identification of Antigenic Peptides

Peptides were synthesized by a solid phase method using a Gilson AMS 422 multiple peptide synthesizer. The peptides were purified by HPLC on a Vydac C-4 column with 0.05% TFA/water-acetonitrile. To identify the antigenic peptides, TIL lysis of T2 cell lines preincubated for 2h with each peptide was measured using a $^{51}$Cr release cytotoxicity assay.

HA-A2 Restricted Melanoma Specific TIL

HLA-A2 restricted melanoma specific CTL lines and a clone, A42, were established from lymphocytes infiltrating into tumors of 10 melanoma patients. These TIL recognized autologous and most. allogeneic fresh or cultured melanoma cells expressing HLA-A2, but did not recognize HLA-A2 TIL lines recognized gp100. None of these TIL recognized gp75 using this assay. Thus, MART-1 is a common melanoma antigen recognized by most HLA-A2 restricted TIL derived from melanoma patients.

Identification of MART-1 Epitopes for TIL

To identify the MART-1 epitopes for these TIL, 23 peptides were selected based on the known peptide binding motifs to HLA-A2.1 (Falk, K. et al., (1993) *Nature,* 351:290; Hunt, D. F. et al. (1992), *Science,* 255:1261; Ruppert, J. et al., (1993) *Cell* 74:929), synthesized (>90% purity) and screened by testing lysis of the HLA-A2.1$^+$ T2 cell line by TIL after incubation of the T2 line with each peptide (Table 5). The T2 cells (Cerundolo, V. et al.;

TABLE 4

Recognition of melanoma antigens by HLA-A2 restricted melanoma specific TIL

| Stimulator Cell line | Transfected cDNA | HLA-A2 | TIL 501 | TIL 620 | TIL 660 | TIL 1074 | TIL 1088 | TIL 1128 | TIL 1143 | TIL 1200 | TIL 1235 |
|---|---|---|---|---|---|---|---|---|---|---|---|
| | | | | | | IFN-γ secretion (pg/ml) | | | | | |
| 501mel | none | + | 93 | 720 | 530 | 670 | 491 | 272 | 354 | 736 | 750 |
| 397mel | none | − | 0 | 0 | 0 | 0 | 0 | 0 | 0 | 0 | 0 |
| COS7 | none | − | 0 | 0 | 0 | 0 | 0 | 0 | 14 | 0 | 0 |
| COS7 | HLA-A2.1 | + | 0 | 0 | 0 | 0 | 0 | 0 | 0 | 0 | 0 |
| COS7 | MART-1 | − | 0 | 0 | 0 | 0 | 0 | 0 | 12 | 0 | 0 |
| COS7 | gp100 | − | 0 | 0 | 0 | 0 | 0 | 0 | 14 | 0 | 0 |
| COS7 | gp75 | − | 0 | 0 | 0 | 0 | 0 | 0 | 0 | 0 | 0 |
| COS7 | HLA-A2.1 + MART-1 | + | 270 | 196 | 131 | 625 | 328 | 52 | 184 | 0 | 743 |
| COS7 | HLA-A2.1 + gp100 | + | 0 | 89 | 17 | 0 | 0 | 0 | 41 | 391 | 8 |
| COS7 | HLA-A2.1 + gp75 | + | 0 | 0 | 0 | 11 | 0 | 0 | 7 | 0 | 0 |

IFN-γ was measured in the supernatants after HLA-A2 restricted melanoma specific TIL were coincubated with COS7 cells cotransfected with cDNAs encoding proteins expressed in melanoma with or without HLA-A2.1 cDNA. All TIL except TIL1200 secreted IFN-γ when cultured with COS7 cotransfected with cDNAs encoding MART-1 and HLA-A2.1. TIL620, 660, 1143 and 1200 secreted IFN-γ when cultured with COS7 cotransfected with the cDNAs encoding gp100 and HLA-A2.1.

melanomas or HLA-A2$^+$ non-melanoma cell lines (Kawakami et al. (1992) *J. Immunol* 148:638). They also recognized HLA-A$^+$ normal cultured melanocytes derived from neonatal skin (see Example 1 and Kawakami, Y. et al. (1993), *J. Immunotherapy* 14:88). Thus, these TIL recognized non-mutated self-peptides derived from proteins expressed in melanoma and melanocytes in association with HLA-A2.

Recognition of Additional Melanoma Proteins by TIL

To evaluate the frequency of recognition of 4 isolated melanoma proteins including MART-1, a form of gp100 (FIG. 5A; SEQ ID NO: 26, see Example 3), and tyrosinase related protein(gp75), the reactivity of TIL to COS7 was tested on cell lines transfected with cDNAs encoding these 3 proteins with or without the cDNA encoding HLA-A2.1. One of several experiments with 9 TIL is shown in Table 4. Eight of the nine HLA-A2 restricted melanoma specific TIL secreted IFN-γ when incubated with COS7 cotransfected with MART-1 and HLA-A2.1. Only TIL1200 which is a relatively oligoclonal CTL line (Shilyansky, J. et al., (1994) *Proc. Natl. Acad. Sci.* (USA) 91:2829) did not respond to this COS transfectant. Four TIL (620, 660, 1143, 1200) recognized gp100 when transfected along with HLA-A2.1. TIL1200 secreted large amounts of IFN-γ compared to TIL620, 660, and 1143, suggesting that only a small subset of T-cells in these latter 3 (1990) *Nature* 345: 449-452) cell line was lysed well by all 4 HLA-A2 restricted melanoma specific TIL tested when preincubated with either peptides M9-2, M10-3, or M10-4. Both 10 amino acid peptides, M10-3 and M10-4 contain the M9-2 sequence, with M10-3 having an additional glutamic acid at its N-terminus and M10-4 having an extra isoleucine at its C-terminal end. These peptides are located in a hydrophobic putative transmembrane domain in MART-1. The same lysis was observed when other HLA-A2$^+$ cells incubated with these peptides were used as targets including the K4B (provided by Dr. William Biddson, NIH; Storkus. W et al. (1993) *J. of Immunology* 151:3719-3727) and 501EBVB Epstein-Barr virus transformed B cells (Topalian et al. (1989) *J. Immunol.* 142: 3714-3725) or HMY-C1R B cells (Dr. William Biddson; NIH; Storkus, W. et al., (1993) *J. of Immunol.* 151: 3719-3727) transfected with the HLA-A2.1 gene (data not shown).

Figure 2B:
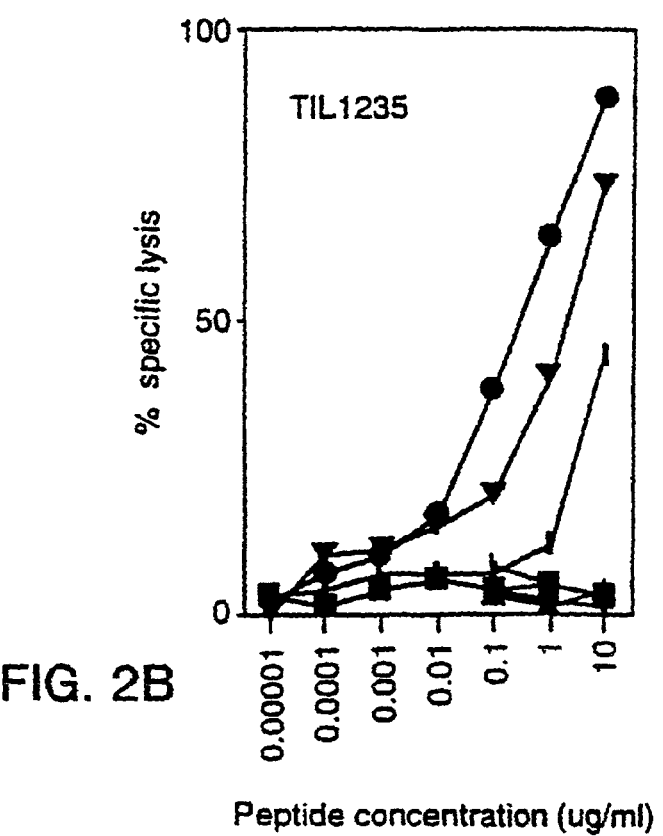

The peptides, M9-1, M9-2, M9-3, M10-2, M10-3, M10-4 and M10-5 were further purified and titrated in order to evaluate their relative ability to sensitize T2 cells to lysis by MART-1 reactive TIL1235 or T cell clone A42 (FIG. 2). The purified peptides M9-2, M10-3 and M10-4 were required in minimum concentrations of 1 ng/ml, 10 ng/ml an 1000 ng/ml, respectively. The purified M10-4 was not recognized by TIL clone A42 even at 10 ug/ml as shown in FIG. 2. M9-1, M9-3, M10-2, and M10-5 peptides were not recognized by either A42 or TIL1235.

TABLE 5

Lysis of T2 cells preincubated with synthetic MART-1 peptides

| Target | Peptide |  | A42 | TIL 1235 | TIL 660 | TIL 1074 |
|---|---|---|---|---|---|---|
|  |  |  |  | % specific lysis |  |  |
| 501mel | none |  | 47 | 30 | 31 | 41 |
| 397mel | none |  | 1 | 0 | 1 | 2 |
| T2 | none |  | -2 | -3 | -1 | 1 |
| T2 | M9-1 | TTAEEAAGI SEQ ID NO: 3 | -10 | -5 | -5 | -4 |
| T2 | M9-2 | AAGIGILTV SEQ ID NO: 4 | 64 | 80 | 40 | 56 |
| T2 | M9-3 | GIGILTVIL SEQ ID NO: 5 | 18 | 20 | 0 | 10 |
| T2 | M9-4 | GILTVILGV SEQ ID NO: 6 | 1 | -1 | -3 | 2 |
| T2 | M9-5 | ILTVILGVL SEQ ID NO: 7 | -2 | -1 | -5 | -1 |
| T2 | M9-6 | LTVILGVLL SEQ ID NO: 8 | 1 | 0 | 1 | 0 |
| T2 | M9-7 | TVILGVLLL SEQ ID NO: 9 | -2 | -3 | -2 | 1 |
| T2 | M9-8 | VILGVLLLI SEQ ID NO: 10 | 1 | 5 | -2 | -2 |
| T2 | M9-9 | ALMDKSLHV SEQ ID NO: 11 | -1 | -4 | -8 | 0 |
| T2 | M9-10 | SLHVGTQCA SEQ ID NO: 12 | -1 | 1 | -8 | 4 |
| T2 | M9-11 | PVVPNAPPA SEQ ID NO: 13 | -2 | 0 | 4 | -1 |
| T2 | M9-12 | NAPPAYEKL SEQ ID NO: 14 | 1 | -2 | 0 | 6 |
| T2 | M10-1 | YTTAEEAAGI SEQ ID NO: 15 | -4 | -2 | -3 | 3 |
| T2 | M10-2 | TAEEAAGIGI SEQ ID NO: 16 | 7 | 11 | 12 | 15 |
| T2 | M10-3 | EAAGIGILTV SEQ ID NO: 17 | 55 | 66 | 31 | 51 |
| T2 | M10-4 | AAGIGILTVI SEQ ID NO: 18 | 34 | 68 | 29 | 21 |
| T2 | M10-5 | GILTVILGVL SEQ ID NO: 19 | -1 | 2 | 7 | 10 |
| T2 | M10-6 | ILTVILGVLL SEQ ID NO: 20 | 1 | 6 | 6 | 7 |
| T2 | M10-7 | LTVILGVLLL SEQ ID NO: 21 | -2 | -1 | -1 | 2 |
| T2 | M10-8 | TVILGVLLLI SEQ ID NO: 22 | -6 | -1 | -1 | 11 |
| T2 | M10-9 | RALMDKSLHV SEQ ID NO: 23 | 3 | 5 | 8 | 11 |
| T2 | M10-10 | SLHVGTQCAL SEQ ID NO: 24 | -2 | -8 | 2 | 9 |
| T2 | M10-11 | SLQEKNCEPV SEQ ID NO: 25 | 3 | 2 | 2 | 9 |

Twenty-three peptides (12 9-mers and 11 10-mers) (>90% purity) were synthesized and the lysability by TIL clone A42, TIL lines TIL1235, TIL660, and TIL1074 derived from different patients was tested against HLA-A2+ T2 cells preincubated with each peptide (10 ug/ml) in a 4h-$^{51}$Cr release cytotoxicity assay at E:T ratio of 20:1 for A42 and 40:1 for other TIL lines. T2 cells were lysed well when incubated with M9-2, M10-3 and M10-4. M10-3 and M10-4 contain the entire M9-2 sequence (underlined).

Recognition of MART-1 Peptides by HLA-A2 Restricted TIL Established from Different Patients To evaluate whether a variety of HLA-A2 restricted MART-1 specific TIL recognized the same or different epitopes in the MART-1 antigen, lysis of T2 cells (Cerundolo V., et al. (1990) *Nature* 345: 449-452) preincubated with each peptide was tested with TIL derived from 10 melanoma patients. A representative experiment with 10 TIL is shown in Table 6. M9-2 and M10-3 were recognized by 9 of 10 TIL (only TIL1200 were negative).as well as the A42 clone with the same pattern of lysis as COS7 cells cotransfected with cDNAs encoding MART-1 and HLA-A2.1. Only TIL620 and TIL1088 demonstrated low level of non-specific lysis of T2 cells without peptides or after the addition of irrelevant peptides, but showed significant increase of lysis of T2 cells preincubated with M9-2, M10-3, and M10-5 peptides. The recognition of M10-4 differed among the TIL, but was similar to the different reactivity to M10-4 by the T-cell clone A42 or the T-cell line TIL1235 (FIG. 2). Higher concentrations (1 ug/ml) of M10-4 were required for lysis than were required for M9-2 or M10-3. These 10 TIL and clone A42 also secreted cytokines including IFN-γ, GM-CSF and TNF-α when incubated with T2 cells preincubated with M9-2 or M10-3 (data not shown). Therefore, M9-2 or M10-3 are common epitopes recognized by a majority of HLA-A2 restricted melanoma specific TIL.

TABLE 6

Recognition of MART-1 peptides by HLA-A2 restricted melanoma specific TIL

| Target | Peptide (ug/ml) | TIL 501 | TIL 620 | TIL 660 | TIL 1074 | TIL 1088 | TIL 1128 | TIL 1143 | TIL 1200 | TIL 1235 | TIL 1363 | clone A42 |
|---|---|---|---|---|---|---|---|---|---|---|---|---|
|  |  |  |  |  |  | % specific lysis |  |  |  |  |  |  |
| 501mel | none | 42 | 49 | 35 | 32 | 31 | 19 | 24 | 41 | 32 | 43 | 41 |
| 397mel | none | 3 | 16 | 6 | 1 | 1 | 4 | 3 | 3 | 3 | 4 | 1 |

TABLE 6-continued

Recognition of MART-1 peptides by HLA-A2 restricted melanoma specific TIL

| Target | Peptide (ug/ml) | TIL 501 | TIL 620 | TIL 660 | TIL 1074 | TIL 1088 | TIL 1128 | TIL 1143 | TIL 1200 | TIL 1235 | TIL 1363 | clone A42 |
|---|---|---|---|---|---|---|---|---|---|---|---|---|
| | | | | | | % specific lysis | | | | | | |
| T2 | none | 0 | 7 | −3 | −6 | 7 | −6 | −7 | −6 | −7 | −7 | −6 |
| T2 | M9-1 (1) | 4 | 15 | −4 | 1 | 31 | 1 | −5 | −1 | 1 | 4 | 3 |
| T2 | M9-2 (1) | 86 | 75 | 73 | 79 | 98 | 30 | 36 | 2 | 92 | 82 | 91 |
| T2 | M9-2 (0.001) | 52 | 49 | 23 | 32 | 81 | 9 | 6 | 1 | 10 | 41 | 63 |
| T2 | M9-3 (1) | 5 | 25 | 0 | 1 | 19 | 0 | 1 | −2 | 0 | −2 | −4 |
| T2 | M10-2 (1) | 10 | 22 | 5 | 8 | 21 | 8 | 3 | 7 | 7 | 7 | 6 |
| T2 | M10-3 (1) | 84 | 68 | 68 | 73 | 79 | 24 | 27 | 1 | 42 | 67 | 62 |
| T2 | M10-3 (0.001) | 91 | 50 | 33 | 25 | 86 | 13 | 14 | 0 | 14 | 39 | 1 |
| T2 | M10-4 (1) | 83 | 47 | 16 | 35 | 80 | 6 | 3 | 1 | 14 | 53 | 0 |
| T2 | M10-4 (0.001) | 0 | 11 | 3 | 0 | 14 | 4 | −1 | −1 | 2 | −3 | −3 |
| T2 | M10-5 (1) | 4 | 14 | 1 | 4 | 13 | 2 | 3 | 0 | 3 | 0 | 2 |

Lysability by TIL clone A42 and TIL lines derived from 10 patients of T2 cells preincubated with the purified peptides M9-1, M9-2, M9-3, M10-2, M10-3, M10-4, and M10-5 was tested in a 4 h-$^{51}$Cr release assay at an E:T ratio of 20:1 for A42 and 40:1 for other TIL lines. Nine of ten TIL lysed T2 cells incubated with peptides M9-2 or M10-3. Seven of ten TIL lysed T2 incubated with peptide M10-4 at a concentration of 1 ug/ml.

The relative frequency of recognition of known melanoma proteins by T-cells derived from the TIL of ten melanoma patients has been examined. The common epitopes, M9-2 and M10-3 in the MART-1 antigen that were dominantly recognized by nine of these TIL have also been identified. The cDNA encoding MART-1 was isolated by cDNA expression cloning using TIL1235 in screening assays (See Example 1). MART-1 is a 118 amino acid protein containing a single transmembrane domain and is expressed in most melanoma cells as well as cultured melanocytes and retina similar: to the expression pattern of the cDNA for a form of gp100 described in Example 3. The gp100 is recognized by 4 of 10 TIL.

Based on dose response analysis, peptide M9-2 most effectively sensitized T2 cells for lysis (FIG. 2) suggesting that this peptide may be naturally processed and presented on tumor cells. The T-cells recognizing M9-2 may react with peptide M10-3 or M10-4 because the latter 10-mer peptides contain the 9 amino acid sequence of peptide M9-2. There is some difference in recognition of these 3 peptides by different TIL. For example, M10-4 was poorly recognized by the T-cell clone A42, but was well recognized by some TIL lines, although a higher concentration of M10-4 was necessary to observe the lysis. This may be due to the variation of TCR affinity for the M9-2 and M10-4 peptides in the context of HLA-A2, or alternatively, TIL lines may contain different T-cell clones which only recognize either M9-2 or M10-4. Peptides M10-3 and M10-4 may also be naturally processed and presented by tumor cells. The existence of multiple melanoma antigens presented by HLA-A2 has previously been suggested by analyzing the recognition of melanoma cell clones by a variety of T-cell clones (Knuth, A. et al. (1989), Proc. Natl. Acad. Sci. (USA) 86:2804, Wolfel, T. et al., 1989 J. Exp. Med. 170:797) or by analyzing HPLC peptide fractions that were isolated from HLA-A2 melanoma cells (Slingluff, C. L. Jr. et al., (1993) J. Immunol. 150:2955, Storkus; W. J. et al., (1993) J. Immunol. 151:3719).

The observation that most HLA-A2 restricted TIL from melanoma patients recognize common MART-1 peptides but not gp75 suggests that the M9-2 or M10-3 MART-1 peptides may be more immunogenic in inducing T-cell responses in vivo than other known melanoma antigens. Some of the TIL used in this study were injected along with IL2 into autologous patients, and interestingly, all 4 TIL (620, 660, 1074, 1200) that recognize a gp100 protein (FIG. 5A; SEQ ID NO: 27) effectively induced tumor regression (more than 50% reduction of tumor). All but TIL1200 also recognized MART-1.

EXAMPLE 3

Identification of a Second Human Melanoma Antigen Recognized by Tumor Infiltrating Lymphocytes Associated with in Vivo Tumor Rejection cDNA Expression Cloning The cDNA25 clone encoding a form of the melanoma antigen designated gp100 was cloned by techniques similar to those described in Example 1 and in Miki, T., et al. (1991) Proc. Natl. Acad. Sci. (USA) 88:5167-5171. Briefly, a breast cancer cell line, MDA231 (ATCC #HTB26), transfected with a cDNA library in λpCEV27 made from the 501mel melanoma cell line was screened for antigen positivity by measuring interferon-λ (IFN-γ) secretion when cocultured with TIL1200. TIL1200 was generated as described in Kawakami, Y., (1988), J. Exp. Med. 168, 2183-2191. The integrated cDNA was recovered from the genomic DNA of positive transfectants by PCR and cloned into the mammalian expression plasmid pcDNA3 (Invitrogen, San Diego, Calif.). The full length cDNA for cDNA25 was isolated from the 501mel λpCEV27 library using the cDNA25 probe. The λphage containing the full length cDNA25 was digested with XhoI, and then self-ligated with T4 DNA ligase to make the plasmid pCEV27-FL25. Alternatively, a full length cDNA25 isolated by PCR using the specific primers designed for gp100 was cloned in pCRII(Invitrogen), and then cloned into pcDNA3 (pcDNA3-FL25). To test whether this cDNA encoded a melanoma antigen it was retransfected into COS7, A375 or MDA231 and the resulting transfectants were tested for stimulation of TIL1200. DNA sequences of the plasmid clones were determined with an automated DNA sequencer (Model 373A; Applied Biosystems, Inc.), using the Taq DyeDeoxy terminator cycle sequencing kit (Applied Biosystems, Inc.) using the manufacturer's instructions.

Peptide Synthesis and Identification of Antigenic Peptides

Peptides were synthesized by a solid phase method using a Gilson AMS 422 multiple peptide synthesizer. The peptides were purified by HPLC on a Vydac C-4 column with 0.05%

TFA/water-acetonitrile. To identify antigenic peptides, TIL lysis of T2 RET-cells preincubated with peptides for 2 hour (h) was measured using a $^{51}$Cr release cytotoxicity assay.

Treatment of a Patient with Metastatic Melanoma Using TIL 1200

Figure 3A:
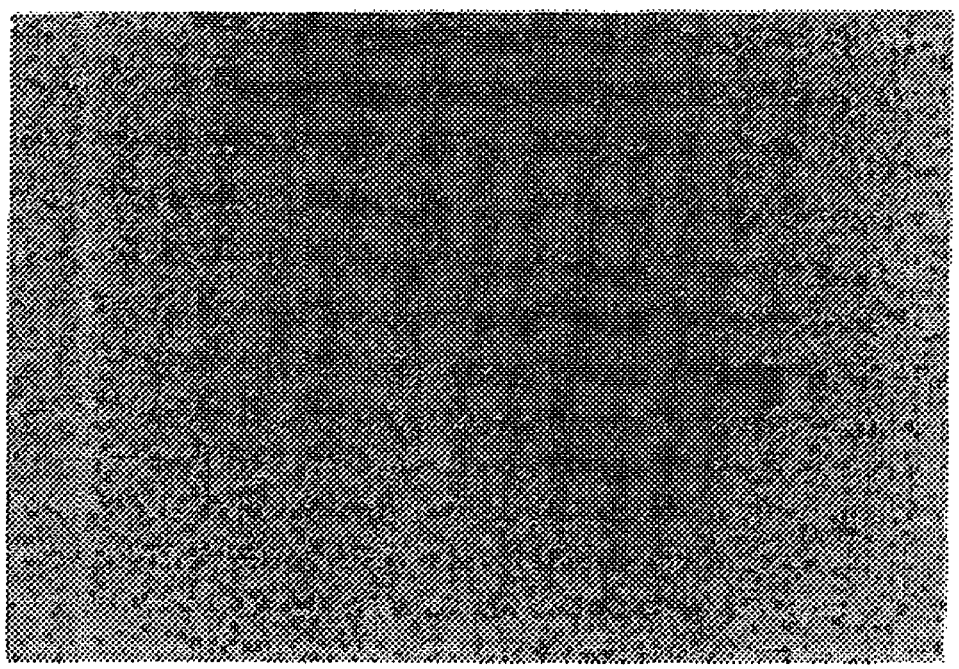
FIG. 3A shows a radionuclide scan of patient 1200 with metastatic melanoma after receiving the adoptive transfer of autologous $^{111}$In labeled TIL1200. The arrow indicates one of the areas of TIL accumulation corresponding to a metastatic lesion in the left thigh.
Figure 3B:
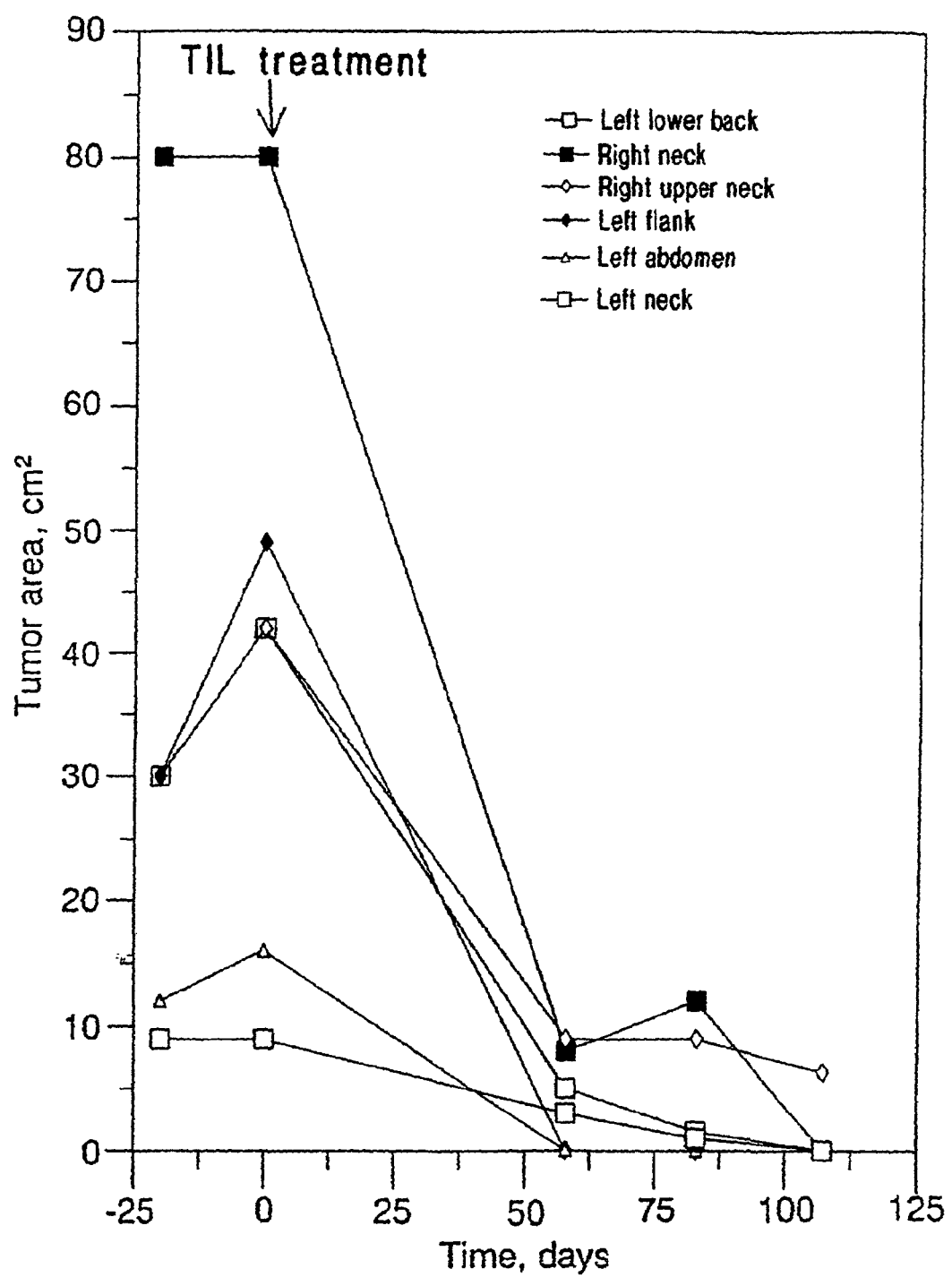
FIG. 3B shows regression of subcutaneous metastatic tumors following treatment with TIL1200 plus IL-2. Treatment began on day 0.

A 29 year old male patient, designated patient number 1200, with a widely metastatic melanoma who had previously failed chemotherapy and radiation therapy was treated with a single preparatory dose of 25 mg/Kg cyclophosphamide followed by the intravenous infusion of $1.6 \times 10^{11}$ TIL (including $9.1 \times 10^9$ Indium-ill labeled TIL) plus 7 doses of IL-2 at 720,000 IU/Kg given every 8 hours. A second cycle of treatment with TIL and IL-2 was given three weeks later. Radionuclide scans showed localization of TIL in rumor deposits (FIG. 3A). Biopsy of subcutaneous tumors on days 8 and 11 after treatment showed significant localization of TIL to tumor (ratios of injectate per gram in tumor compared to normal tissue were 14.9 and 14.0 respectively). The patient's cancer regressed rapidly following the first course of treatment. By three months after treatment 2 of 3 liver lesions had disappeared and a third lesion shrank by 50%. Multiple subcutaneous metastases regressed completely as shown in FIG. 3B (the product of perpendicular diameters of individual lesions are shown).

Characterization of in vitro function of TIL1200

A number of TIL lines established from HLA-A2$^+$ melanoma patients lysed melanoma cell lines in a class I MHC-restricted fashion (Kawakami, Y., et al. (1992) *J. Immunol.* 148; 638-643), and were shown to release IFNγ, tumor necrosis factor-alpha (TNFα) or granulocyte-macrophage colony stimulating factor (GM-CSF) when cocultured with the same tumor cell lines (Hom, S-S., et al. (1993) *J. Immunother.* 13; 18-30). A CD8$^+$ CTL line, TIL1200, established from a metastatic subcutaneous tumor mass of patient 1200, lysed fresh autologous melanoma cells as well as 10 of 15 HLA-A2$^+$ allogeneic melanoma cell lines, but did not lyse 16 of 18 HLA-A2$^-$ melanoma cell lines or 6 of 8 HLA-A2$^+$ non-melanoma cell lines (Shilyansky, J., et al. (1993) *Proc. Natl. Acad. Sci. USA*, 91, 2829-2833, unpublished data). Table 7 shows a cytotoxicity assay against 5 representative HLA-A2$^+$ melanoma cell lines that were lysed by TIL1200, 4 representative HLA-A2+ melanoma cell lines that were not lysed by TIL1200, and one HLA-A2$^-$ melanoma cell line. TIL1200 also secreted IFN-γ when cocultured with HLA-A2$^+$ normal cultured melanocytes established from neonatal foreskin as well as HLA-A2$^+$ melanoma cell lines (Table 8). Therefore, TIL1200 appeared to recognize a non-mutated self peptide expressed in most melanomas and cultured neonatal melanocytes in an HLA-A2 restricted fashion.

Cloning of the cDNA Coding for a Melanoma Antigen Recognized by T Cells

A cDNA library in λ pCEV27 from the HLA-A2$^+$ 501mel melanoma cell line, which was lysed by most HLA-A2 restricted melanoma specific TIL, was stably transfected into the highly transfectable HLA-A2$^+$ melanoma antigen negative MDA231 clone 7 or A375 clone 1-4. G418 resistant cells were selected and approximately 6700 individual transfectants from each cell line were isolated and screened based on their ability to stimulate IFN-γ secretion from TIL1200. Six DNA fragments were isolated by PCR using SP6/T7 primers flanking the integrated DNA from four MDA231 and one A375 transfectants that were positive in a second screening and were cloned into the mammalian expression vector pcDNA3 (Invitrogen).

These fragments in the pcDNA3 vector were transiently expressed in the COS7 cells with or without pcDNA3-HLA-A2.1. Transfection into COS7 of one of the cDNAs tested, cDNA25, along with HLA-A2.1 reproducibly conferred the ability to stimulate secretion of IFN-γ from TIL1200. The stable transfection of cDNA25 into A375 also stimulated IFN-γ release from TIL1200 (Table 9, Exp.1 and Exp. 2). A 2.2 Kb band detected by Northern blot analysis of the melanoma using the cDNA25 probe suggested that the cloned 1.6 Kb fragment was not a full length cDNA. Comparison with the GenBank database of the consensus DNA sequence of

TABLE 7

Specificity of Antigen Recognition by TIL1200:
Lysis of HLA-A2$^+$gp100$^+$ Melanoma Cell Lines

| Target | HLA-A2 | gp100 | | TIL1200 | LAK |
| | | FACS | Northern | (% specific lysis) | |
|---|---|---|---|---|---|
| 501mel | + | + | + | 46 | 78 |
| 526mel | + | + | + | 39 | 74 |
| 624mel | + | + | + | 33 | 76 |
| 952mel | + | + | + | 25 | 76 |
| Malme3M | + | + | + | 43 | 70 |
| C32 | + | − | −/+* | 6 | 82 |
| RPMI7951 | + | − | − | 9 | 67 |
| WM115 | + | − | − | 5 | 68 |
| HS695T | + | − | − | 3 | 87 |
| 397mel | − | + | + | 0 | 70 |

5 hour (h) $^{51}$Cr release assay was performed to measure cellular cytotoxicity at an effector: target ratio of 40:1 as previously described(Kawakami, Y. et al. (1988) J. Exp. Med. 168: 2183-2191). The expression of HLA-A2 and gp100 recognized by monoclonal antibody HMB45 (Enzo Diagnostics, New York, NY) was measured by flow cytometry(FACS). The expression of gp100 RNA was analyzed by Northern blot with a cDNA25 probe.
*−/+ indicates very weak positive.

TABLE 8

Specificity of Antigen Recognition by TIL1200:
Recognition of HLA-a-a2$^+$ Neonatal Melanocytes

| Stimulator | HLA-A2 | TIL1200 | TIL888 |
| | | (pgIFN-γ/ml) | |
|---|---|---|---|
| 501mel | + | 562 | 0 |
| 624mel | + | 439 | 0 |
| 397mel | − | 0 | 0 |
| 888mel | − | 0 | 1970 |
| NHEM493 | − | 441 | 0 |
| NHEM527 | + | 418 | 0 |
| NHEM530 | + | 164 | 0 |
| NHEM616 | + | 53 | 0 |
| FM725 | + | 107 | 0 |
| FM801 | + | 250 | 343 |
| NHEM483 | − | 0 | 0 |
| NHEM680 | − | 0 | 0 |
| HA002 | − | 0 | 0 |

The IFN-γ secretion by TIL was measured by ELISA as previously described in Example 1. The amount of IFN-γ secreted by TIL alone was subtracted (88 pg/ml for TIL888 and none for TIL 1200). TIL888 is a class I MHC restricted melanoma specific CTL, not restricted by HLA-A2. NHEM, FM, and HA refer to normal cultured melanocyte cell lines, all others are melanoma cell lines.

TABLE 9

Transfection of cDNA 25 into A375 and COS7

| | Stimulator cells | Transfected genes | HLA-A2 | Secretion by TIL1200 (pgIFNγ/ml) |
|---|---|---|---|---|
| Exp. 1 | 501mel | none | + | 987 |
| | 397mel | none | − | 0 |
| | A375 | none | + | 0 |
| | A375 | pcDNA3-25 | + | 230 |
| Exp. 2 | 501mel | none | + | 662 |
| | 397mel | none | − | 0 |
| | COS7 | none | − | 0 |
| | COS7 | HLA-A2.1 | + | 0 |
| | COS7 | pcDNA3-25 | − | 0 |
| | COS7 | HLA-A2.1+pcDNA3-25 | + | 310 |
| Exp. 3 | 501mel | none | + | 908 |
| | 397mel | none | − | 0 |
| | COS7 | none | − | 0 |
| | COS7 | HLA-A2.1 | + | 0 |
| | COS7 | pCEV27-FL25 | − | 0 |
| | COS7 | HLA-A2.1+pCEV27-FL25 | + | 742 |
| | COS7 | pcDNA3-FL25 | − | 0 |
| | COS7 | HLA-A2.1+pcDNA3-FL25 | + | 801 |

TIL 1200 secreted IFN-γ when coincubated with HLA-A2⁺ A375 stably transfected with pcDNA3 containing truncated cDNA25 (pcDNA3-25) (Exp. 1) or COS7 transiently transfected with either pcDNA3-25 (Exp. 2), pcDNA3 containing full length cDNA25 (pcDNA3-FL25) or pCEV27 containing full length cDNA25 (pCEV27-FL25) (Exp. 3) along with pcDNA3 containing HLA-A2.1 (HLA-A2.1). HLA-A2 expression was determined by flow cytometry and interferon-gamma secretion was measured by ELISA.

3 cDN25 clones that were independently amplified by PCR revealed that cDNA25 was distinct from two previously registered genes, a gp100 (GenBank Access No. M77348) and Pmel17 (Kwon, B. S., et al. (1991) *Proc. Natl. Acad. Sci*, USA 88, 9228-9232). The cDNA 25 differed from the gp100 in GenBank (Accession No. M77348, also known as gp95) by two nucleotides, from the PMEL 17 sequence (Kwon et al. (1991) *Proc. Natl. Acad. Sciences* (USA) 58: 9228-9232) by 3 bases and a 21 base pair deletion. (FIG. 5B).

The full length cDNA25(FL25) was isolated in two plasmids, pCEV27-FL25 or pcDNA3-FL25. Transfection of either plasmid into COS7 along with pcDNA3-HLA-A2.1 conferred to COS7 the ability to induce IFN-γ secretion by TIL1200. The amount of IFN-γ secretion stimulated by COS7 transfected with the full length DNA plus HLA-A2.1 was similar to that stimulated by 501mel and was higher than that stimulated by COS7 transfected with the truncated cDNA25 possibly due to improved translation starting at the normal AUG initiation codon (Table 9, Exp.2 and 3). Alternatively, the 5' region missing from the truncated cDNA25 may contain other epitopes recognized by clones in TIL1200. The requirement for HLA-A2.1 expression for IFN-γ release from TIL1200 and the fact that transfected cells did not stimulate IFN-γ secretion from irrelevant TIL (data not shown) demonstrated that the cDNA25 encoded an antigen recognized by TIL1200 in the context of HLA-A2.1 and did not encode a molecule that non-specifically induced IFN-γ release from T cells.

The nucleotide and corresponding amino acid sequences of the truncated cDNA 25 and the full length cDNA25 cloned from the 501mel cDNA library by screening with the cDNA25 probe (FIG. 5A) were compared with the GenBank sequences of Pmel17 isolated from normal melanocytes and gp100 isolated from the melanoma cell line MEL-1. (FIG. 5B). The full length cDNA25 differed from the gp100 amino acid sequence at position 162. This amino acid difference is possibly caused by polymorphism or mutation in the tumor. cDNA25 had 2 amino acid differences at positions 162 and 274, compared to Pmel17 and did not contain 7 amino acids that existed in Pmel17 at positions 588-594. The amino acid sequence of the truncated cDNA25 that was isolated from the original MDA231 transfectant has a different sequence at the 3' end (from position 649 to the end) due to a frame shift caused by one extra cytidylic acid. It is not clear whether this difference was due to a true allelic difference or to a mutation that occurred during manipulation of the DNA. Nevertheless, TIL1200 appeared to recognize non-mutated peptides located between position 236 and 648. cDNA25 also had 87% similarity in amino acid sequence to cDNA RPE1 (Kim, R., and Wistow, G. J. (1992) *Exp. Eve Res.* 55: 657-662) specifically expressed in bovine retinal pigment epithelium and 60% similarity to cDNA MMP115 that encoded a melanosomal matrix protein isolated from chicken pigmented epithelial cells (Shilyansky, J., et al. (1993) *Proc. Natl. Acad. Sci, USA*, 91, 2829-2833).

A gp100 protein was known to be recognized by monoclonal antibody HMB45 (Adema et al., (1993) *Am. J. Patholoay*, 143: 1579-1585). COS7 cells transfected with the full length cDNA25 were evaluated by flow cytometry using this monoclonal antibody. After transient expression of either pCEV27-FL25 or pcDNA3-FL25, COS7 expressed the antigen detected by HMB45 (data not shown).

Expression of RNA for cDNA25

Figure 6A:
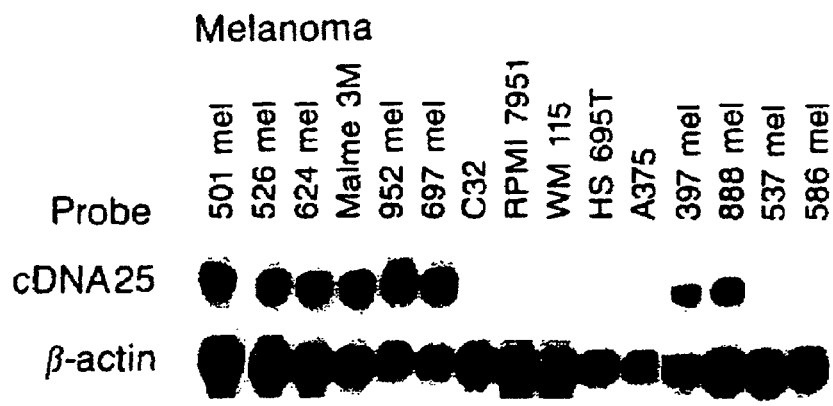
FIG. 6 shows northern blot analysis of melanoma and neonatal melanocyte cell lines and various fresh tissues (10-20 μg of total RNA) with a cDNA25 probe(the Sal I digested fragment of pCRII-cDNA25) and the β-actin probe(Clontech). C32, 586mel melanoma cell lines and NHEM529, NHEM530 neonatal melanocyte cell lines were very weak positive.
Figure 6B:
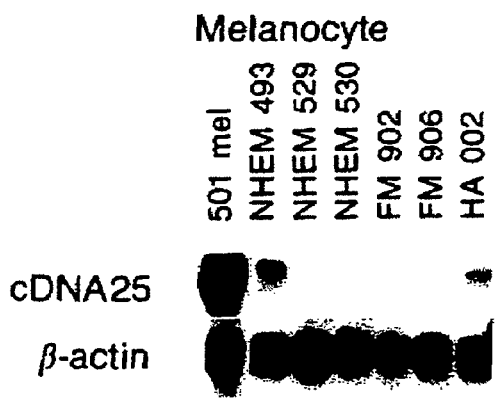
Figure 6C:
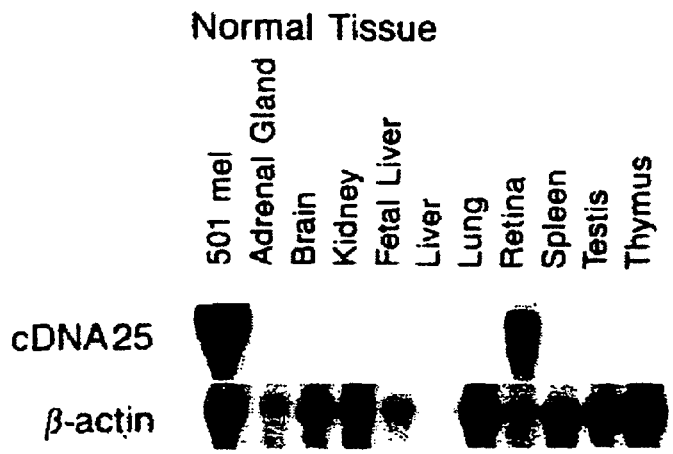

Northern blot analysis was performed with the cDNA25 probe to evaluate the tissue specific expression of this gene. Ten of 15 melanoma cell lines and 6 of 6 melanocyte cell lines were positive for cDNA 25. Of many normal tissues tested only retina was positive (FIG. 6). Seven cell lines from T-cell (TILA, B), B-cells (501EBVB, 836EBVB) and fibroblast (M1) and 20 non-melanoma tumor cell lines (colon cancer, Collo, SW480, WiDr; breast cancer, MDA231, MCF7, HS578, ZR75; neuroblastoma, SK—N-AS, SK—N—SH; Ewing sarcoma, TC75, RD-ES, 6647; sarcoma 143B; glioma, U138MG, HS683; renal cell cancer, UOK108, UOK117, small cell lung cancer, H1092; Burkitt's lymphoma, Daudi; myeloma HMY) were all negative for cDNA25 (data not shown). Therefore, this gene appeared to be specifically expressed in melanocyte lineage cells, consistent with the expression pattern of previously isolated forms of gp100 when analyzed using monoclonal antibodies, HMB45, NKI/betab, or HMB-50 (Adema, G. J., et al. (1993) *Am J Pathology* 143: 1579-1585; Gown, A. M., et al., (1986) *Am J Pathol* 123:195-203; Colombari, R., et al. (1988) *Virchows Archiv A Pathol Anat.* 413:17-24); Vennegoor, C., et al. (1988) *Am. J. Pathol.* 130:179-192; Vogel, A. M., and Esclamado R. M. (1988) *Cancer Res.* 48:1286-1294). The levels of expression of the RNA detected by the cDNA25 probe in cultured neonatal melanocyte cell lines was significantly lower than that in melanoma cell lines. There was a perfect correlation between gp100 expression detected by Northern blot analysis with cDNA25 and flow cytometry using HMB45 antibody and melanoma lysis by TIL1200 in the 10 HLA-A2⁺ melanoma cell lines as shown in Table 7.

Identification of the Epitope in gp100

Based on a comparison of the amino acid sequence of the truncated form of cDNA 25 to known binding motifs of HLA-A2.1 (Falk, K., et al. (1992) *Nature* 351:290-296; Hunt, D. F., et al. (1992) *Science* 255:1261-1263; Ruppert, J., et al. (1993) *Cell* 74:929-9937,) 30 peptides of 9 or 10 amino acids in length from cDNA25 were synthesized. TIL1200 lysed the HLA-A2⁺ cell line, T2, only when incubated with the peptide LLDGTATLRL (SEQ ID NO: 27 residues 457-486. FIG. 5A;

SEQ ID NO: 33) but not when incubated with the other 29 peptides (Table 10, FIG. 5A). Only peptide LLDGTATLRL (SEQ ID NO: 33) was able to also stimulate IFN-γ secretion by TIL 1200 (data not shown).

Many melanoma-specific CTL derived from TIL appear to recognize non-mutated self peptides derived from melanocyte-melanoma lineage specific proteins, since these TIL recognize most melanoma cell lines and normal cultured melanocytes sharing the appropriate restriction element. (Anichini, A., et al. (1993) J. Exp. Med. 177:989-998; Kawakami, Y., et al. (1993) J. Immunother. 14:88-93). In an attempt to isolate and identify melanoma antigens of value in the immunotherapy of melanoma patients, TIL, TIL1200 were used that, when transferred into a patient with metastatic cancer, localized to the tumor site and was associated with a dramatic tumor regression. It has been shown that, in contrast to non-activated lymphocytes and lymphokine activated killer cells, autologous TIL localize to tumor sites. This localization correlated with the ability of these TIL to mediate tumor regression (data not shown). TIL1200 which was a TIL line containing multiple CTL species recognized a tumor antigen in the context of HLA-A2, which is the most frequently expressed class I MHC antigen (about 50% of individuals) and has been shown to be a dominant restriction element for the induction of melanoma specific CTL. (Crowley, N. J., et al. (1991) J. Immunol. 146, 1692-1699).

By cDNA expression cloning using T cell recognition for screening, a cDNA (FIG. 4; SEQ ID NO: 26) encoding an antigen recognized by TIL1200 and identified as a form of gp100, a membrane glycoprotein also recognized by monoclonal antibodies, BMB45, HMB50 or NKI/betab has been identified. (Adema, G. J., et al. (1993) Am J Pathology 143, 1579-1585. Gown, A. M., et al. (1986) Am J Pathol 123, 195-203. Colombari, R., et al. (1988) Virchows Archiv A Pathol Anat. 413, 17-24; Vennegoor, C., et al. (1988) Am. J. Pathol. 130, 179-192; Vogel, A. M., and Esclamado R. M. (1988) Cancer Res. 48, 1286-1294). These antibodies are highly specific for melanocyte lineage tissues and strongly stain most melanoma cells. NKI/betab also reacts with adult melanocytes in normal skin (Vennegoor, C., et al. (1988)

TABLE 10

TIL1200 Lysis of the T2 HLA-A2+ Cell Line Pulsed with the Peptide, LLDGTATLRL

| Target | HLA-A2 | Peptide* (ug/ml) | TIL1200 | TIL1235+ |
|---|---|---|---|---|
| | | | (% specific lysis)** | |
| 501mel | + | 0 | 66 | 51 |
| 397mel | − | 0 | 1 | 0 |
| T2 | + | 0 | 2 | 1 |
| T2 | + | 40 | 28 | ND++ |
| T2 | + | 10 | 32 | 0 |
| T2 | + | 1 | 24 | ND |
| T2 | + | 0.1 | 6 | ND |
| T2 | + | 0.01 | 0 | ND |
| T2 | + | 0.001 | 2 | ND |

*TIL1200 lysed T2 cells pulsed with the 10-mer peptide, LLDGTATLRL(457-466), but not other 29 peptides SEQ ID NO: 27 (residues 273-281, 297-306, 373-381, 399-407, 399-408, 409-418, 456-464, 463-471, 465-473, 476-485, 511-520, 519-528, 544-552, 544-553, 570-579, 576-584, 576-585, 585-593, 592-600, 597-605, 597-606, 602-610, 602-611, 603-611, 605-614, 606-614, 606-615, 619-627, 629-638)
+TIL1235 is an HLA-A2 restricted melanoma specific CTL that does not recognize gp100.
**E:T of 50:1
++ND, not done.

Am. J. Pathol. 130, 179-192) Immunoelectron-microscopic studies using either HMB45 or NKI/betab antibody revealed that a gp100 protein was mainly located in a membrane and filamentous matrix of stage I and II melanosomes in the cytoplasm (Vennegoor, C., et al. (1988) Am. J. Pathol. 130, 179-192; Schaumburg-Lever, G., et al. (1991) J. Cutan. Pathol. 18, 432-435). By a completely independent procedure, a cDNA encoding another form of gp100 was also isolated by screening with a rabbit polyclonal antiserum against gp100 (Adema, G. J., et al. (1993) Am J Pathology 143:1579-1585) and TIL1200 also lysed HLA-A2+ cell lines transfected with this cDNA clone (Bakker, A. B. H. et al. (1994) J. Exp. Med. 179:1005-1009).

The existence of T cells reactive to the self-antigen gp100 in tumors and the possible enrichment of these T cells at the tumor site as a possible consequence of the specific accumulation and expansion of antigen reactive cells (Sensi, M. et al., (1993) J. Exp. Med 178:1231-1246) raises important questions about the nature of the immune response to self antigens on growing cancers and about the mechanisms of immunologic tolerance to self-antigens. The increased expression of gp100 on melanoma cells relative to that in melanocytes demonstrated by Northern blot analysis or the unique inflammatory conditions that might exist at the tumor site, which may be associated with the secretion of cytokines and expression of costimulatory molecules on the cell surface, could break tolerance to gp100. Depigmentation has been reported to be associated with a good prognosis (Nordlund, J. J., et al. (1983) J. Am. Acad. Dermatol. 9:689-695; Bystryn, J-C, et al. (1987) Arch. Dermatol., 123:1053-1055) and with clinical response to chemoimmunotherapy (Richards, J. M., et al. (1992) J. Clin. Oncol. 10:1338-1343) in melanoma patients. Sporadic vitiligo in has been seen patients receiving melanoma-specific TIL but adverse ophthalmologic effects that might be related to melanocyte destruction has not been observed. Patient 1200 did not develop vitiligo or any ophthalmologic side-effects.

The gp100 protein (FIG. 5A; SEQ ID NO: 27) and the ten amino acid peptide identified may represent a human tumor rejection antigen since the transfer into patient 1200 of TIL1200 plus IL2 was associated with cancer regression. The traffic of TIL1200 to tumor deposits in vivo and the rapidity of the antitumor response are characteristics of the response to TIL therapy, although IL2 may also have been involved in the tumor rejection. Adoptive transfer of 3 other TIL lines which recognized gp100 as well as MART-1 also mediated tumor regression (data not shown).

Tyrosinase (Brichard, V., et al. (1993) J. Exp. Med. 178, 489-495) and MART-1 (see Example 1) have been identified as melanoma antigens recognized by HLA-A2 restricted CTL. Another antigen, MAGE-1 is recognized by HLA-A1 restricted melanoma-specific CTL and is expressed on a variety of cancer cells as well as testis (Van Der Bruggen, P. et al. (1991) Science, 254:1643-1647). However, none of the ten HLA-A2 restricted TIL recently developed appeared to recognize MAGE-1 (Zakut, R., et al. (1993) Cancer Res. 53: 5-8).

The wide expression of gp100 proteins in melanomas, the recognition of a peptide by T cells infiltrating into tumor, its restriction by HLA-A2, present in 50% of individuals, and the association of anti gp100 reactivity with cancer regression in patient 1200 imply that the gp100 antigen in particular the novel immunogenic peptides derived from the gp100 amino acid sequence (FIG. 5A; SEQ ID NO: 27) may be particularly useful for the development of active immunotherapies for patients with melanoma.

EXAMPLE 4

Recognition of Multiple Epitopes in Human Melanoma Antigen by TIL Associated with in Vivo Tumor Recognition Materials and Methods Generation of CTL from TIL and Treatment of Patients with Metastatic Melanoma Melanoma specific CTL were induced and expanded from TIL in media containing 6000 IU/ml of IL2 as previously described (Kawakami, et al., (1988) *J. Exp. Med.* 168:2183). All available HLA-A2 restricted melanoma specific CTL which were administered to autologous patients in the Surgery Branch, NCI, were used in this study. TIL were administered intravenously along with IL2 into autologous patients with metastatic melanoma as previously reported (Rosenberg, S. A., et al., (1988) *N Engl J Med* 319:1676; Rosenberg S. A., et al., (1994) *J. NCI.* 86:1159). Fisher's exact test was used to determine the association of gp100 recognition by TIL with clinical response to TIL treatment; likewise with MART-1 recognition.

Synthesis of Peptides

Peptides were synthesized by a solid phase method using a peptide synthesizer (model AMS 422;Gilson Co.Inc., Worthington, Ohio)(>90% purity). The peptides to be synthesized were selected from the reported human sequence of gp100 based on HLA-A2.1 binding motifs (Falk, K., (1991) *Nature* 351:290; Hunt, D. F., et al, (1992) *Science* 255:1261; Ruppert, J., et al., (1993) *Cell* 74:929; Kubo, R T, et al. (1994) *J Immunol.* 152:3913). The following peptides were tested: Eight 8-mer peptides (with residues starting at −199, 212, 218, 237, 266, 267, 268, 269; see FIG. 7A), eighty-four 9-mer peptides with residues starting at −2, 4, 11, 18, 154, 162, 169, 171, 178, 199, 205, 209, 216, 241, 248, 250, 255, 262, 266, 267, 268, 273, 278, 280, 273, 286, 287, 296, 290, 309, 316, 332, 335, 350, 354, 358, 361, 371, 373, 384, 389, 397, 399, 400, 402, 407, 408, 420, 423, 425, 446, 449, 450, 456, 463, 465, 485, 488, 501, 512, 536, 544, 563, 570, 571, 576, 577, 578, 583, 585, 590, 592, 595, 598, 599, 601, 602, 603, 604, 606, 607, 613, 619, 648; see FIG. 7A) and seventy-seven, 10-mer peptides with residues starting at −9, 17, 57, 87, 96, 154, 161, 169, 177, 197, 199, 200, 208, 216, 224, 232, 240, 243, 250, 266, 267, 268, 272, 285, 287, 289, 297, 318, 323, 331, 342, 350, 355, 357, 365, 380, 383, 388, 391, 395, 399, 400, 406, 407, 409, 415, 432, 449, 453, 457, 462, 476, 484, 489, 492, 511, 519, 536, 543, 544, 548, 568, 570, 571, 576, 577, 584, 590, 595, 598, 599, 601, 602, 603, 605, 611, 629; see FIG. 7A) were synthesized. Possible epitopes identified in the first screening were further purified by HPLC on a C-4 column (VYDAC, Hesperia, Calif.)(>98% purity) and the molecular weights of the peptides were verified by mass spectrometry measurement as previously described (Example 3; Kawakami, Y., et al., (1994) *J. Exp. Med.* 180:347; Kawakami, Y., et al., (1994) *Proc Natl Acad Sci* (USA) 91:6458).

Peptide Binding Assay to HLA-A2.1

Soluble HLA-A2.1 heavy chain, human beta 2-microglobulin, radiolabeled peptide $HBc_{18-27}$ (FLPSDYFPSV) and various concentrations of the sample peptides were coincubated in the presence of protease inhibitors for 2 days at room temperature as previously described (Ruppert, J., et al., (1993) *Cell* 74:929; Kubo, R T, et al., (1994). *J Immunol.* 152:3913; Sett A., et al., (1994). *Molecular Immunol.* 31:813). The percentage of labeled peptide bound to HLA-A2.1 was calculated after separation by gel filtration and the concentration of the sample peptide necessary to inhibit 50% of the binding of the labeled peptide was calculated. The relative affinity of peptides to HLA-A2.1 were also calculated as a ratio (concentration of the standard $HBc_{18-27}$ peptide to inhibit 50% of the binding of the labeled peptide/concentration of the sample peptide to inhibit 50% of the binding of the labeled peptide) as previously described (Sett A., et al., (1994) *Molecular Immunol.* 31:813). Peptide binding was defined as high (50% inhibition at <50 nM, ratio>0.1), intermediate (50-500 nM, ratio 0.1-0.01) or weak (>500 nM, ratio<0.01) (Ruppert, J., et al., (1993) *Cell* 74:929; Kubo, R T, et al., (1994) *J Immunol.* 152:3913; Sett A., et al., (1994) *Molecular Immunol.* 31:813).

The pcDNA3 plasmid containing the full length gp100 cDNA (FIG. 4, Example 3; Kawakami, Y., et al., (1994)). *Proc Natl Acad Sci* (USA) 91:6458) was digested with Xho I and Xba I. After incorporation of alpha-phosphorothioate deoxynucleoside triphosphate into the Xba I site, a standard exonuclease III nested deletion was performed using the Exo Size Deletion Kit (New England Biolabs, inc., Beverly, Mass.). The deleted clones were self-ligated and amplified. The exact deletion for each clone was confirmed by DNA sequencing. To identify the region containing epitopes, pcDNA3 plasmids (Invitrogen, San Diego Calif.) containing the cDNA fragments (D3, D5, D4, C3) generated by the sequential deletion with exonuclease from the 3' end of the full length gp100 cDNA as well as the truncated gp100 cDNA lacking the 5'-coding region (25TR) (Example 63; Kawakami, Y. (1994) *Proc Natl Acad Sci* (USA) 91:6458), were transfected into COS7 cells along with the HLA-A2.1 cDNA and the recognition of the transfected COS cells by TIL was evaluated using IFN-γ release assays (Example 1; Kawakami, Y., (1994) *Proc Natl Acad Sci* (USA) 91:3515).

Evaluation of Antigen Recognition by T-Cells

To assess antigen recognition by T-cells, a $^{51}Cr$ release assay or an IFN-γ release assay were performed as previously described (Examples 1 and 2; Kawakami, Y., et al., (1994)). *Proc Natl Acad Sci* (USA) 91:3515; Kawakami, Y., et al., (1988). *J. Exp. Med.* 168:2183). Either COS7 cells transfected with cDNA encoding melanoma antigens and HLA-A2.1 cDNA, or T2 cells preincubated with peptides were used as stimulators for the IFN-γ release assay. T2 cells pulsed with peptides were also used as targets for cytotoxicity assays (Kawakami, Y., (1994) *J. Exp. Med.* 180:347).

Recognition of gp100 by TIL Correlated with Clinical Response to TIL Treatment

Four of 14 HLA-A2 restricted melanoma specific CTL derived from TIL recognized gp100 while 13 recognized MART-1 (3 recognized both gp100 and MART-1). None recognized tyrosinase or gp75 as assessed by the reactivity of TIL against COS7 cells transfected with the cDNA encoding these melanoma antigens along with HLA-A2.1 cDNA (Example 2; Kawakami, Y et al. (1994) *J. Exp. Med.* 180:347). The HLA-A2 restriction and the recognition specificity of these 4 gp100 reactive CTL has been previously demonstrated (Examples 1-3; Kawakami, Y., et al., (1994) *Proc Natl Acad Sci* (USA) 91:6458; Kawakami, Y., et al., (1992) *J Immunol* 148:638; O'Neil, B. H., et al., (1993) *J Immunol* 1410:1418; Shilyansky, J., et al., (1994) *Proc. Natl. Acad. Sci.* (USA) 91:2829). Ten of these 14 CTL were administered into the autologous patients along with IL2. As summarized in Table 11, all 4 patients treated with CTL capable of recognizing gp100 resulted in an objective partial response (>50% tumor regression). Clinical response to TIL therapy associated with reactivity of TIL to gp100 (p=0.0048) but not to MART-1 (p=0.4). These data suggested that gp100 may contain epitopes capable of mediating in vivo tumor regression.

Identification of Epitopes Recognized by gp100 Reactive TIL

To identify the epitopes recognized by these 4 gp100 reactive CTL, a 169 peptides which contained HLA-A2.1 binding motifs were synthesized. Peptide recognition was evaluated by testing the reactivity of these CTL against HLA-A2.1+ T2 cells preincubated with each peptide using both cytotoxicity and IFN-γ release assays. As shown in Table 12, 7 peptides were recognized by gp100 reactive TIL in the cytotoxicity assays. The results of the IFN-7 release assays performed at the same time were consistent with that of the cytotoxicity assays. The different subcultures of TIL620 (620-1, 620-2) or TIL660 (660-1, 660-2, 660-3) were grown from the TIL culture that was administered into the autologous patient, but they were separately cultured and had slightly different specificities likely due to the in vitro expansion of different clones. $G9_{209}$ (ITDQVPFSV) (SEQ ID NO:48) and $G10_{209}$ (TITDQVPFSV) (SEQ ID NO:49), which has an extra threonine at the N-terminus of $G9_{209}$, were recognized only by TIL620. $G9_{154}$ (KTWGQYWQV) (SEQ ID NO:46) and $G10_{154}$ (KTWGQYWQVL) (SEQ ID NO:47), which has an extra leucine at the C-terminus of $G9_{154}$, were recognized by TIL1200, TIL620-2 and TIL660-2. G10-4 (LLDGTATLRL) (SEQ ID NO:33) was recognized by TIL1200 as demonstrated (Example 3). The peptide $G9_{280}$ (YLEPGPVTA) (SEQ ID NO:40) was recognized by TIL660 and TIL1143. TIL660-3 also recognized G10-5 (VLYRYGSFSV) (SEQ ID NO:34) as well as G9280. Lysis of T2 cells preincubated with G10-5 was repeatedly low, possibly because a small subset of T-cell clones was specific for this epitope.

To complement the epitope identification using the known HLA-A2.1 binding motifs, another method was also used to identify regions possibly containing epitopes. Five gp100 cDNA fragments, 4 generated by exonuclease deletion from the 3'-end of the cDNA (D3, D4, D5, C4) as well as a partial cDNA clone lacking the first 705 base pairs of the 5'-coding region (25TR), were inserted into the pcDNA3 plasmid and transfected into COS7 cells along with the HLA-A2.1 cDNA. The locations of the fragments are shown in FIG. 7A. The recognition of these transfectants by the 4 gp100 reactive TIL was evaluated using an IFN-γ release assay (FIG. 7B). TIL 1200 recognized COS cells transfected with the fragments, 25TR, D5, D4 or C4, but not with D3, suggesting that at least 2 epitopes existed in the regions of amino acid residues 146-163 and 236-661. $G9_{154}$ and $G10_{154}$ were the only peptides which contained HLA-A2.1 binding motifs in the region 146-163 and both were recognized by TIL1200. G10-4 was located in the region 236-661 and was recognized by TIL1200. TIL620-1 recognized COS cells transfected with C4 but not with D3, D5, D4 or 25TR, suggesting that the epitope existed within residues 187-270. $G9_{209}$, and $G_{10208}$ which were recognized by TIL620-1 were located in this region. TIL620-2, another subculture of TIL620, also recognized COS cells transfected with D5 and D4, but not D3, and recognized $G9_{154}$ and $G20_{154}$ in the region 147-163, also recognized by TIL1200. TIL660-1 and TIL1143 recognized COS cells transfected with C4 or 25TR, but not with D3, D5, or D4, suggesting that epitopes existed in the 2 regions 187-270 and 236-661. $G9_{280}$ located in the fragment 25TR, but not in the fragment C4, was recognized by TIL660 and TIL1143.

Binding Affinity of the Melanoma Epitopes to HLA-A2.1 in Vitro

Figure 8A:
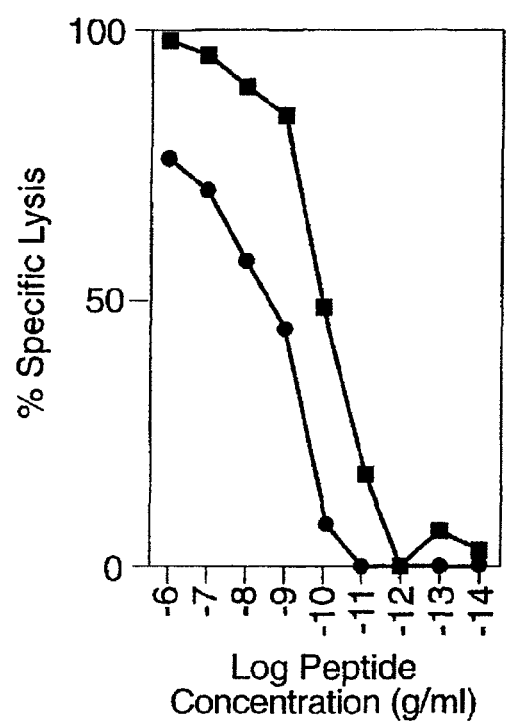
FIGS. 8A-8D show titration of gp100 epitopes by sensitization of HLA-A2.1+ T2 cells for CTL lysis. Lysis of T2 cells preincubated with peptides was tested in a 4h $^{51}$Cr release cytotoxicity assay.
Figure 8B:
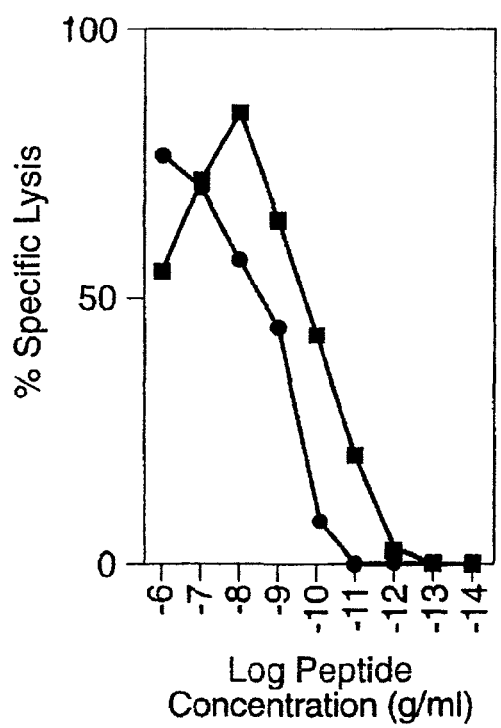
Figure 8C:
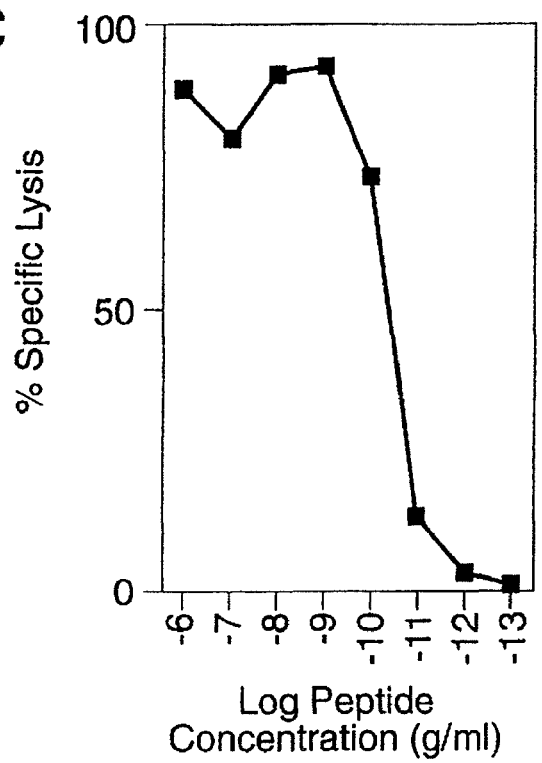
Figure 8D:
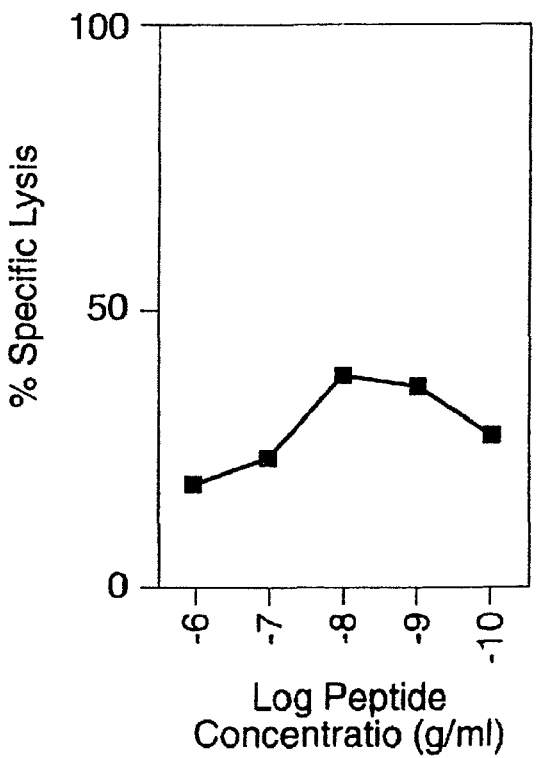

With the exception of G10-4, which required a concentration of 1 ug/ml to sensitize T2 cells for CTL lysis (Example 3; Kawakami, Y., et al., (1994) *Proc Natl Acad Sci (USA)* 91:6458), all gp100 epitopes identified in this study could sensitize T2 cells for CTL lysis at a concentration of 1 ng/ml (FIGS. 8A-8D). G10-5 appeared to be inhibitory to the cytotoxic activity of CTL at concentration greater than 10 ng/ml since lysis of T2 cells incubated with G10-5 at more than 10 ng/ml was repeatedly lower than at 1-10 ng/ml in this assay condition in which the peptide was present in the medium during entire 4 h cytotoxicity assay (FIG. 8D). The relative binding affinity of these epitopes to HLA-A2.1 was also measured using an in vitro competitive binding assay (Table 13). $G9_{154}$ had an higher binding affinity (50% inhibition of the standard peptide at 11 nM) to the HLA-A2.1 molecule than $G10_{154}$ (1010 nM) which contains an extra leucine at the C-terminus of $G9_{154}$, and could sensitize T2 cells at lower concentrations than $G10_{154}$ (FIG. 8A). $G9_{209}$ also bound to HLA-A2.1 with higher affinity (84 nM) than $G10_{208}$ (2080 nM) which contains an extra threonine at the N-terminus, and could sensitize T2 cells at lower concentrations of peptide than $G10_{208}$ (FIG. 8B). Thus, the 9-mer peptides were superior to the corresponding 10 mer peptides in the sensitization of T2 cells to CTL lysis, and they also had higher binding affinities to HLA-A2.1. This was also the case for the identified MART-1 9 and 10 amino acid peptides (M9-2, M10-3, M10-4) (Example 2; Kawakami, Y., et al., (1994). *J. Exp. Med.* 180:347). The results of the peptide titration in the T2 cell lysis assay correlated with the results of the HLA-A2.1 binding affinity as measured by the in vitro binding assay. The other gp100 epitopes, $G9_{280}$, G10-4, or G10-5 had binding affinities for HLA-A2.1 with 50 inhibition at 95 nM, 483 nM, or 13 nM, respectively. The HLA-A2.1 binding affinities of the previously identified HLA-A2 restricted melanoma epitopes in MART-1 (Example 2; Kawakami, Y., et al., (1994) *J. Exp. Med.* 180:347) and tyrosinase (Wolfel, T., (1994) *Eur. J. Immunol.* 24:759) were also measured (M9-2(397 nM), M10-3(2272 nM), M10-4(5555 nM), $T9_{309}$(333 nM), $T9_{369}$ (40 nM)). Except for the 10mer peptides ($G10_{154}$, $G10_{208}$, GM10-3, GM10-4), for which overlapping 9-mer epitopes ($G9_{154}$, $G9_{209}$, M9-2) existed, all melanoma epitopes had either high ($G9_{154}$, G10-5, $T9_{369}$) or intermediate ($G9_{209}$, $G9_{280}$, G10-4, M9-2, $T9_1$) binding affinities to HLA-A2.1.

Discussion

Multiple epitopes in the gp100 human melanoma antigen recognized by 4 TIL which were associated with tumor regression when adoptively transferred to the autologous patients have been identified in this study. Among the 5 epitopes described in this study, $G9_{154}$ or $G10_{154}$ appeared to be the most commonly recognized, since these were recognized by 3 of 4 gp100 reactive TIL derived from different patients. Although the $G9_{280}$ peptide was reported to be recognized by all 5 CTL derived from PBL of different patients (Cox, A. L., et al., (1994)). *Science* 264:716), it was only recognized by 2 of 4 gp100 reactive TIL in this study. This difference may be due to the sources of T-cells (TIL vs PBL) used.

It will be appreciated that the MART-1 peptide M9-2 may also be designated $M9_{27}$, the MART-1 peptide M10-3 may also be designated $M10_{26}$, and the MART-1 peptide M10-4 may also be designated $M10_{27}$. It will also be appreciated that the gp100 peptide G10-4 may also be designated $G10_{457}$ and the gp100 peptide G10-5 may also be designated $G10_{476}$.

TABLE 11

Summary of antigen recognition by HLA-A2 restricted melanoma specific TIL

| | TIL | | | | | | | | | |
|---|---|---|---|---|---|---|---|---|---|---|
| | 1200 | 620 | 660 | 1143 | 1074 | 1088 | 1235 | 1318 | 1363 | 1399 |
| Clinical* Response | PR | PR | PR | PR | NR | NR | NR | NR | NR | NR |
| Antigen(epitope) | | | | | | | | | | |
| gp100 | + ($G9_{154}$) ($G10$-4) | + ($G9_{209}$) ($G9_{154}$) | + ($G9_{280}$) ($G9_{154}$) ($G10$-5) | + ($G9_{280}$) | − | − | − | − | − | − |
| MART-1 | − | + (M9-2) | + (M9-2) | + (M9-2) | + (M9-2) | + (M9-2) | + (M9-2) | + (M9-2) | + (M9-2) | + (M9-2) |
| tyrosinase | − | − | − | − | − | − | − | − | − | − |
| gp75 | − | − | − | − | − | − | − | − | − | − |

G9(10): gp100-9(10)-mer peptides, M9-2: MART-1$_{27-35}$ peptide Recognition of gp100 by TIL is significantly (p < 0.001) correlated with clinical response for adoptive immunotherapy with HLA-A2 restricted TIL.
*PR, partial response (>50% reduction in the sum of the product of perpendicular tumor diameters); NR, no response (<50% reduction)

TABLE 12

Recognition of gp100 peptides by TIL

| Target cells | Peptide | TIL (% specific lysis at E:T = 40:1) | | | | |
|---|---|---|---|---|---|---|
| Exp. 1 | | 620-1 | 620-2 | 660-1 | 1143 | 1200 | 1235 |
| 624mel | none | 32 | 36 | 47 | 20 | 77 | 11 |
| 397mel | none | 2 | 3 | 0 | 0 | 0 | 0 |
| T2 | none | 0 | 5 | 3 | 1 | 0 | 2 |
| T2 | M9-2 | 19 | 84 | 69 | 49 | 1 | 86 |
| T2 | $G9_{154}$ | 0 | 21 | 4 | 0 | 100 | 0 |
| T2 | $G10_{154}$ | 3 | 19 | 7 | 4 | 75 | 2 |
| T2 | $G9_{209}$ | 45 | 21 | 0 | 3 | 0 | 0 |
| T2 | $G10_{208}$ | 42 | 36 | 7 | 4 | 2 | 3 |
| T2 | $G9_{280}$ | 2 | 7 | 43 | 11 | 0 | 0 |
| T2 | G10-4 | 0 | 7 | 6 | 0 | 15 | 0 |
| T2 | G10-5 | 2 | 7 | 2 | 1 | 7 | 0 |
| Exp. 2 | | 620-1 | 620-2 | 660-2 | 1143 | 1200 | 1235 |
| 624mel | none | 60 | 65 | 74 | 49 | 82 | 18 |
| 397mel | none | 2 | 6 | 0 | 0 | 0 | 0 |
| T2 | none | 1 | 12 | 1 | 0 | 1 | 2 |
| T2 | M9-2 | 36 | 85 | 50 | 39 | 0 | 60 |
| T2 | $G9_{154}$ | 5 | 27 | 32 | 1 | 78 | 5 |
| T2 | $G10_{154}$ | 4 | 31 | 30 | 2 | 85 | 3 |
| T2 | $G9_{209}$ | 22 | 74 | 5 | 4 | 1 | 3 |
| T2 | $G10_{208}$ | 35 | 80 | 7 | 10 | 1 | 5 |
| T2 | $G9_{280}$* | 2 | 9 | 75 | 34 | 1 | 2 |
| Exp. 3 | | | | 660-3 | 1143 | 1200 | 1235 |
| 624mel | none | | | 52 | 15 | 66 | 40 |
| 397mel | none | | | 5 | 3 | 7 | 4 |
| T2 | none | | | 7 | 3 | 7 | 4 |
| T2 | M9-2 | | | 50 | 62 | 4 | 94 |
| T2 | $G9_{280}$ | | | 99 | 37 | 9 | 5 |
| T2 | G10-4 | | | 0 | 0 | 50 | 0 |
| T2 | G10-5 | | | 14 | 2 | 6 | 5 |

Lysis by TIL of T2 cells preincubated with MART1 epitope, M9-2 (AAGIGILTV) and gp100 epitopes, $G9_{154}$ (KTWGQYWQV), $G10_{154}$ (KTWGQYWQVL), $G9_{209}$ (ITDQVPFSV), $G10_{208}$ (TITDQVPFSV), $G9_{280}$ (YLEPGPVTA), G10-4(LLDGTATLRL), G10-5 (VLYRYGSFSV) at 1 ug/ml (* 1 ng/ml), was measured by 4 h-$^{51}$Cr release assays. TIL620-1, -2 or TIL660-1, -2, -3 were grown from the same TIL which was administered into the autologous patient, but were separately cultured. 624mel, HLA-A2+ gp100+, MART-1+ melanoma cell line, 397mel, HLA-A2− melanoma cell line. T2 cells, HLA-A2+ T cell-B-cell hybridoma.
Bold: statistically significant lysis

TABLE 13

The relative binding affinity of the human melanoma epitopes to HLA-A2.1

| Protein | Peptide | Sequence Standard.[b] | 50% inhibition (nM)[a] | Ratio to |
|---|---|---|---|---|
| gp100 | $G9_{154}$ | KTWGQYWQV SEQ ID NO: 46 | 11 | 0.45 |
| | $G10_{154}$ | KTWGQYWQVL SEQ ID NO: 47 | 1010 | 0.005 |
| | $G9_{209}$ | ITDQVPFSV SEQ ID NO: 48 | 84 | 0.06 |
| | $G10_{208}$ | TITDQVPFSV SEQ ID NO: 49 | 2080 | 0.0024 |
| | $G9_{280}$ | YLEPGPVTA SEQ ID NO: 40 | 95 | 0.053 |
| | G10-4 | LLDGTATLRL SEQ ID NO: 33 | 483 | 0.01 |
| | G10-5 | VLYRYGSFSV SEQ ID NO: 34 | 13 | 0.38 |
| MART-1 | M9-2 | AAGIGILTV SEQ ID NO: 4 | 395 | 0.013 |
| | M10-3 | EAAGIGILTV SEQ ID NO: 17 | 2272 | 0.0022 |
| | M10-4 | AAGIGILTVI SEQ ID NO: 18 | 5555 | 0.0009 |
| Tyrosinase | $T9_1$ | MLLAVLYCL SEQ ID NO: 31 | 333 | 0.015 |
| | $T9_{369}$ | YMNGTMSQV SEQ ID NO: 32 | 40 | 0.13 |

[a] Concentration of sample peptide required for 50% inhibition of the standard radiolabeled peptide HBC18-27.
[b] Ratio of the binding affinity of the sample peptide to that of the standard peptide (50% inhibition at 5 nM). Peptides are defined as high (50% inhibition at <50 nM, ratio >0.1), intermediate (50-500 nM, ratio 0.1-0.01) and weak (>500 nM, ratio <0.01) binding peptides.

EXAMPLE 5

Modification of melanoma Epitopes for Improvement of Immunogenicity

Material and Methods

Peptide synthesis and HLA-A2.1 binding assay. Peptides were synthesized by a solid phase method using a multiple peptide synthesizer and purified by HPLC, as previously described (Rivoltini, L et al. (1995) *Journal of Immunology*

Volume 154:2257-2265). The relative binding of peptides to HLA-A2.1, based on the inhibition of binding of a radiolabeled standard peptide to detergent-solubilized MHC molecules, was performed as previously described (Rivoltini, L et al. (1995) *Journal of Immunology* Volume 154:2257-2265). Briefly, various doses of the test peptides (ranging from 100 µM to 1 nM) were coincubated together with the 5 nM radiolabeled Hbc 18-27 (FLPSDYFPSV) peptide and HLA-A2.1 heavy chain and β2-microglobulin for 2 days at room temperature in the presence of protease inhibitors. The percentage of MHC-bound radioactivity was determined by gel filtration and the 50% inhibitory dose was calculated for each peptide.

Induction of peptide specific CTL PBMC were separated from peripheral blood of HLA-A2+ melanoma patients and normal donors by centrifugation on Ficoll-Hypaque gradients and used as fresh or cryopreserved samples. Peptide specific CTL lines were generated as follows: at day 0, PBMC were plated at a concentration of $1.5 \times 10^6$/ml in 24-well plates (2 ml/well) in Iscove's medium containing 10% human AB serum, L-glutamine, antibiotics (CM) and in the presence of 1 ug/ml peptide. Two days later, 12 IU/ml interleukin 2 (IL-2) (Chiron Co., Emeryville, Calif.) were added to the cultures. Lymphocytes were then restimulated weekly as follows: responder cells were harvested, washed once and replated in 24-well plates at a concentration of $2.5 \times 10^5$ cells/ml in CM. Autologous PBMC were thawed, washed twice in PBS, resuspended at $5-8 \times 10^6$ cells/ml in CM and pulsed with 1 ug/ml peptide in 15-ml conical tubes (5 ml/tube) for 3 hours at 37° C. These PBMC (stimulators) were then irradiated at 3000 rads, washed once in PBS and added to the responder cells at responder:stimulator ratios ranging between 1:3 and 1:10. The next day, 12 IU/ml IL-2 were added to the cultures. The activity of these CTL was tested by cytotoxicity assays after at least 2 rounds (14 days) of peptide stimulation. To generate CTL from TIL cultures, the dissociated tumor suspension were cultured for 1-2 days in 10% FCS RPMI-1640 medium to allow tumor cell adherence. The lymphocytes, recovered from the non-adherent fraction, were used for the induction of peptide specific CTL as described above.

Assessment of antigen recognition by CTL. $^{51}$Cr release cytotoxic assays were performed to detect the recognition of peptide and melanoma cells by CTL. To analyze peptide recognition, T2 cell lines were preincubated for 2 h at 37° C. with 1 ug/ml peptide, washed and used as target cells in a $^{51}$Cr release cytotoxic assay. The melanoma lines 624mel was established in our laboratory (See Example 1).

In order to make more immunogenic peptides for induction of anti-melanoma T-cells than natural melanoma epitopes, a variety of peptides in which at least 1 amino acid was changed based on consensus motifs in peptides binding to a specific MHC Class I allele Falk, et al. (1991) *Nature* 351:290; Kubo et al. (1994) *J. Immunol* 152:3913; Parker, K. et al. (1992) *Journal of Immunology* 149:3580; Ruppert, J. et al. (1993) *Cell* 74:929-937) (Tables 14, 15, 16, and 17). Although most of the previously isolated viral epitopes and the naturally processed HLA-A2.1 binding peptides contained leucine or methionine at the 2nd major anchor position and valine at the last major anchor position (dominant anchor amino acids) and had high binding affinity to HLA-A2.1, the isolated MART-1 or gp100 melanoma epitopes contain non-dominant amino acid at major anchor position such as alanine (the 2nd position of M9-2, the 9th position of G9-280) and threonine (the 2nd position of G9-154 and G9-209). The M9-2, G9-209 and G9-280 are not high affinity binders. By changing amino acid at the 1st, 2nd, 3rd or 9th positions which are important for HLA-A2 binding to the peptide, but less important for recognition by T-cell receptors, artificial peptides which can bind to HLA-A2.1 with higher affinity and still be recognized by natural epitope specific T-cells may be generated.

Among modified M9-2, G9-280, G9-209, G9-154 peptides, M9-2-2L, M9-2-1F, M9-2-3Y, G9-280-9V, G9-280-9L, G9-280-9I, G9-280-1F, G9-209-2L, G9-209-2M, G9-209-2I, G9-209-1F, G9-209-1Y, G9-209-1W2L, G9-209-1F2L, G9-209-1Y2L have higher binding affinity and were recognized by the original melanoma reactive T-cells. (Tables 14, 15, 16 and 17) PBL stimulated with autologous PBMC pulsed with G9-154-2I, G9-209-1F2L, or G9-280-9V (Tables 18, 19 and 20) recognized and lysed not only the original epitopes but also melanoma tumor cells (624mel) better than PBL stimulated with natural epitopes (G9-154, G9-209, G9-280).

These results demonstrated that modified peptides could be used for induction of anti-tumor T-cells instead of natural epitopes. Other peptides which were not recognized by the particular T-cells used in our study, but have higher binding affinity to HLA-A2.1 may induce a different set of T-cells capable of recognizing the original melanoma epitopes in in vitro or in vivo. These modified peptides may be used for induction of anti-melanoma T-cells in vitro and immunization of patients for the treatment of patients with melanoma or for the prevention of melanoma.

TABLE 14

Modified MART-1 M9-2 peptides

| Peptide | Sequence | Binding affinity to HLA-A2.1 (nM) | Recognition by M9-2 reactive T-cell |
|---|---|---|---|
| M9-2 parent | AAGIGILTV SEQ ID NO: 4 | 1064 | + |
| M9-2-2L | ALGIGILTV SEQ ID NO: 50 | 10 | + |
| M9-2-2M | AMGIGILTV SEQ ID NO: 51 | 14 | − |
| M9-2-2I | AIGIGILTV SEQ ID NO: 52 | 77 | − |
| M9-2-1W | WAGIGILTV SEQ ID NO: 53 | 1351 | + |
| M9-2-1F | FAGIGILTV SEQ ID NO: 54 | 244 | + |
| M9-2-1Y | YAGIGILTV SEQ ID NO: 55 | 136 | − |
| M9-2-3W | AAWIGILTV SEQ ID NO: 56 | 65 | − |
| M9-2-3F | AAFIGILTV SEQ ID NO: 57 | 67 | − |
| M9-2-3Y | AAYIGILTV SEQ ID NO: 58 | 102 | + |
| M9-2-1K2L | KLGIGILTV SEQ ID NO: 59 | 14 | − |
| M9-2-1K2M | KMGIGILTV SEQ ID NO: 60 | 27 | − |
| M9-2-1K2I | KIGIGILTV SEQ ID NO: 61 | 94 | − |
| M9-2-1W2L | WLGIGILTV SEQ ID NO: 62 | 11 | − |

TABLE 14-continued

Modified MART-1 M9-2 peptides

| Peptide | Sequence | Binding affinity to HLA-A2.1 (nM) | Recognition by M9-2 reactive T-cell |
|---|---|---|---|
| M9-2-1F2L SEQ ID NO: 63 | FLGIGILTV | 1.8 | − |
| M9-2-1Y2L SEQ ID NO: 64 | YLGIGILTV | 3.2 | − |
| M9-2-2L3W SEQ ID NO: 65 | ALWIGILTV | 5.5 | − |
| M9-2-2L3F SEQ ID NO: 66 | ALFIGILTV | 1.4 | − |
| M9-2-2L3Y SEQ ID NO: 67 | ALYIGILTV | 3.7 | − |

TABLE 15

Modified gp100 G9-154 peptides

| Peptide | Sequence | Binding affinity to HLA-A2.1 (nM) | Recognition by G9-154 reactive T-cell |
|---|---|---|---|
| G9-154 parent SEQ ID NO: 46 | KTWGQYWQV | 5.7 | + |
| G9-154-2L SEQ ID NO: 68 | KLWGQYWQV | 2 | + |
| G9-154-2M SEQ ID NO: 69 | KMWGQYWQV | 6.5 | + |
| G9-154-2I SEQ ID NO: 70 | KIWGQYWQV | 3 | + |
| 09-154-1W SEQ ID NO: 71 | WTWGQYWQV | 60 | − |
| 09-154-1F SEQ ID NO: 72 | FTWGQYWQV | 1.6 | − |
| G9-154-1Y SEQ ID NO: 73 | YTWGQYWQV | 2.5 | − |
| 09-154-1A SEQ ID NO: 74 | ATWGQYWQV | 5.2 | + |
| G9-154-1L SEQ ID NO: 75 | LTWGQYWQV | 3.4 | + |
| G9-154-3Y SEQ ID NO: 76 | KTYGQYWQV | 30 | + |
| 09-154-3F SEQ ID NO: 77 | KTFGQYWQV | 21 | + |
| G9-154-1A2L SEQ ID NO: 78 | ALWGQYWQV | 2.3 | + |
| G9-154-1L2L SEQ ID NO: 79 | LLWGQYWQV | 1.6 | + |
| G9-154-1W2L SEQ ID NO: 80 | WLWGQYWQV | 2.8 | − |
| 09-154-1F2L SEQ ID NO: 81 | FLWGQYWQV | 2.6 | − |

TABLE 15-continued

Modified gp100 G9-154 peptides

| Peptide | Sequence | Binding affinity to HLA-A2.1 (nM) | Recognition by G9-154 reactive T-cell |
|---|---|---|---|
| G9-154-1Y2L SEQ ID NO: 82 | YLWGQYWQV | 1.7 | − |

TABLE 16

Modified gp100 G9-209 peptides

| Peptide | Sequence | Binding affinity to HLA-A2.1 (nM)* | Recognition by G9-209 reactive T-cell |
|---|---|---|---|
| G9-209 parent SEQ ID NO: 48 | ITDQVPFSV | 172 | + |
| G9-209-2L SEQ ID NO: 83 | ILDQVPFSV | 3.3 | + |
| G9-209-2M SEQ ID NO: 84 | IMDQVPFSV | 19 | + |
| G9-209-2I SEQ ID NO: 85 | IIDQVPFSV | 40 | + |
| G9-209-1F SEQ ID NO: 86 | FTDQVPFSV | 61 | + |
| G9-209-1W SEQ ID NO: 87 | WTDQVPFSV | 711 | + |
| G9-209-1Y SEQ ID NO: 88 | YTDQVPFSV | 85 | + |
| G9-209-3W SEQ ID NO: 89 | ITWQVPFSV | 34 | − |
| G9-209-3F SEQ ID NO: 90 | ITFQVPFSV | 66 | − |
| G9-209-3Y SEQ ID NO: 91 | ITYQVPFSV | 33 | − |
| G9-209-3A SEQ ID NO: 92 | ITAQVPFSV | 95 | − |
| G9-209-3M SEQ ID NO: 93 | ITMQVPFSV | 40 | − |
| G9-209-3S SEQ ID NO: 94 | ITSQVPFSV | 649 | − |
| G9-209-2L3W SEQ ID NO: 95 | ILWQVPFSV | 1.7 | − |
| G9-209-2L3F SEQ ID NO: 96 | ILFQVPFSV | 2 | − |
| G9-209-2L3Y SEQ ID NO: 97 | ILYQVPFSV | 5 | − |
| G9-209-2L3A SEQ ID NO: 98 | ILAQVPFSV | 11 | − |
| G9-209-2L3M SEQ ID NO: 99 | ILMQVPFSV | 7.6 | − |
| G9-209-2L3S SEQ ID NO: 100 | ILSQVPFSV | 20 | − |

TABLE 16-continued

Modified gp100 G9-209 peptides

| Peptide | Sequence | Binding affinity to HLA-A2.1 (nM)* | Recognition by G9-209 reactive T-cell |
|---|---|---|---|
| G9-209-1W2L | WLDQVPFSV SEQ ID NO: 101 | 12 | + |
| G9-209-1F2L | FLDQVPFSV SEQ ID NO: 102 | 2.2 | + |
| G9-209-1Y2L | YLDQVPFSV SEQ ID NO: 103 | 2.3 | + |

*a Concentration of sample peptide required for 50% inhibition of the standard radiolabeled peptide HBC18-27. Peptides are defined as high (50% inhibition at <50 nM), intermediate (50-500 nM) and weak (>500 nM) binding peptides. (see ref gp100 epitope)

TABLE 17

Modified gp100 G9-280 peptides

| Peptide | Sequence | Binding affinity to HLA-A2.1 (nM) | Recognition by G9-280 reactive T-cell |
|---|---|---|---|
| G9-280 parent | YLEPGPVTA SEQ ID NO: 40 | 455 | + |
| G9-280-9V | YLEPGPVTV SEQ ID NO: 104 | 48 | + |
| G9-280-9L | YLEPGPVTL SEQ ID NO: 105 | 88 | + |
| G9-280-9I | YLEPGPVTI SEQ ID NO: 106 | 65 | + |
| G9-280-1F | FLEPGPVTA SEQ ID NO: 107 | 125 | + |
| G9-280-1W | WLEPGPVTA SEQ ID NO: 108 | 833 | + |
| G9-280-3Y | YLYPGPVTA SEQ ID NO: 109 | 17 | − |
| G9-280-3W | YLWPGPVTA SEQ ID NO: 110 | 3.2 | − |
| G9-280-3F | YLFPGPVTA SEQ ID NO: 111 | 3.2 | − |
| G9-280-3M | YLMPGPVTA SEQ ID NO: 112 | 4.3 | − |
| G9-280-3S | YLSPGPVTA SEQ ID NO: 113 | 42 | − |
| G9-280-3A | YLAPGPVTA SEQ ID NO: 114 | 9.3 | − |
| G9-280-3M9V | YLMPGPVTV SEQ ID NO: 115 | 12 | − |
| G9-280-3S9V | YLSPGPVTV SEQ ID NO: 116 | 23 | − |
| G9-280-3A9V | YLAPGPVTV SEQ ID NO: 117 | 15 | − |
| G9-280-3Y9V | YLYPGPVTV SEQ ID NO: 118 | 8.9 | − |

TABLE 17-continued

Modified gp100 G9-280 peptides

| Peptide | Sequence | Binding affinity to HLA-A2.1 (nM) | Recognition by G9-280 reactive T-cell |
|---|---|---|---|
| G9-280-3F9V | YLFPGPVTV SEQ ID NO: 119 | 5.8 | − |
| G9-280-3W9V | YLWPGPVTV SEQ ID NO: 120 | 7.4 | − |

TABLE 18

Induction of anti-melanoma CTL using modified G9-154 peptide

| | Effector T-cells | |
|---|---|---|
| Target | PBL stimulated with G9-154 | PBL stimulated with G9-154-2I |
| | % specific lysis (E:T = 3D40:1) | |
| T2 | 11 | 1 |
| T2+G9-154 | 14 | 37 |
| T2+G9-154-2I | 8 | 38 |
| 624mel | 5 | 23 |

[51]Cr release assay was performed after 4 times stimulation with autologous PBMC preincubated with peptides.

TABLE 19

Induction of anti-melanoma CTL using modified G9-209 peptide

| | Effector T-cells | |
|---|---|---|
| Target | PBL stimulated with G9-209 | PBL stimulated with G9-209-1F2L |
| | % specific lysis (E:T = 3D40:1) | |
| T2 | 0 | 0 |
| T2+G9-209 | 6 | 85 |
| T2+G9-209-1F2L | 1 | 86 |
| 624mel | 4 | 63 |

[51]Cr release assay was performed after 4 times stimulation with autologous PBMC preincubated with peptides.

TABLE 20

Induction of anti-melanoma CTL using modified G9-280 peptide

| | Effectoe T-cells | |
|---|---|---|
| Target | PBL stimulated with G9-280 | PBL stimulated with G9-280-9V |
| | % specific lysis (E:T = 3D40:1) | |
| T2 | 3 | 0 |
| T2+G9-280 | 11 | 87 |
| T2+G9-280-9V | 8 | 58 |
| 624mel | 11 | 71 |

[51]Cr release assay was performed after 4 times stimulation with autologous PBMC preincubated with peptides.

EXAMPLE 6

MART-1 vaccines as a Treatment for Melanoma in Mammals

MART-1 vaccines may be efficacious in treating mammals afflicted with melanoma. For example, MART-1 vaccines may be administered to individuals. Mammals can be immunized with the MART-1 proteins, peptides or modified peptides described herein in ranges of about 1 mg-to to about 100 mg. Alternatively mammals, preferably humans may be immunized with the MART-1 nucleic acid sequence inserted into a viral vector such as vaccinia virus, adenovirus or fowl pox virus. A range of about $10^6$ to about $10^{11}$ viral particles carrying the MART-1 nucleic acid sequences corresponding to immunogenic MART-1 peptides or modified peptides or analogs thereof, may be administered per mammal, preferably a human. The mammals will be monitored for antibodies to the immunogen or increase in cytotoxic lymphocytes (CTL) recognizing the immunogen by conventional methods or alleviation of clinical signs and symptoms of the active disease. Specific parameters to be assessed include production of immune cells that recognize the vaccine antigen or tumor regression. Such vaccines may be administered either prophylactically or therapeutically. Mammals may also be immunized with the gp-100 nucleic acid sequence inserted into a retroviral vector or GP-100 immunogenic peptides or modified peptides or analogs thereof. Suggested dose ranges of the antigen in retroviruses that may be used are about $10^6$ to about $10^{11}$ viral particles per mammal, preferably a human. Response and efficacy of the retroviral vaccines will be assessed as described above.

EXAMPLE 7

Use of Lymphocytes Sensitized to Immunogenic Peptides Derived from Melanoma Antigens for Therapeutically Treating Mammals Afflicted with Melanoma T-lymphocytes presensitized to the melanoma antigen may be effective in therapeutically treating mammals afflicted with melanoma. The T-lymphocytes will be isolated from peripheral blood lymphocytes or tumor infiltrating lymphocytes and exposed in vitro to the MART-1 protein or peptide. T-lymphocytes are isolated from peripheral blood or melanoma tumor suspensions and cultured in vitro (Kawakami, Y. et al. (1988) *J. Exp. Med.* 168: 2183-2191). The T-lymphocytes are exposed to the MART-1 peptide AAGIGILTV for a period of about to 1-16 hours at a concentration of about 1 to about 10 mg/ml. T-lymphocytes exposed to the antigen will be administered to the mammal, preferably a human at about $10^9$ to about $10^{12}$ lymphocytes per mammal. Alternatively, the T-lymphocytes may be exposed to the modified MART-1 peptides. The lymphocytes may be administered either intravenously, intraperitoneally or intralesionally. This treatment may be administered concurrently with other therapeutic treatments such as cytokines, radiotherapy, surgical excision of melanoma lesions and chemotherapeutic drugs, adoptive T lymphocyte therapy. Alternatively, the T-lymphocytes may be exposed to the gp100 immunogenic peptides or modified immunogenic peptides described herein.

The present invention is not to be limited in scope by the nucleic acid sequences deposited, since the deposited embodiments is intended as a single illustration of one aspect of the invention and any sequences which are functionally equivalent are within the scope of this invention. Indeed, various modifications of the invention in addition to those shown and described herein will become apparent to those skilled in the art from the foregoing description and accompanying drawings. Such modifications are intended to fall within the scope of the dependent claims.

The invention claimed is:

1. A vector comprising a nucleic acid encoding an immunogenic peptide consisting of 5-20 contiguous amino acids of gp100 (SEQ ID NO: 27) with at least one amino acid modification in the 5-20 contiguous amino acids of SEQ ID NO: 27, wherein the immunogenic peptide reacts with T-lymphocytes and said modification is an amino acid substitution located at an amino acid position of the immunogenic peptide selected from the group consisting of: (i) the first position, (ii) the second position, (iii) the third position, (iv) the ninth position, (v) tenth position, and (vi) combinations of at least two of (i)-(v), wherein the immunogenic peptide is not YIEPGPVTA (SEQ ID NO: 134).

2. The vector of claim 1, wherein the immunogenic peptide is selected from the group consisting of ITDQVPFSV (SEQ ID NO: 48) with at least one amino acid modification in SEQ ID NO: 48, TITDQVPFSV (SEQ ID NO: 49) with at least one amino acid modification in SEQ ID NO: 49, LLDGTATLRL (SEQ ID NO: 33) with at least one amino acid modification in SEQ ID NO: 33, VLYRYGSFSV (SEQ ID NO: 34) with at least one amino acid modification in SEQ ID NO: 34, VLKRCLLHL (SEQ ID NO: 36) with at least one amino acid modification in SEQ ID NO: 36, ALDGGNKHFL (SEQ ID NO: 35) with at least one amino acid modification in SEQ ID NO: 35, VLPSPACQLV (SEQ ID NO: 37) with at least one amino acid modification in SEQ ID NO: 37, YLEPGPVTA (SEQ ID NO: 40) with at least one amino acid modification in SEQ ID NO: 40, SLADTNSLAV (SEQ ID NO: 38) with at least one amino acid modification in SEQ ID NO: 38, SVSVSQLRA (SEQ ID NO: 39) with at least one amino acid modification in SEQ ID NO: 39, and LNVSLADTN (SEQ ID NO: 41) with at least one amino acid modification in SEQ ID NO: 41.

3. A vector comprising an isolated nucleic acid encoding an immunogenic peptide comprising an amino acid sequence of the formula selected from the group consisting of $X_1X_2X_3GQYWQX_4$ (SEQ ID NO: 123), $X_1X_2X_3QVPFSX_4$ (SEQ ID NO: 124) and $X_1X_2X_3PGPVTX_4$ (SEQ ID NO: 125), wherein:

$X_1$ is selected from the group consisting of methionine, leucine, alanine, glycine, threonine, isoleucine, valine, tyrosine, serine, tryptophan, phenylalanine, lysine and aspartic acid;

$X_2$ is any hydrophobic aliphatic amino acid when the immunogenic peptide comprises an amino acid sequence of the formula $X_1X_2X_3GQYWQX_4$ (SEQ ID NO: 123) or $X_1X_2X_3QVPFSX_4$ (SEQ ID NO: 124);

$X_2$ is selected from the group consisting of methionine, leucine, alanine, glycine, valine and threonine when the immunogenic peptide comprises an amino acid sequence of the formula $X_1X_2X_3PGPVTX_4$ (SEQ ID NO: 125);

$X_3$ is any naturally occurring amino acid; and $X_4$ is any hydrophobic aliphatic amino acid, wherein the immunogenic peptide is not KTWGQYWQV (SEQ ID NO: 46), KTWGQYWQVL (SEQ ID NO: 47), ITDQVPFSV (SEQ ID NO: 48), or YLEPGPVTA (SEQ ID NO: 40).

4. The vector of claim 3, wherein $X_2$ is selected from the group consisting of methionine, leucine, alanine, glycine, isoleucine, valine and threonine when the immunogenic peptide comprises an amino acid sequence of the formula $X_1X_2X_3GQYWQX_4$ (SEQ ID NO: 123) or $X_1X_2X_3QVPFSX_4$ (SEQ ID NO: 124).

5. The vector of claim 3, wherein $X_3$ is selected from the group consisting of methionine, leucine, alanine, glycine, threonine, isoleucine, tyrosine, valine, tryptophan, phenylalanine, serine, lysine and aspartic acid.

6. The vector of claim 3, wherein $X_4$ is selected from the group consisting of methionine, leucine, alanine, glycine, isoleucine, valine and threonine.

7. The vector of claim 3, wherein the immunogenic peptide is selected from the group consisting of KLWGQYWQV (SEQ ID NO: 68), KMQGQYWQV (SEQ ID NO: 69), KIWGQYWQV (SEQ ID NO: 70), WTWGQYWQV (SEQ ID NO: 71), FTWGQYWQV (SEQ ID NO: 72), YTWGQYWQV (SEQ ID NO: 73), ATWGQYWQV (SEQ ID NO: 74), LTWGQYWQV (SEQ ID NO: 75), KTYGQYWQV (SEQ ID NO: 76), KTFGQYWQV (SEQ ID NO: 77), ALWGQYWQV (SEQ ID NO: 78), LLWGQYWQV (SEQ ID NO: 79), WLWGQYWQV (SEQ ID NO: 80), FLWGQYWQV (SEQ ID NO: 81), and YLWGQYWQV (SEQ ID NO: 82).

8. The vector of claim 3, wherein the immunogenic peptide is selected from the group consisting of ILDQVPFSV (SEQ ID NO: 83), IMDQVPFSV (SEQ ID NO: 84), IIDQVPFSV (SEQ ID NO: 85), FTDQVPFSV (SEQ ID NO: 86), WTDQVPFSV (SEQ ID NO: 87), YTDQVPFSV (SEQ ID NO: 88), ITWQVPFSV (SEQ ID NO: 89), ITFQVPFSV (SEQ ID NO: 90), ITYQVPFSV (SEQ ID NO: 91), ITAQVPFSV (SEQ ID NO: 92), ITMQVPFSV (SEQ ID NO: 93), ITSQVPFSV (SEQ ID NO: 94), ILWQVPFSV (SEQ ID NO: 95), ILFQVPFSV (SEQ ID NO: 96), ILYQVPFSV (SEQ ID NO: 97), ILAQVPFSV (SEQ ID NO: 98), ILMQVPFSV (SEQ ID NO: 99), ILSQVPFSV (SEQ ID NO: 100), WLDQVPFSV (SEQ ID NO: 101), FLDQVPFSV (SEQ ID NO: 102), and YLDQVPFSV (SEQ ID NO: 103).

9. The vector of claim 3, wherein the immunogenic peptide is selected from the group consisting of YLEPGPVTV (SEQ ID NO:104), YLEPGPVTL (SEQ ID NO:105), YLEPGPVTI (SEQ ID NO:106), FLEPGPVTA (SEQ ID NO:107), WLEPGPVTA (SEQ ID NO:108), YLYPGPVTA (SEQ ID NO:109), YLWPGPVTA (SEQ ID NO:110), YLFPGPVTA (SEQ ID NO:111), YLMPGPVTA (SEQ ID NO:112), YLSPGPVTA (SEQ ID NO:113), YLAPGPVTA (SEQ ID NO:114), YLMPGPVTV (SEQ ID NO:115), YLSPGPVTV (SEQ ID NO:116), YLAPGPVTV (SEQ ID NO:117), YLYPGPVTV (SEQ ID NO:118), YLFPGPVTV (SEQ ID NO:119), and YLWPGPVTV (SEQ ID NO:120).

10. A host cell comprising the vector of claim 1.

11. A host cell comprising the vector of claim 3.

* * * * *

SEQUENCE LISTING

<160> NUMBER OF SEQ ID NOS: 134

<210> SEQ ID NO 1
<211> LENGTH: 1559
<212> TYPE: DNA
<213> ORGANISM: Homo sapiens

<400> SEQUENCE: 1

```
agcagacaga ggactctcat taaggaaggt gtcctgtgcc ctgaccctac aagatgccaa      60
gagaagatgc tcacttcatc tatggttacc ccaagaaggg gcacggccac tcttacacca     120
cggctgaaga ggccgctggg atcggcatcc tgacagtgat cctgggagtc ttactgctca     180
tcggctgttg gtattgtaga agacgaaatg gatacagagc cttgatggat aaaagtcttc     240
atgttggcac tcaatgtgcc ttaacaagaa gatgcccaca agaagggttt gatcatcggg     300
acagcaaagt gtctcttcaa gagaaaaact gtgaacctgt ggttcccaat gctccacctg     360
cttatgagaa actctctgca gaacagtcac caccacctta ttcaccttaa gagccagcga     420
gacacctgag acatgctgaa attatttctc tcacactttt gcttgaattt aatacagaca     480
tctaatgttc tcctttggaa tggtgtagga aaaatgcaag ccatctctaa taataagtca     540
```

-continued

```
gtgttaaaat tttagtaggt ccgctagcag tactaatcat gtgaggaaat gatgagaaat      600
attaaattgg gaaaactcca tcaataaatg ttgcaatgca tgatactatc tgtgccagag      660
gtaatgttag taaatccatg gtgttatttt ctgagagaca gaattcaagt gggtattctg      720
gggccatcca atttctcttt acttgaaatt tggctaataa caaactagtc aggttttcga      780
accttgaccg acatgaactg tacacagaat tgttccagta ctatggagtg ctcacaaagg      840
atacttttac aggttaagac aaagggttga ctggcctatt tatctgatca agaacatgtc      900
agcaatgtct ctttgtgctc taaaattcta ttatactaca ataatatatt gtaaagatcc      960
tatagctctt ttttttgag atggagtttc gcttttgttg cccaggctgg agtgcaatgg     1020
cgcgatcttg gctcaccata acctccgcct cccaggttca agcaattctc ctgccttagc     1080
ctcctgagta gctgggatta caggcgtgcg ccactatgcc tgactaattt tgtagtttta     1140
gtagagacgg ggtttctcca tgttggtcag gctggtctca aactcctgac ctcaggtgat     1200
ctgcccgcct cagcctccca aagtgctgga attacaggcg tgagccacca cgcctggctg     1260
gatcctatat cttaggtaag acatataacg cagtctaatt acatttcact tcaaggctca     1320
atgctattct aactaatgac aagtattttc tactaaacca gaaattggta gaaggattta     1380
aataagtaaa agctactatg tactgcctta gtgctgatgc ctgtgtactg ccttaaatgt     1440
acctatggca atttagctct cttgggttcc caaatccctc tcacaagaat gtgcagaaga     1500
aatcataaag gatcagagat tctgaaaaaa aaaaaaaaa aaaaaaaaa aaaaaaaa         1559
```

```
<210> SEQ ID NO 2
<211> LENGTH: 118
<212> TYPE: PRT
<213> ORGANISM: Homo sapiens

<400> SEQUENCE: 2

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Thr Thr Ala Glu Glu Ala Ala Gly Ile
1               5
```

```
<210> SEQ ID NO 4
<211> LENGTH: 9
<212> TYPE: PRT
<213> ORGANISM: Artificial
<220> FEATURE:
<223> OTHER INFORMATION: Synthetic

<400> SEQUENCE: 4

Ala Ala Gly Ile Gly Ile Leu Thr Val
1               5

<210> SEQ ID NO 5
<211> LENGTH: 9
<212> TYPE: PRT
<213> ORGANISM: Artificial
<220> FEATURE:
<223> OTHER INFORMATION: Synthetic

<400> SEQUENCE: 5

Gly Ile Gly Ile Leu Thr Val Ile Leu
1               5

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Gly Ile Leu Thr Val Ile Leu Gly Val
1               5

<210> SEQ ID NO 7
<211> LENGTH: 9
<212> TYPE: PRT
<213> ORGANISM: Artificial
<220> FEATURE:
<223> OTHER INFORMATION: Synthetic

<400> SEQUENCE: 7

Ile Leu Thr Val Ile Leu Gly Val Leu
1               5

<210> SEQ ID NO 8
<211> LENGTH: 9
<212> TYPE: PRT
<213> ORGANISM: Artificial
<220> FEATURE:
<223> OTHER INFORMATION: Synthetic

<400> SEQUENCE: 8

Leu Thr Val Ile Leu Gly Val Leu Leu
1               5

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9

Thr Val Ile Leu Gly Val Leu Leu Leu
1               5
```

```
<210> SEQ ID NO 10
<211> LENGTH: 9
<212> TYPE: PRT
<213> ORGANISM: Artificial
<220> FEATURE:
<223> OTHER INFORMATION: Synthetic

<400> SEQUENCE: 10

Val Ile Leu Gly Val Leu Leu Leu Ile
1               5

<210> SEQ ID NO 11
<211> LENGTH: 9
<212> TYPE: PRT
<213> ORGANISM: Artificial
<220> FEATURE:
<223> OTHER INFORMATION: Synthetic

<400> SEQUENCE: 11

Ala Leu Met Asp Lys Ser Leu His Val
1               5

<210> SEQ ID NO 12
<211> LENGTH: 9
<212> TYPE: PRT
<213> ORGANISM: Artificial
<220> FEATURE:
<223> OTHER INFORMATION: Synthetic

<400> SEQUENCE: 12

Ser Leu His Val Gly Thr Gln Cys Ala
1               5

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

Pro Val Val Pro Asn Ala Pro Pro Ala
1               5

<210> SEQ ID NO 14
<211> LENGTH: 9
<212> TYPE: PRT
<213> ORGANISM: Artificial
<220> FEATURE:
<223> OTHER INFORMATION: Synthetic

<400> SEQUENCE: 14

Asn Ala Pro Pro Ala Tyr Glu Lys Leu
1               5

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

Tyr Thr Thr Ala Glu Glu Ala Ala Gly Ile
1               5                   10
```

```
<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Thr Ala Glu Glu Ala Ala Gly Ile Gly Ile
1               5                   10

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

Glu Ala Ala Gly Ile Gly Ile Leu Thr Val
1               5                   10

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Ala Ala Gly Ile Gly Ile Leu Thr Val Ile
1               5                   10

<210> SEQ ID NO 19
<211> LENGTH: 10
<212> TYPE: PRT
<213> ORGANISM: Artificial
<220> FEATURE:
<223> OTHER INFORMATION: Synthetic

<400> SEQUENCE: 19

Gly Ile Leu Thr Val Ile Leu Gly Val Leu
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Ile Leu Thr Val Ile Leu Gly Val Leu Leu
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic

<400> SEQUENCE: 21

Leu Thr Val Ile Leu Gly Val Leu Leu Leu
1               5                   10

<210> SEQ ID NO 22
```

-continued

```
<211> LENGTH: 10
<212> TYPE: PRT
<213> ORGANISM: Artificial
<220> FEATURE:
<223> OTHER INFORMATION: Synthetic

<400> SEQUENCE: 22

Thr Val Ile Leu Gly Val Leu Leu Leu Ile
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic

<400> SEQUENCE: 23

Arg Ala Leu Met Asp Lys Ser Leu His Val
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic

<400> SEQUENCE: 24

Ser Leu His Val Gly Thr Gln Cys Ala Leu
1               5                   10

<210> SEQ ID NO 25
<211> LENGTH: 10
<212> TYPE: PRT
<213> ORGANISM: Artificial
<220> FEATURE:
<223> OTHER INFORMATION: Synthetic

<400> SEQUENCE: 25

Ser Leu Gln Glu Lys Asn Cys Glu Pro Val
1               5                   10

<210> SEQ ID NO 26
<211> LENGTH: 2172
<212> TYPE: DNA
<213> ORGANISM: Homo sapiens

<400> SEQUENCE: 26
gtcgacggcc attaccaatc gcgaccggga agaacacaat ggatctggtg ctaaaaagat      60
gccttcttca tttggctgtg ataggtgctt tgctggctgt gggggctaca aaagtaccca     120
gaaaccagga ctggcttggt gtctcaaggc aactcagaac caaagcctgg aacaggcagc     180
tgtatccaga gtggacagaa gcccagagac ttgactgctg agaggtggt caagtgtccc      240 tcaaggtcag taatgatggg cctacactga ttggtgcaaa tgcctccttc tctattgcct     300
tgaacttccc tggaagccaa aaggtattgc cagatgggca ggttatctgg gtcaacaata     360
ccatcatcaa tgggagccag gtgtggggag acagccagt gtatccccag gaaactgacg      420
atgcctgcat cttccctgat ggtggaccctt gccatctgg ctcttggtct cagaagagaa     480
gctttgttta tgtctggaag acctggggcc aatactggca atttctaggg gcccagtgt     540 ctgggctgag cattgggaca ggcagggcaa tgctgggcac acacaccatg gaagtgactg     600
tctaccatcg ccgggggatcc cggagctatg tgcctcttgc tcattccagc tcagccttca    660
```

```
ccattactga ccaggtgcct ttctccgtga gcgtgtccca gttgcgggcc ttggatggag      720
ggaacaagca cttcctgaga aatcagcctc tgacctttgc cctccagctc catgacccca      780
gtggctatct ggctgaagct gacctctcct acacctggga cttggagac agtagtggaa       840 ccctgatctc tcgggcactt gtggtcactc atacttacct ggagcctggc ccagtcactg      900
cccaggtggt cctgcaggct gccattcctc tcacctcctg tggctcctcc ccagttccag      960
gcaccacaga tgggcacagg ccaactgcag aggcccctaa caccacagct ggccaagtgc     1020
ctactacaga agttgtgggt actacacctg tcaggcgcc aactgcagag ccctctggaa      1080
ccacatctgt gcaggtgcca accactgaag tcataagcac tgcacctgtg cagatgccaa     1140
ctgcagagag cacaggtatg acacctgaga aggtgccagt ttcagaggtc atgggtacca     1200
cactggcaga tgtcaact ccagaggcta caggtatgac acctgcagag gtatcaattg      1260
tggtgctttc tggaaccaca gctgcacagg taacaactac agagtgggtg agaccacag      1320 ctagagagct acctatccct gagcctgaag gtccagatgc cagctcaatc atgtctacgg     1380
aaagtattac aggttccctg ggcccccctgc tggatggtac agccacctta aggctggtga    1440
agagacaagt cccctggat tgtgttctgt atcgatatgg ttcctttcc gtcaccctgg       1500 acattgtcca gggtattgaa agtgccgaga tcctgcaggc tgtgccgtcc ggtgagggg      1560 atgcatttga gctgactgtg tcctgccaag gcgggctgcc caaggaagcc tgcatggaga    1620
tctcatcgcc agggtgccag ccccctgccc agcggctgtg ccagcctgtg ctacccagcc    1680
cagcctgcca gctggttctg caccagatac tgaagggtgg ctcggggaca tactgcctca    1740
atgtgtctct ggctgatacc aacagcctgg cagtggtcag cacccagctt atcatgcctg    1800
gtcaagaagc aggccttggg caggttccgc tgatcgtggg catcttgctg gtgttgatgg    1860
ctgtggtcct tgcatctctg atatataggc gcagacttat gaagcaagac ttctccgtac    1920
cccagttgcc acatagcagc agtcactggc tgcgtctacc ccgcatcttc tgctcttgtc    1980
ccattggtga aacagccccc ctcctcagtg ggcagcaggt ctgagtactc tcatatgatg    2040
ctgtgatttt cctggagttg acagaaacac ctatatttcc cccagtcttc cctgggagac    2100
tactattaac tgaaataaat actcagagcc tgaaaaaaaa taaaaaaaaa aaaaaaaaa     2160 aaaaaaaaaa aa                                                       2172
```

<210> SEQ ID NO 27
<211> LENGTH: 661
<212> TYPE: PRT
<213> ORGANISM: Homo sapiens

<400> SEQUENCE: 27

```
Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95
```

-continued

```
Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Phe Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
            260                 265                 270

Ala Leu Val Val Thr His Thr Tyr Leu Glu Pro Gly Pro Val Thr Ala
        275                 280                 285

Gln Val Val Leu Gln Ala Ala Ile Pro Leu Thr Ser Cys Gly Ser Ser
    290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
            340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
    370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
            420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
    450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
```

```
                515                 520                 525
Ser Ser Pro Gly Cys Gln Pro Ala Gln Arg Leu Cys Gln Pro Val
    530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Arg Leu Met Lys Gln Asp
    610                 615                 620

Phe Ser Val Pro Gln Leu Pro His Ser Ser His His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
        660

<210> SEQ ID NO 28
<211> LENGTH: 7
<212> TYPE: PRT
<213> ORGANISM: Artificial
<220> FEATURE:
<223> OTHER INFORMATION: Synthetic

<400> SEQUENCE: 28

Val Pro Gly Ile Leu Leu Thr
1               5

<210> SEQ ID NO 29
<211> LENGTH: 7
<212> TYPE: PRT
<213> ORGANISM: Artificial
<220> FEATURE:
<223> OTHER INFORMATION: Synthetic

<400> SEQUENCE: 29

Leu Leu Ser Gly Gln Gln Val
1               5

<210> SEQ ID NO 30
<211> LENGTH: 12
<212> TYPE: PRT
<213> ORGANISM: Artificial
<220> FEATURE:
<223> OTHER INFORMATION: Synthetic

<400> SEQUENCE: 30

Pro Pro Gln Trp Ala Ala Gly Leu Ser Thr Leu Ile
1               5                   10

<210> SEQ ID NO 31
<211> LENGTH: 9
<212> TYPE: PRT
<213> ORGANISM: Artificial
<220> FEATURE:
<223> OTHER INFORMATION: Synthetic

<400> SEQUENCE: 31

Met Leu Leu Ala Val Leu Tyr Cys Leu
```

<210> SEQ ID NO 32
<211> LENGTH: 9
<212> TYPE: PRT
<213> ORGANISM: Artificial
<220> FEATURE:
<223> OTHER INFORMATION: Synthetic

<400> SEQUENCE: 32

Tyr Met Asn Gly Thr Met Ser Gln Val
1               5

<210> SEQ ID NO 33
<211> LENGTH: 10
<212> TYPE: PRT
<213> ORGANISM: Artificial
<220> FEATURE:
<223> OTHER INFORMATION: Synthetic

<400> SEQUENCE: 33

Leu Leu Asp Gly Thr Ala Thr Leu Arg Leu
1               5                   10

<210> SEQ ID NO 34
<211> LENGTH: 10
<212> TYPE: PRT
<213> ORGANISM: Artificial
<220> FEATURE:
<223> OTHER INFORMATION: Synthetic

<400> SEQUENCE: 34

Val Leu Tyr Arg Tyr Gly Ser Phe Ser Val
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic

<400> SEQUENCE: 35

Ala Leu Asp Gly Gly Asn Lys His Phe Leu
1               5                   10

<210> SEQ ID NO 36
<211> LENGTH: 9
<212> TYPE: PRT
<213> ORGANISM: Artificial
<220> FEATURE:
<223> OTHER INFORMATION: Synthetic

<400> SEQUENCE: 36

Val Leu Lys Arg Cys Leu Leu His Leu
1               5

<210> SEQ ID NO 37
<211> LENGTH: 10
<212> TYPE: PRT
<213> ORGANISM: Artificial
<220> FEATURE:
<223> OTHER INFORMATION: Synthetic

<400> SEQUENCE: 37

Val Leu Pro Ser Pro Ala Cys Gln Leu Val
1               5                   10

```
<210> SEQ ID NO 38
<211> LENGTH: 10
<212> TYPE: PRT
<213> ORGANISM: Artificial
<220> FEATURE:
<223> OTHER INFORMATION: Synthetic

<400> SEQUENCE: 38

Ser Leu Ala Asp Thr Asn Ser Leu Ala Val
1               5                   10

<210> SEQ ID NO 39
<211> LENGTH: 9
<212> TYPE: PRT
<213> ORGANISM: Artificial
<220> FEATURE:
<223> OTHER INFORMATION: Synthetic

<400> SEQUENCE: 39

Ser Val Ser Val Ser Gln Leu Arg Ala
1               5

<210> SEQ ID NO 40
<211> LENGTH: 9
<212> TYPE: PRT
<213> ORGANISM: Artificial
<220> FEATURE:
<223> OTHER INFORMATION: Synthetic

<400> SEQUENCE: 40

Tyr Leu Glu Pro Gly Pro Val Thr Ala
1               5

<210> SEQ ID NO 41
<211> LENGTH: 9
<212> TYPE: PRT
<213> ORGANISM: Artificial
<220> FEATURE:
<223> OTHER INFORMATION: Synthetic

<400> SEQUENCE: 41

Leu Asn Val Ser Leu Ala Asp Thr Asn
1               5

<210> SEQ ID NO 42
<211> LENGTH: 58
<212> TYPE: DNA
<213> ORGANISM: Artificial
<220> FEATURE:
<223> OTHER INFORMATION: Synthetic

<400> SEQUENCE: 42
ggacaggccg aggcggcctt tttttttttt tttttttttt tttttttttt tttttttt        58

<210> SEQ ID NO 43
<211> LENGTH: 12
<212> TYPE: DNA
<213> ORGANISM: Artificial
<220> FEATURE:
<223> OTHER INFORMATION: Synthetic

<400> SEQUENCE: 43
ccaatcgcga cc                                                          12

<210> SEQ ID NO 44
```

```
<211> LENGTH: 15
<212> TYPE: DNA
<213> ORGANISM: Artificial
<220> FEATURE:
<223> OTHER INFORMATION: Synthetic

<400> SEQUENCE: 44
ggtcgcgatt ggtaa                                                      15

<210> SEQ ID NO 45
<211> LENGTH: 9
<212> TYPE: PRT
<213> ORGANISM: Artificial
<220> FEATURE:
<223> OTHER INFORMATION: Synthetic

<400> SEQUENCE: 45

Gly Ile Leu Gly Phe Val Phe Thr Leu
1               5

<210> SEQ ID NO 46
<211> LENGTH: 9
<212> TYPE: PRT
<213> ORGANISM: Artificial
<220> FEATURE:
<223> OTHER INFORMATION: Synthetic

<400> SEQUENCE: 46

Lys Thr Trp Gly Gln Tyr Trp Gln Val
1               5

<210> SEQ ID NO 47
<211> LENGTH: 10
<212> TYPE: PRT
<213> ORGANISM: Artificial
<220> FEATURE:
<223> OTHER INFORMATION: Synthetic

<400> SEQUENCE: 47

Lys Thr Trp Gly Gln Tyr Trp Gln Val Leu
1               5                   10

<210> SEQ ID NO 48
<211> LENGTH: 9
<212> TYPE: PRT
<213> ORGANISM: Artificial
<220> FEATURE:
<223> OTHER INFORMATION: Synthetic

<400> SEQUENCE: 48

Ile Thr Asp Gln Val Pro Phe Ser Val
1               5

<210> SEQ ID NO 49
<211> LENGTH: 10
<212> TYPE: PRT
<213> ORGANISM: Artificial
<220> FEATURE:
<223> OTHER INFORMATION: Synthetic

<400> SEQUENCE: 49

Thr Ile Thr Asp Gln Val Pro Phe Ser Val
1               5                   10

<210> SEQ ID NO 50
<211> LENGTH: 9
<212> TYPE: PRT
```

```
<213> ORGANISM: Artificial
<220> FEATURE:
<223> OTHER INFORMATION: Synthetic

<400> SEQUENCE: 50

Ala Leu Gly Ile Gly Ile Leu Thr Val
1               5

<210> SEQ ID NO 51
<211> LENGTH: 9
<212> TYPE: PRT
<213> ORGANISM: Artificial
<220> FEATURE:
<223> OTHER INFORMATION: Synthetic

<400> SEQUENCE: 51

Ala Met Gly Ile Gly Ile Leu Thr Val
1               5

<210> SEQ ID NO 52
<211> LENGTH: 9
<212> TYPE: PRT
<213> ORGANISM: Artificial
<220> FEATURE:
<223> OTHER INFORMATION: Synthetic

<400> SEQUENCE: 52

Ala Ile Gly Ile Gly Ile Leu Thr Val
1               5

<210> SEQ ID NO 53
<211> LENGTH: 9
<212> TYPE: PRT
<213> ORGANISM: Artificial
<220> FEATURE:
<223> OTHER INFORMATION: Synthetic

<400> SEQUENCE: 53

Trp Ala Gly Ile Gly Ile Leu Thr Val
1               5

<210> SEQ ID NO 54
<211> LENGTH: 9
<212> TYPE: PRT
<213> ORGANISM: Artificial
<220> FEATURE:
<223> OTHER INFORMATION: Synthetic

<400> SEQUENCE: 54

Phe Ala Gly Ile Gly Ile Leu Thr Val
1               5

<210> SEQ ID NO 55
<211> LENGTH: 9
<212> TYPE: PRT
<213> ORGANISM: Artificial
<220> FEATURE:
<223> OTHER INFORMATION: Synthetic

<400> SEQUENCE: 55

Tyr Ala Gly Ile Gly Ile Leu Thr Val
1               5

<210> SEQ ID NO 56
<211> LENGTH: 9
<212> TYPE: PRT
<213> ORGANISM: Artificial
```

```
<220> FEATURE:
<223> OTHER INFORMATION: Synthetic

<400> SEQUENCE: 56

Ala Ala Trp Ile Gly Ile Leu Thr Val
1               5

<210> SEQ ID NO 57
<211> LENGTH: 9
<212> TYPE: PRT
<213> ORGANISM: Artificial
<220> FEATURE:
<223> OTHER INFORMATION: Synthetic

<400> SEQUENCE: 57

Ala Ala Phe Ile Gly Ile Leu Thr Val
1               5

<210> SEQ ID NO 58
<211> LENGTH: 9
<212> TYPE: PRT
<213> ORGANISM: Artificial
<220> FEATURE:
<223> OTHER INFORMATION: Synthetic

<400> SEQUENCE: 58

Ala Ala Tyr Ile Gly Ile Leu Thr Val
1               5

<210> SEQ ID NO 59
<211> LENGTH: 9
<212> TYPE: PRT
<213> ORGANISM: Artificial
<220> FEATURE:
<223> OTHER INFORMATION: Synthetic

<400> SEQUENCE: 59

Lys Leu Gly Ile Gly Ile Leu Thr Val
1               5

<210> SEQ ID NO 60
<211> LENGTH: 9
<212> TYPE: PRT
<213> ORGANISM: Artificial
<220> FEATURE:
<223> OTHER INFORMATION: Synthetic

<400> SEQUENCE: 60

Lys Met Gly Ile Gly Ile Leu Thr Val
1               5

<210> SEQ ID NO 61
<211> LENGTH: 9
<212> TYPE: PRT
<213> ORGANISM: Artificial
<220> FEATURE:
<223> OTHER INFORMATION: Synthetic

<400> SEQUENCE: 61

Lys Ile Gly Ile Gly Ile Leu Thr Val
1               5

<210> SEQ ID NO 62
<211> LENGTH: 9
<212> TYPE: PRT
<213> ORGANISM: Artificial
<220> FEATURE:
```

<223> OTHER INFORMATION: Synthetic

<400> SEQUENCE: 62

Trp Leu Gly Ile Gly Ile Leu Thr Val
1               5

<210> SEQ ID NO 63
<211> LENGTH: 9
<212> TYPE: PRT
<213> ORGANISM: Artificial
<220> FEATURE:
<223> OTHER INFORMATION: Synthetic

<400> SEQUENCE: 63

Phe Leu Gly Ile Gly Ile Leu Thr Val
1               5

<210> SEQ ID NO 64
<211> LENGTH: 9
<212> TYPE: PRT
<213> ORGANISM: Artificial
<220> FEATURE:
<223> OTHER INFORMATION: Synthetic

<400> SEQUENCE: 64

Tyr Leu Gly Ile Gly Ile Leu Thr Val
1               5

<210> SEQ ID NO 65
<211> LENGTH: 9
<212> TYPE: PRT
<213> ORGANISM: Artificial
<220> FEATURE:
<223> OTHER INFORMATION: Synthetic

<400> SEQUENCE: 65

Ala Leu Trp Ile Gly Ile Leu Thr Val
1               5

<210> SEQ ID NO 66
<211> LENGTH: 9
<212> TYPE: PRT
<213> ORGANISM: Artificial
<220> FEATURE:
<223> OTHER INFORMATION: Synthetic

<400> SEQUENCE: 66

Ala Leu Phe Ile Gly Ile Leu Thr Val
1               5

<210> SEQ ID NO 67
<211> LENGTH: 9
<212> TYPE: PRT
<213> ORGANISM: Artificial
<220> FEATURE:
<223> OTHER INFORMATION: Synthetic

<400> SEQUENCE: 67

Ala Leu Tyr Ile Gly Ile Leu Thr Val
1               5

<210> SEQ ID NO 68
<211> LENGTH: 9
<212> TYPE: PRT
<213> ORGANISM: Artificial
<220> FEATURE:
<223> OTHER INFORMATION: Synthetic

```
<400> SEQUENCE: 68

Lys Leu Trp Gly Gln Tyr Trp Gln Val
1               5

<210> SEQ ID NO 69
<211> LENGTH: 9
<212> TYPE: PRT
<213> ORGANISM: Artificial
<220> FEATURE:
<223> OTHER INFORMATION: Synthetic

<400> SEQUENCE: 69

Lys Met Trp Gly Gln Tyr Trp Gln Val
1               5

<210> SEQ ID NO 70
<211> LENGTH: 9
<212> TYPE: PRT
<213> ORGANISM: Artificial
<220> FEATURE:
<223> OTHER INFORMATION: Synthetic

<400> SEQUENCE: 70

Lys Ile Trp Gly Gln Tyr Trp Gln Val
1               5

<210> SEQ ID NO 71
<211> LENGTH: 9
<212> TYPE: PRT
<213> ORGANISM: Artificial
<220> FEATURE:
<223> OTHER INFORMATION: Synthetic

<400> SEQUENCE: 71

Trp Thr Trp Gly Gln Tyr Trp Gln Val
1               5

<210> SEQ ID NO 72
<211> LENGTH: 9
<212> TYPE: PRT
<213> ORGANISM: Artificial
<220> FEATURE:
<223> OTHER INFORMATION: Synthetic

<400> SEQUENCE: 72

Phe Thr Trp Gly Gln Tyr Trp Gln Val
1               5

<210> SEQ ID NO 73
<211> LENGTH: 9
<212> TYPE: PRT
<213> ORGANISM: Artificial
<220> FEATURE:
<223> OTHER INFORMATION: Synthetic

<400> SEQUENCE: 73

Tyr Thr Trp Gly Gln Tyr Trp Gln Val
1               5

<210> SEQ ID NO 74
<211> LENGTH: 9
<212> TYPE: PRT
<213> ORGANISM: Artificial
<220> FEATURE:
<223> OTHER INFORMATION: Synthetic
```

<400> SEQUENCE: 74

Ala Thr Trp Gly Gln Tyr Trp Gln Val
1               5

<210> SEQ ID NO 75
<211> LENGTH: 9
<212> TYPE: PRT
<213> ORGANISM: Artificial
<220> FEATURE:
<223> OTHER INFORMATION: Synthetic

<400> SEQUENCE: 75

Leu Thr Trp Gly Gln Tyr Trp Gln Val
1               5

<210> SEQ ID NO 76
<211> LENGTH: 9
<212> TYPE: PRT
<213> ORGANISM: Artificial
<220> FEATURE:
<223> OTHER INFORMATION: Synthetic

<400> SEQUENCE: 76

Lys Thr Tyr Gly Gln Tyr Trp Gln Val
1               5

<210> SEQ ID NO 77
<211> LENGTH: 9
<212> TYPE: PRT
<213> ORGANISM: Artificial
<220> FEATURE:
<223> OTHER INFORMATION: Synthetic

<400> SEQUENCE: 77

Lys Thr Phe Gly Gln Tyr Trp Gln Val
1               5

<210> SEQ ID NO 78
<211> LENGTH: 9
<212> TYPE: PRT
<213> ORGANISM: Artificial
<220> FEATURE:
<223> OTHER INFORMATION: Synthetic

<400> SEQUENCE: 78

Ala Leu Trp Gly Gln Tyr Trp Gln Val
1               5

<210> SEQ ID NO 79
<211> LENGTH: 9
<212> TYPE: PRT
<213> ORGANISM: Artificial
<220> FEATURE:
<223> OTHER INFORMATION: Synthetic

<400> SEQUENCE: 79

Leu Leu Trp Gly Gln Tyr Trp Gln Val
1               5

<210> SEQ ID NO 80
<211> LENGTH: 9
<212> TYPE: PRT
<213> ORGANISM: Artificial
<220> FEATURE:
<223> OTHER INFORMATION: Synthetic

<400> SEQUENCE: 80

```
Trp Leu Trp Gly Gln Tyr Trp Gln Val
1               5

<210> SEQ ID NO 81
<211> LENGTH: 9
<212> TYPE: PRT
<213> ORGANISM: Artificial
<220> FEATURE:
<223> OTHER INFORMATION: Synthetic

<400> SEQUENCE: 81

Phe Leu Trp Gly Gln Tyr Trp Gln Val
1               5

<210> SEQ ID NO 82
<211> LENGTH: 9
<212> TYPE: PRT
<213> ORGANISM: Artificial
<220> FEATURE:
<223> OTHER INFORMATION: Synthetic

<400> SEQUENCE: 82

Tyr Leu Trp Gly Gln Tyr Trp Gln Val
1               5

<210> SEQ ID NO 83
<211> LENGTH: 9
<212> TYPE: PRT
<213> ORGANISM: Artificial
<220> FEATURE:
<223> OTHER INFORMATION: Synthetic

<400> SEQUENCE: 83

Ile Leu Asp Gln Val Pro Phe Ser Val
1               5

<210> SEQ ID NO 84
<211> LENGTH: 9
<212> TYPE: PRT
<213> ORGANISM: Artificial
<220> FEATURE:
<223> OTHER INFORMATION: Synthetic

<400> SEQUENCE: 84

Ile Met Asp Gln Val Pro Phe Ser Val
1               5

<210> SEQ ID NO 85
<211> LENGTH: 9
<212> TYPE: PRT
<213> ORGANISM: Artificial
<220> FEATURE:
<223> OTHER INFORMATION: Synthetic

<400> SEQUENCE: 85

Ile Ile Asp Gln Val Pro Phe Ser Val
1               5

<210> SEQ ID NO 86
<211> LENGTH: 9
<212> TYPE: PRT
<213> ORGANISM: Artificial
<220> FEATURE:
<223> OTHER INFORMATION: Synthetic

<400> SEQUENCE: 86
```

```
Phe Thr Asp Gln Val Pro Phe Ser Val
1               5

<210> SEQ ID NO 87
<211> LENGTH: 9
<212> TYPE: PRT
<213> ORGANISM: Artificial
<220> FEATURE:
<223> OTHER INFORMATION: Synthetic

<400> SEQUENCE: 87

Trp Thr Asp Gln Val Pro Phe Ser Val
1               5

<210> SEQ ID NO 88
<211> LENGTH: 9
<212> TYPE: PRT
<213> ORGANISM: Artificial
<220> FEATURE:
<223> OTHER INFORMATION: Synthetic

<400> SEQUENCE: 88

Tyr Thr Asp Gln Val Pro Phe Ser Val
1               5

<210> SEQ ID NO 89
<211> LENGTH: 9
<212> TYPE: PRT
<213> ORGANISM: Artificial
<220> FEATURE:
<223> OTHER INFORMATION: Synthetic

<400> SEQUENCE: 89

Ile Thr Trp Gln Val Pro Phe Ser Val
1               5

<210> SEQ ID NO 90
<211> LENGTH: 9
<212> TYPE: PRT
<213> ORGANISM: Artificial
<220> FEATURE:
<223> OTHER INFORMATION: Synthetic

<400> SEQUENCE: 90

Ile Thr Phe Gln Val Pro Phe Ser Val
1               5

<210> SEQ ID NO 91
<211> LENGTH: 9
<212> TYPE: PRT
<213> ORGANISM: Artificial
<220> FEATURE:
<223> OTHER INFORMATION: Synthetic

<400> SEQUENCE: 91

Ile Thr Tyr Gln Val Pro Phe Ser Val
1               5

<210> SEQ ID NO 92
<211> LENGTH: 9
<212> TYPE: PRT
<213> ORGANISM: Artificial
<220> FEATURE:
<223> OTHER INFORMATION: Synthetic

<400> SEQUENCE: 92

Ile Thr Ala Gln Val Pro Phe Ser Val
```

```
1               5

<210> SEQ ID NO 93
<211> LENGTH: 9
<212> TYPE: PRT
<213> ORGANISM: Artificial
<220> FEATURE:
<223> OTHER INFORMATION: Synthetic

<400> SEQUENCE: 93

Ile Thr Met Gln Val Pro Phe Ser Val
1               5

<210> SEQ ID NO 94
<211> LENGTH: 9
<212> TYPE: PRT
<213> ORGANISM: Artificial
<220> FEATURE:
<223> OTHER INFORMATION: Synthetic

<400> SEQUENCE: 94

Ile Thr Ser Gln Val Pro Phe Ser Val
1               5

<210> SEQ ID NO 95
<211> LENGTH: 9
<212> TYPE: PRT
<213> ORGANISM: Artificial
<220> FEATURE:
<223> OTHER INFORMATION: Synthetic

<400> SEQUENCE: 95

Ile Leu Trp Gln Val Pro Phe Ser Val
1               5

<210> SEQ ID NO 96
<211> LENGTH: 9
<212> TYPE: PRT
<213> ORGANISM: Artificial
<220> FEATURE:
<223> OTHER INFORMATION: Synthetic

<400> SEQUENCE: 96

Ile Leu Phe Gln Val Pro Phe Ser Val
1               5

<210> SEQ ID NO 97
<211> LENGTH: 9
<212> TYPE: PRT
<213> ORGANISM: Artificial
<220> FEATURE:
<223> OTHER INFORMATION: Synthetic

<400> SEQUENCE: 97

Ile Leu Tyr Gln Val Pro Phe Ser Val
1               5

<210> SEQ ID NO 98
<211> LENGTH: 9
<212> TYPE: PRT
<213> ORGANISM: Artificial
<220> FEATURE:
<223> OTHER INFORMATION: Synthetic

<400> SEQUENCE: 98

Ile Leu Ala Gln Val Pro Phe Ser Val
1               5
```

```
<210> SEQ ID NO 99
<211> LENGTH: 9
<212> TYPE: PRT
<213> ORGANISM: Artificial
<220> FEATURE:
<223> OTHER INFORMATION: Synthetic

<400> SEQUENCE: 99

Ile Leu Met Gln Val Pro Phe Ser Val
1               5

<210> SEQ ID NO 100
<211> LENGTH: 9
<212> TYPE: PRT
<213> ORGANISM: Artificial
<220> FEATURE:
<223> OTHER INFORMATION: Synthetic

<400> SEQUENCE: 100

Ile Leu Ser Gln Val Pro Phe Ser Val
1               5

<210> SEQ ID NO 101
<211> LENGTH: 9
<212> TYPE: PRT
<213> ORGANISM: Artificial
<220> FEATURE:
<223> OTHER INFORMATION: Synthetic

<400> SEQUENCE: 101

Trp Leu Asp Gln Val Pro Phe Ser Val
1               5

<210> SEQ ID NO 102
<211> LENGTH: 9
<212> TYPE: PRT
<213> ORGANISM: Artificial
<220> FEATURE:
<223> OTHER INFORMATION: Synthetic

<400> SEQUENCE: 102

Phe Leu Asp Gln Val Pro Phe Ser Val
1               5

<210> SEQ ID NO 103
<211> LENGTH: 9
<212> TYPE: PRT
<213> ORGANISM: Artificial
<220> FEATURE:
<223> OTHER INFORMATION: Synthetic

<400> SEQUENCE: 103

Tyr Leu Asp Gln Val Pro Phe Ser Val
1               5

<210> SEQ ID NO 104
<211> LENGTH: 9
<212> TYPE: PRT
<213> ORGANISM: Artificial
<220> FEATURE:
<223> OTHER INFORMATION: Synthetic

<400> SEQUENCE: 104

Tyr Leu Glu Pro Gly Pro Val Thr Val
1               5
```

```
<210> SEQ ID NO 105
<211> LENGTH: 9
<212> TYPE: PRT
<213> ORGANISM: Artificial
<220> FEATURE:
<223> OTHER INFORMATION: Synthetic

<400> SEQUENCE: 105

Tyr Leu Glu Pro Gly Pro Val Thr Leu
1               5

<210> SEQ ID NO 106
<211> LENGTH: 9
<212> TYPE: PRT
<213> ORGANISM: Artificial
<220> FEATURE:
<223> OTHER INFORMATION: Synthetic

<400> SEQUENCE: 106

Tyr Leu Glu Pro Gly Pro Val Thr Ile
1               5

<210> SEQ ID NO 107
<211> LENGTH: 9
<212> TYPE: PRT
<213> ORGANISM: Artificial
<220> FEATURE:
<223> OTHER INFORMATION: Synthetic

<400> SEQUENCE: 107

Phe Leu Glu Pro Gly Pro Val Thr Ala
1               5

<210> SEQ ID NO 108
<211> LENGTH: 9
<212> TYPE: PRT
<213> ORGANISM: Artificial
<220> FEATURE:
<223> OTHER INFORMATION: Synthetic

<400> SEQUENCE: 108

Trp Leu Glu Pro Gly Pro Val Thr Ala
1               5

<210> SEQ ID NO 109
<211> LENGTH: 9
<212> TYPE: PRT
<213> ORGANISM: Artificial
<220> FEATURE:
<223> OTHER INFORMATION: Synthetic

<400> SEQUENCE: 109

Tyr Leu Tyr Pro Gly Pro Val Thr Ala
1               5

<210> SEQ ID NO 110
<211> LENGTH: 9
<212> TYPE: PRT
<213> ORGANISM: Artificial
<220> FEATURE:
<223> OTHER INFORMATION: Synthetic

<400> SEQUENCE: 110

Tyr Leu Trp Pro Gly Pro Val Thr Ala
1               5
```

```
<210> SEQ ID NO 111
<211> LENGTH: 9
<212> TYPE: PRT
<213> ORGANISM: Artificial
<220> FEATURE:
<223> OTHER INFORMATION: Synthetic

<400> SEQUENCE: 111

Tyr Leu Phe Pro Gly Pro Val Thr Ala
1               5

<210> SEQ ID NO 112
<211> LENGTH: 9
<212> TYPE: PRT
<213> ORGANISM: Artificial
<220> FEATURE:
<223> OTHER INFORMATION: Synthetic

<400> SEQUENCE: 112

Tyr Leu Met Pro Gly Pro Val Thr Ala
1               5

<210> SEQ ID NO 113
<211> LENGTH: 9
<212> TYPE: PRT
<213> ORGANISM: Artificial
<220> FEATURE:
<223> OTHER INFORMATION: Synthetic

<400> SEQUENCE: 113

Tyr Leu Ser Pro Gly Pro Val Thr Ala
1               5

<210> SEQ ID NO 114
<211> LENGTH: 9
<212> TYPE: PRT
<213> ORGANISM: Artificial
<220> FEATURE:
<223> OTHER INFORMATION: Synthetic

<400> SEQUENCE: 114

Tyr Leu Ala Pro Gly Pro Val Thr Ala
1               5

<210> SEQ ID NO 115
<211> LENGTH: 9
<212> TYPE: PRT
<213> ORGANISM: Artificial
<220> FEATURE:
<223> OTHER INFORMATION: Synthetic

<400> SEQUENCE: 115

Tyr Leu Met Pro Gly Pro Val Thr Val
1               5

<210> SEQ ID NO 116
<211> LENGTH: 9
<212> TYPE: PRT
<213> ORGANISM: Artificial
<220> FEATURE:
<223> OTHER INFORMATION: Synthetic

<400> SEQUENCE: 116

Tyr Leu Ser Pro Gly Pro Val Thr Val
1               5

<210> SEQ ID NO 117
```

```
<211> LENGTH: 9
<212> TYPE: PRT
<213> ORGANISM: Artificial
<220> FEATURE:
<223> OTHER INFORMATION: Synthetic

<400> SEQUENCE: 117

Tyr Leu Ala Pro Gly Pro Val Thr Val
1               5

<210> SEQ ID NO 118
<211> LENGTH: 9
<212> TYPE: PRT
<213> ORGANISM: Artificial
<220> FEATURE:
<223> OTHER INFORMATION: Synthetic

<400> SEQUENCE: 118

Tyr Leu Tyr Pro Gly Pro Val Thr Val
1               5

<210> SEQ ID NO 119
<211> LENGTH: 9
<212> TYPE: PRT
<213> ORGANISM: Artificial
<220> FEATURE:
<223> OTHER INFORMATION: Synthetic

<400> SEQUENCE: 119

Tyr Leu Phe Pro Gly Pro Val Thr Val
1               5

<210> SEQ ID NO 120
<211> LENGTH: 9
<212> TYPE: PRT
<213> ORGANISM: Artificial
<220> FEATURE:
<223> OTHER INFORMATION: Synthetic

<400> SEQUENCE: 120

Tyr Leu Trp Pro Gly Pro Val Thr Val
1               5

<210> SEQ ID NO 121
<211> LENGTH: 661
<212> TYPE: PRT
<213> ORGANISM: Homo sapiens

<400> SEQUENCE: 121

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110
```

```
Ser Gln Val Trp Gly Gly Gln Pro Val Tyr Pro Gln Glu Thr Asp Asp
        115                 120                 125

Ala Cys Ile Phe Pro Asp Gly Pro Cys Pro Ser Gly Ser Trp Ser
130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
                180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
        210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile Ser Arg
                260                 265                 270

Ala Leu Val Val Thr His Thr Tyr Leu Glu Pro Gly Pro Val Thr Ala
                275                 280                 285

Gln Val Val Leu Gln Ala Ala Ile Pro Leu Thr Ser Cys Gly Ser Ser
        290                 295                 300

Pro Val Pro Gly Thr Thr Asp Gly His Arg Pro Thr Ala Glu Ala Pro
305                 310                 315                 320

Asn Thr Thr Ala Gly Gln Val Pro Thr Thr Glu Val Val Gly Thr Thr
                325                 330                 335

Pro Gly Gln Ala Pro Thr Ala Glu Pro Ser Gly Thr Thr Ser Val Gln
                340                 345                 350

Val Pro Thr Thr Glu Val Ile Ser Thr Ala Pro Val Gln Met Pro Thr
        355                 360                 365

Ala Glu Ser Thr Gly Met Thr Pro Glu Lys Val Pro Val Ser Glu Val
        370                 375                 380

Met Gly Thr Thr Leu Ala Glu Met Ser Thr Pro Glu Ala Thr Gly Met
385                 390                 395                 400

Thr Pro Ala Glu Val Ser Ile Val Val Leu Ser Gly Thr Thr Ala Ala
                405                 410                 415

Gln Val Thr Thr Thr Glu Trp Val Glu Thr Thr Ala Arg Glu Leu Pro
                420                 425                 430

Ile Pro Glu Pro Glu Gly Pro Asp Ala Ser Ser Ile Met Ser Thr Glu
        435                 440                 445

Ser Ile Thr Gly Ser Leu Gly Pro Leu Leu Asp Gly Thr Ala Thr Leu
        450                 455                 460

Arg Leu Val Lys Arg Gln Val Pro Leu Asp Cys Val Leu Tyr Arg Tyr
465                 470                 475                 480

Gly Ser Phe Ser Val Thr Leu Asp Ile Val Gln Gly Ile Glu Ser Ala
                485                 490                 495

Glu Ile Leu Gln Ala Val Pro Ser Gly Glu Gly Asp Ala Phe Glu Leu
                500                 505                 510

Thr Val Ser Cys Gln Gly Gly Leu Pro Lys Glu Ala Cys Met Glu Ile
        515                 520                 525

Ser Ser Pro Gly Cys Gln Pro Pro Ala Gln Arg Leu Cys Gln Pro Val
```

-continued

```
                530                 535                 540
Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
        595                 600                 605

Val Val Leu Ala Ser Leu Ile Tyr Arg Arg Leu Met Lys Gln Asp
    610                 615                 620

Phe Ser Val Pro Gln Leu Pro His Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

<210> SEQ ID NO 122
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" at position 1 is any amino acid
<220> FEATURE:
<221> NAME/KEY: misc_feature
<222> LOCATION: (2)..(2)
<223> OTHER INFORMATION: "Xaa" at position 2 is any hydrophobic amino
     acid
<220> FEATURE:
<221> NAME/KEY: misc_feature
<222> LOCATION: (3)..(3)
<223> OTHER INFORMATION: "Xaa" at position 3 is any amino acid
<220> FEATURE:
<221> NAME/KEY: misc_feature
<222> LOCATION: (9)..(9)
<223> OTHER INFORMATION: "Xaa" at position 9 is any hydrophobic amino
     acid

<400> SEQUENCE: 122

Xaa Xaa Xaa Ile Gly Ile Leu Thr Xaa
1               5

<210> SEQ ID NO 123
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" at position 1 is any amino acid
<220> FEATURE:
<221> NAME/KEY: misc_feature
<222> LOCATION: (2)..(2)
<223> OTHER INFORMATION: "Xaa" at position 2 is any hydrophobic amino
     acid
<220> FEATURE:
<221> NAME/KEY: misc_feature
<222> LOCATION: (3)..(3)
<223> OTHER INFORMATION: "Xaa" at position 3 is any amino acid
<220> FEATURE:
<221> NAME/KEY: misc_feature
```

```
<222> LOCATION: (9)..(9)
<223> OTHER INFORMATION: "Xaa" at position 9 is any hydrophobic amino
      acid

<400> SEQUENCE: 123

Xaa Xaa Xaa Gly Gln Tyr Trp Gln Xaa
1               5

<210> SEQ ID NO 124
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" at position 1 is any amino acid
<220> FEATURE:
<221> NAME/KEY: misc_feature
<222> LOCATION: (2)..(2)
<223> OTHER INFORMATION: "Xaa" at position 2 is any hydrophobic amino
      acid
<220> FEATURE:
<221> NAME/KEY: misc_feature
<222> LOCATION: (3)..(3)
<223> OTHER INFORMATION: "Xaa" at position 3 is any amino acid
<220> FEATURE:
<221> NAME/KEY: misc_feature
<222> LOCATION: (9)..(9)
<223> OTHER INFORMATION: "Xaa" at position 9 is any  hydrophobic amino
      acid

<400> SEQUENCE: 124

Xaa Xaa Xaa Gln Val Pro Phe Ser Xaa
1               5

<210> SEQ ID NO 125
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: "Xaa" at position 1 is any amino acid
<220> FEATURE:
<221> NAME/KEY: misc_feature
<222> LOCATION: (2)..(2)
<223> OTHER INFORMATION: "Xaa" at position 2 is any hydrophobic amino
      acid
<220> FEATURE:
<221> NAME/KEY: misc_feature
<222> LOCATION: (3)..(3)
<223> OTHER INFORMATION: "Xaa" at position 3 is any amino acid
<220> FEATURE:
<221> NAME/KEY: misc_feature
<222> LOCATION: (9)..(9)
<223> OTHER INFORMATION: "Xaa" at position 9 is any hydrophobic amino
      acid

<400> SEQUENCE: 125

Xaa Xaa Xaa Pro Gly Pro Val Thr Xaa
1               5

<210> SEQ ID NO 126
<211> LENGTH: 10
<212> TYPE: PRT
<213> ORGANISM: Artificial
<220> FEATURE:
<223> OTHER INFORMATION: Synthetic
```

```
<400> SEQUENCE: 126

Phe Leu Pro Ser Asp Tyr Phe Pro Ser Val
1               5                   10

<210> SEQ ID NO 127
<211> LENGTH: 8
<212> TYPE: PRT
<213> ORGANISM: Artificial
<220> FEATURE:
<223> OTHER INFORMATION: Synthetic

<400> SEQUENCE: 127

Tyr Leu Glu Pro Gly Pro Val Thr
1               5

<210> SEQ ID NO 128
<211> LENGTH: 19
<212> TYPE: DNA
<213> ORGANISM: Artificial
<220> FEATURE:
<223> OTHER INFORMATION: Synthetic

<400> SEQUENCE: 128
ggacaggccg attggtaat                                                   19

<210> SEQ ID NO 129
<211> LENGTH: 154
<212> TYPE: PRT
<213> ORGANISM: Homo sapiens

<400> SEQUENCE: 129

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys
145                 150

<210> SEQ ID NO 130
<211> LENGTH: 163
<212> TYPE: PRT
<213> ORGANISM: Homo sapiens

<400> SEQUENCE: 130

Met Asp Leu Val Leu Lys Arg Cys Leu Leu His Leu Ala Val Ile Gly
1               5                   10                  15
```

-continued

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu

<210> SEQ ID NO 131
<211> LENGTH: 195
<212> TYPE: PRT
<213> ORGANISM: Homo sapiens

<400> SEQUENCE: 131

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg
        195

<210> SEQ ID NO 132
<211> LENGTH: 270

```
<212> TYPE: PRT
<213> ORGANISM: Homo sapiens

<400> SEQUENCE: 132

Met Asp Leu Val Leu Lys Arg Cys Leu Leu His Leu Ala Val Ile Gly
1               5                   10                  15

Ala Leu Leu Ala Val Gly Ala Thr Lys Val Pro Arg Asn Gln Asp Trp
            20                  25                  30

Leu Gly Val Ser Arg Gln Leu Arg Thr Lys Ala Trp Asn Arg Gln Leu
        35                  40                  45

Tyr Pro Glu Trp Thr Glu Ala Gln Arg Leu Asp Cys Trp Arg Gly Gly
    50                  55                  60

Gln Val Ser Leu Lys Val Ser Asn Asp Gly Pro Thr Leu Ile Gly Ala
65                  70                  75                  80

Asn Ala Ser Phe Ser Ile Ala Leu Asn Phe Pro Gly Ser Gln Lys Val
                85                  90                  95

Leu Pro Asp Gly Gln Val Ile Trp Val Asn Asn Thr Ile Ile Asn Gly
            100                 105                 110

Ser Gln Val Trp Gly Gly Gln Pro Val Tyr Pro Gln Glu Thr Asp Asp
        115                 120                 125

Ala Cys Ile Phe Pro Asp Gly Gly Pro Cys Pro Ser Gly Ser Trp Ser
    130                 135                 140

Gln Lys Arg Ser Phe Val Tyr Val Trp Lys Thr Trp Gly Gln Tyr Trp
145                 150                 155                 160

Gln Val Leu Gly Gly Pro Val Ser Gly Leu Ser Ile Gly Thr Gly Arg
                165                 170                 175

Ala Met Leu Gly Thr His Thr Met Glu Val Thr Val Tyr His Arg Arg
            180                 185                 190

Gly Ser Arg Ser Tyr Val Pro Leu Ala His Ser Ser Ser Ala Phe Thr
        195                 200                 205

Ile Thr Asp Gln Val Pro Phe Ser Val Ser Val Ser Gln Leu Arg Ala
    210                 215                 220

Leu Asp Gly Gly Asn Lys His Phe Leu Arg Asn Gln Pro Leu Thr Phe
225                 230                 235                 240

Ala Leu Gln Leu His Asp Pro Ser Gly Tyr Leu Ala Glu Ala Asp Leu
                245                 250                 255

Ser Tyr Thr Trp Asp Phe Gly Asp Ser Ser Gly Thr Leu Ile
            260                 265                 270

<210> SEQ ID NO 133
<211> LENGTH: 424
<212> TYPE: PRT
<213> ORGANISM: Homo sapiens

<400> SEQUENCE: 133

Gln Pro Leu Thr Phe Ala Leu Gln Leu His Asp Pro Ser Gly Tyr Leu
1               5                   10                  15

Ala Glu Ala Asp Leu Ser Tyr Thr Trp Asp Gly Asp Ser Ser Gly Thr
            20                  25                  30

Leu Ile Ser Arg Ala Leu Val Val Thr His Thr Tyr Leu Glu Pro Gly
        35                  40                  45

Pro Val Thr Ala Gln Val Val Leu Gln Ala Ala Ile Pro Leu Thr Ser
    50                  55                  60

Cys Gly Ser Ser Pro Val Pro Gly Thr Thr Asp Gly His Arg Pro Thr
65                  70                  75                  80
```

```
Ala Glu Ala Pro Asn Thr Thr Ala Gly Gln Val Pro Thr Thr Glu Val
                85                  90                  95

Val Gly Thr Thr Pro Gly Gln Ala Pro Thr Ala Glu Pro Ser Gly Thr
            100                 105                 110

Thr Ser Val Gln Val Pro Thr Thr Glu Val Ile Ser Thr Ala Pro Val
            115                 120                 125

Gln Met Pro Thr Ala Glu Ser Thr Gly Met Thr Pro Glu Lys Val Pro
130                 135                 140

Val Ser Glu Val Met Gly Thr Thr Leu Ala Glu Met Ser Thr Pro Glu
145                 150                 155                 160

Ala Thr Gly Met Thr Pro Ala Glu Val Ser Ile Val Val Leu Ser Gly
                165                 170                 175

Thr Thr Ala Ala Gln Val Thr Thr Thr Glu Trp Val Gly Thr Thr Ala
            180                 185                 190

Arg Glu Leu Pro Ile Pro Glu Pro Glu Gly Pro Asp Ala Ser Ser Ile
            195                 200                 205

Met Ser Thr Glu Ser Ile Thr Gly Ser Leu Gly Pro Leu Leu Asp Gly
210                 215                 220

Thr Ala Thr Leu Arg Leu Val Lys Arg Gln Val Pro Leu Asp Val Leu
225                 230                 235                 240

Tyr Arg Tyr Gly Ser Phe Ser Val Thr Leu Asp Ile Val Gln Gly Ile
                245                 250                 255

Glu Ser Ala Glu Ile Leu Gln Ala Val Pro Ser Gly Glu Gly Asp Ala
            260                 265                 270

Phe Glu Leu Thr Val Ser Cys Gln Gly Gly Leu Pro Lys Glu Ala Cys
            275                 280                 285

Met Glu Ile Ser Ser Pro Gly Cys Gln Pro Pro Ala Gln Arg Leu Cys
290                 295                 300

Gln Pro Val Leu Pro Ser Pro Ala Cys Gln Leu Val Leu His Gln Ile
305                 310                 315                 320

Leu Lys Gly Gly Ser Gly Thr Tyr Cys Leu Asn Val Ser Leu Ala Asp
                325                 330                 335

Thr Asn Ser Leu Ala Val Val Ser Thr Gln Leu Ile Met Pro Gly Gln
            340                 345                 350

Glu Ala Gly Leu Gly Gln Val Pro Leu Ile Val Gly Ile Leu Leu Val
            355                 360                 365

Leu Met Ala Val Val Leu Ala Ser Leu Ile Tyr Arg Arg Arg Leu Met
370                 375                 380

Lys Gln Asp Phe Ser Val Pro Gln Leu Pro His Ser Ser Ser His Trp
385                 390                 395                 400

Leu Arg Leu Pro Arg Ile Phe Cys Ser Cys Pro Ile Gly Glu Asn Ser
                405                 410                 415

Pro Leu Leu Ser Gly Gln Gln Val
            420
```

<210> SEQ ID NO 134
<211> LENGTH: 9
<212> TYPE: PRT
<213> ORGANISM: Artificial Sequence
<220> FEATURE:
<223> OTHER INFORMATION: Synthetic

<400> SEQUENCE: 134

```
Tyr Ile Glu Pro Gly Pro Val Thr Ala
1               5
```